US010066222B2

(12) United States Patent
Callen et al.

(10) Patent No.: US 10,066,222 B2
(45) Date of Patent: Sep. 4, 2018

(54) AMYLASES, NUCLEIC ACIDS ENCODING THEM AND METHOD OF PRODUCING AN OIL

(71) Applicant: BASF ENZYMES LLC, San Diego, CA (US)

(72) Inventors: Walter Callen, San Diego, CA (US); Toby Richardson, San Diego, CA (US); Gerhard Frey, San Diego, CA (US); Carl A. Miller, Raleigh, NC (US); Martin Kazaoka, San Diego, CA (US); Eric J. Mathur, Carlsbad, CA (US); Jay M. Short, Del Mar, CA (US)

(73) Assignee: BASF ENZYMES LLC, San Diego, CA (US)

( * ) Notice: Subject to any disclaimer, the term of this patent is extended or adjusted under 35 U.S.C. 154(b) by 0 days.

(21) Appl. No.: 15/636,039

(22) Filed: Jun. 28, 2017

(65) Prior Publication Data

US 2017/0306308 A1 Oct. 26, 2017

Related U.S. Application Data

(60) Division of application No. 14/719,547, filed on May 22, 2015, now Pat. No. 9,701,950, which is a continuation of application No. 13/669,776, filed on Nov. 6, 2012, now Pat. No. 9,062,295, which is a continuation of application No. 12/697,907, filed on Feb. 1, 2010, now Pat. No. 8,338,131, which is a continuation of application No. 10/489,510, filed as application No. PCT/US03/08906 on Mar. 24, 2003, now Pat. No. 7,659,102, which is a continuation-in-part of application No. 10/105,733, filed on Mar. 22, 2002, now Pat. No. 7,323,336, which is a continuation-in-part of application No. 10/081,739, filed on Feb. 21, 2002, now Pat. No. 7,273,740.

(60) Provisional application No. 60/291,122, filed on May 14, 2001, provisional application No. 60/270,495, filed on Feb. 21, 2001, provisional application No. 60/270,496, filed on Feb. 21, 2001.

(51) Int. Cl.
*C12N 9/26* (2006.01)
*C12P 19/14* (2006.01)
*C12N 9/28* (2006.01)

(52) U.S. Cl.
CPC .......... *C12N 9/2411* (2013.01); *C12N 9/2417* (2013.01); *C12P 19/14* (2013.01)

(58) Field of Classification Search
None
See application file for complete search history.

(56) References Cited

U.S. PATENT DOCUMENTS

| | | |
|---|---|---|
| 3,847,740 A | 11/1974 | Heady |
| 4,521,252 A | 6/1985 | Miyake |
| 4,557,927 A | 12/1985 | Miyake |
| 5,789,228 A | 8/1998 | Lam |
| 5,939,250 A | 8/1999 | Short |
| 6,297,037 B1 | 10/2001 | Barnett |
| 6,479,258 B1 | 11/2002 | Short |
| 7,102,057 B2 | 9/2006 | Lanahan |
| 7,273,740 B2 | 9/2007 | Callen |
| 7,557,262 B2 | 7/2009 | Lanahan |
| 7,560,126 B2 | 7/2009 | Callen |
| 2001/0053519 A1 | 12/2001 | Fodor |
| 2003/0135885 A1 | 7/2003 | Lanahan |
| 2004/0018607 A1 | 1/2004 | Callen |
| 2004/0259222 A1 | 12/2004 | Breves |
| 2005/0176000 A1 | 8/2005 | Callen |
| 2007/0157329 A1 | 7/2007 | Callen |

FOREIGN PATENT DOCUMENTS

| | | |
|---|---|---|
| CN | 1222938 A | 7/1999 |
| EP | 0606753 A2 | 12/1993 |
| EP | 0628630 A2 | 12/1994 |
| EP | 0648843 | 4/1995 |
| EP | 1284286 A1 | 11/2001 |
| FR | 2778412 | 11/1999 |
| GB | 2106912 | 4/1983 |
| JP | 58-023799 | 2/1983 |
| JP | 58-72598 | 4/1983 |
| JP | 62-104580 A2 | 5/1987 |
| JP | 09-173077 | 7/1997 |
| WO | WO 1993/000426 A1 | 1/1993 |
| WO | WO 1996/038469 | 12/1996 |
| WO | WO 1996/039528 A2 | 12/1996 |
| WO | WO 1997/044361 | 11/1997 |
| WO | WO 1998/045417 | 10/1998 |
| WO | 99/67408 A1 | 12/1999 |
| WO | WO 1999/067406 A1 | 12/1999 |

(Continued)

OTHER PUBLICATIONS

Chica et al. Curr Opin Biotechnol. Aug. 2005;16(4):378-84.*

(Continued)

*Primary Examiner* — Christian L Fronda

(74) *Attorney, Agent, or Firm* — BASF; Brian W. Siddons

(57) ABSTRACT

In one aspect, the invention is directed to polypeptides having an amylase activity, polynucleotides encoding the polypeptides, and methods for making and using these polynucleotides and polypeptides. In one aspect, the polypeptides of the invention can be used as amylases, for example, alpha amylases, to catalyze the hydrolysis of starch into sugars.

8 Claims, 22 Drawing Sheets

Specification includes a Sequence Listing.

(56) References Cited

FOREIGN PATENT DOCUMENTS

| WO | WO 1999/067408 A1 | 12/1999 |
|---|---|---|
| WO | WO 2000/058508 | 10/2000 |
| WO | WO 2001/090338 A1 | 11/2001 |
| WO | WO 2002/068589 | 9/2002 |
| WO | WO 2002/068597 A2 | 9/2002 |
| WO | 2002/029079 A2 | 11/2002 |
| WO | WO 2003/012071 A2 | 2/2003 |
| WO | WO 2004/091544 A2 | 10/2004 |

OTHER PUBLICATIONS

Singh et al. Curr Protein Pept Sci. 2017, 18, 1-11.*
Accession O33476. Jan. 1, 1998.*
Tachibana et al. J. Ferment. Bioeng. 82:224-232(1996).*
Hespell et al. Applied Biochemistry and Biotechnology (1997), 62(1), 87-97.*
JPO—Feb. 5, 2014—Second Office Action—JP2011-022288.
SIPO—Feb. 20, 2014—Thrid Office Action—CN201210020583.5.
USPTO—Mar. 20, 2014—Office Action, 892, Refs Considered—U.S. Appl. No. 13/482,919.
Saponins—Discover the Wealth of Benefits Saponins Provide—Ecological Surfactants, Inc. http://www.ecologicalsurfactants.com/saponin/—Retrieved Mar. 13, 2014.
Surfactants: the ubiquitous amphiphiles—Royal Society of Chemistry, Chemistry World, http://www.rsc.org/chemistryworld/issues/2003/july/amphiphiles.asp (2003)—Retrieved Mar. 13, 2014.
SIPO—Mar. 5, 2014—Fourth Office Action and Translation—CN200910224585.4.
BPTO—Mar. 23, 2014—Office Action—PI0207770-1.
Genbank Accession No. AF032864.1—Da Silva—1997.
Genbank Accession No. M38570.1—UDAKA—1993.
EPO—Apr. 22, 2014—94(3) Communication—10 184 478.5.
EPO—Apr. 29, 2014—94(3) Communication—10 182 375.5.
EPO—May 13, 2014—94(3) Communication—09 171 688.6.
CIPO—May 28, 2014—Examiner's Requisition—CA 2, 438, 205.
Robertson—Applied and Environmental Microbiology (2004)—70-2429-2436.
BPTO—Sep. 9, 2014—Office Action—PI0207770-1.
AUIPO—Dec. 6, 2013—Examiner's First Report—2012238328 (D1530-5AUD3).
JPO—Dec. 20, 2012—Office Action—JP2011-022288.
SIPO—Oct. 12, 2012—Decision of Final Rejection & Translation—CN200910224585.4.
SIPO—Feb. 4, 2013—First Office Action and Translation—CN201210020583.5.
USPTO—Feb. 7, 2013—Office Action, 892, IDSs considered—U.S. Appl. No. 13/283,119.
EPO—Dec. 22, 2014—94(3) Communication—10 184 415.7.
Suzuki—J. Biol. Chem. (1989) 264-32-18933-18938.
Declerck—J. Biol. Chem. (1990) 265-26-15481-15488.
Horváthová—Gen. Physiol. Biophys. (2001) 20-7-32.
EPO—Jul. 27, 2015—94(3) Communication 10 184 478.5.
JPO—Jul. 4, 2016—Final Office Action—JP2014-159425.
94(3) Communication for EP09171688.6 dated Feb. 7, 2012.
94(3) Communication for EP09180956.6 dated Mar. 15, 2012.
94(3) Communication for EP09182375.5 dated Mar. 7, 2012.
94(3) Communication for EP10184415.7 dated May 2, 2012.
94(3) Communication for EP10184478.5 dated May 2, 2012.
Asada, (1995), Geneseq Accession No. AAR72603.
Atichokudomchai, (2006) Carbohydrate Polymers, 64:582-588.
Ausubel , (1990) Current Protocols in Molecular Biology, Chapters 1-3, 16 and Vectors-Appendix 5, John Wiley & Sons, New York, NY.
Birren, 2006, Uniprot Accession No. Q0C881.
Birren, 2006, Uniprot Accession No. Q0CPK9.
Bork, (2000) Genome Research, 10:348-400.
Broun, (1998) Science, 282:1315-1317.
Brown, (1999) Nature Genetics, 21:33-37.
Bult, (1996) Scienc, 273:1058-1073.
Callen, (2003), Geneseq Accession No. ABU03040, Alpha Amylase.
Callen, (2003), Geneseq Accession No. ABU03143.
Chica, (2005), Curr. Opin. Biotechnol., 4:378-384.
Decision of Final Rejection & Translation for CN200910224585.4 dated Oct. 12, 2012.
Decision of Rejection for CN200480012052.5 dated Aug. 15, 2011.
Devos, (2000), Proteins: Structure, Function, and Genetics, 41:98-107.
Dong, (1997) App. and Environ. Microbiol., 63(9):3569-3576.
Dong, (1999), Geneseq Accession No. AAW70536.
EBI Accession No. EAU29552, (2006), Aspergillus terreus NIH2624.
Examiner's First Report for AU2009222426 dated Jul. 4, 2011.
Examiner's First Report for AU2010246342 dated Jun. 8, 2011.
Examiner's Second Report for AU2004229313 dated Jul. 2, 2010.
Examiner's Second Report for AU2009222426 dated Aug. 22, 2011.
Examiner's Second Report for AU2010246342 dated Aug. 18, 2011.
Extended EP Search Report for EP 10182375.5 dated May 19, 2011.
Extended EP Search Report for EP10184415.7 dated Aug. 9, 2011.
Extended EP Search Report for EP10184478.5 dated Aug. 9, 2011.
Extended EP Search Report for EP12152656.0 dated May 29, 2012.
Extended EP Search Report for EP12152662.8 dated May 29, 2012.
Final Office Action for JP2006-506966 dated Feb. 7, 2011.
Final Office Action for U.S. Appl. No. 12/567,550 dated Jun. 10, 2011.
Final Office Action for U.S. Appl. No. 12/567,550 dated Nov. 16, 2011.
First Examination Report for Indian Application No. 3819/KOLNP/2008 dated Jun. 7, 2012.
First Office Action and Translation for CN200910224585.4 dated Aug. 23, 2011.
First Office Action and Translation for CN201210020583.5 dated Feb. 4, 2013.
Fox, (1991), Anal. Biochem., 195(1):93-96.
Genbank Accession No. CAB88152 (Apr. 19, 2000).
Giver, (1998), Current Opinion in Chemical Biology, 2:335-338.
Gray, (1986), Journal of Bacteriology, 166, 2:635-643.
Guo, (2004), Proc. Nat. Acad. Sci. USA, 101:9205-9210.
Herlemann, (2008), Genpept Accession No. ACC97877.
Hu, (1992), Journal of General Microbiology, 138:1647-1655.
Hulsmann, (2000), J. Bacteriol., 22:6292-6301.
Imanaka, (1997), Genbank Accession No. E13334.
Imanaka, (1997), Geneseq Accession No. AAW26131.
Jiang, 2003, EBI Accession No. ABB80178.
Jiang, (2003), Geneseq Accession No. ABB80181.
Jiang, (2003), Geneseq Accession No. ABQ80348.
Jiang, (2003), Geneseq Accession No. ABQ80354.
Jones, (2001), Genbank Accession No. AF017454.
Jones, (2001), Genpept Accession No. AAB87860.
Jones, (1999), Journal of Applied Microbiology, 86(1):93-107.
Jorgensen, (1997), Genbank Accession No. U96622.
Jorgensen, (1997), J. of Biol. Chem., 272(26):16335-16342.
Kim, (1996), FEMS Microbiol. Lett., 138:147-152.
Kim, (1996), Uniprot Accession No. Q52413.
Laderman, (1993), J. Biol. Chem., 268(32):24394-24401.
Lam, (1998), Geneseq Accession No. AAW34998.
Lanahan, (2006), EMBL Accession No. AR941925.
Lévêque, (2000), FEMS Microbiology Letters, 186:67-71.
Lévêque, (2000), Genbank Accession No. AF068255.
Lévêque, (2000), Geneseq Accession No. AAY53917.
Lin, (1995), Genbank Accession No. U22045.
Lin, (1997), Journal of Applied Microbiology, 82:325-334.
Lin, (1997), Letters in Applied Microbiology, 24:365-368.
Lin, (1996), Uniprot Accession No. Q59222.
Ma, (2002), Uniprot Accession No. Q8RNJ6.
Malhotra, (2000), Lett. Appl. Microbiol., 31:378-384.
Narang, (2001), Lett. Appl. Microbiol., 32:31-35.
NCBI Accession No. EAU34822, 2006, Aspergillus terreus NIH2624 glucoamylase precursor.
NCBI Accession No. Y13601, (1998), Streptomyces lividans.
Nigam, (1995), Enzyme Microbial Technology ,17:770-778.

(56) References Cited

OTHER PUBLICATIONS

Notice of Allowance for U.S. Appl. No. 10/547,957 dated Mar. 11, 2010.
O'Neill, (1990), Mol. Gen. Genet. 221:235-244.
Office Action for AU2006207843 dated Sep. 8, 2008.
Office Action for JP2006-506966 dated Jul. 12, 2010.
Office Action for JP2008-136876 dated Jun. 2, 2011.
Office Action for JP2011-022288 dated Dec. 20, 2012.
Office Action for CA2438205 dated Jan. 30, 2009.
Office Action for CA2438205 dated Jan. 9, 2012.
Office Action for CA2438205 dated Jan. 19, 2010.
Office Action for CA2438884 dated Feb. 25, 2011.
Office Action for CA2438884 dated Apr. 24, 2009.
Office Action for CA2515340 dated Nov. 14, 2011.
Office Action for EP02723192.7 dated Jul. 24, 2008.
Office Action for EP07869797.9 dated Dec. 13, 2011.
Office Action for EP09171688.6 dated Jan. 21, 2011.
Office Action for JP2002-568685 dated Jun. 1, 2009.
Office Action for JP2006-506966 dated Feb. 15, 2010.
Office Action for JP2010-132602 dated Aug. 16, 2012.
Office Action for JP2010-135846 dated May 14, 2012.
Office Action for U.S. Appl. No. 10/385,305 dated Jun. 25, 2008.
Office Action for U.S. Appl. No. 10/489,510 dated Nov. 13, 2008.
Office Action for U.S. Appl. No. 10/489,510 dated Oct. 16, 2007.
Office Action for U.S. Appl. No. 11/400,030 dated Feb. 9, 2009.
Office Action for U.S. Appl. No. 11/400,030 dated May 28, 2008.
Office Action for U.S. Appl. No. 11/621,534 dated May 13, 2009.
Office Action for U.S. Appl. No. 11/621,534 dated Sep. 17, 2009.
Office Action for U.S. Appl. No. 11/621,543 dated May 13, 2009.
Office Action for U.S. Appl. No. 12/822,413 dated Oct. 12, 2011.
Office Action for U.S. Appl. No. 13/283,119 dated Feb. 7, 2013.
Office Action U.S. Appl. No. 12/520,523 dated Apr. 30, 2012.
Partial EP Search Report for EP09171688.2 dated Feb. 26, 2010.
Partial EP Search Report for EP10 184 381 dated May 24, 2011.
Partial EP Search Report for EP10184415.7 dated Apr. 6, 2011.
Partial EP Search Report for EP10184478.5 dated Apr. 6, 2011.
Patent Abstracts of Japan (1997) (11) for JP09173077.
Richardson, (2002), Journal of Biological Chemistry, 277:26501-26507.
Robyt, (2009), "Enzymes and Their Action on Starch" in *Starch: Chemistry and Technology*, 3rd. ed.:237-292.
Rubingh, (1997), Current Opinion in Biotechnology, 8:417-422.
Search Report for EP09180956.6 dated Jul. 27, 2010.
Search Report for EP09180956.6 dated Nov. 29, 2010.
Search Report for PCT/US2003/33150 dated Dec. 20, 2004.
Search Report for PCT/US2004/07096 dated Jul. 16, 2008.
Seffernick, (2001), J. of Bacteriol., 183(8):2405-2410.
Sen, (2007), Appl. Biochem. Biotechnol, 2:212-223.
Supplementary EP Search Report for EP02706401 dated Sep. 6, 2004.
Supplementary EP Search Report for EP04718513.7 dated Oct. 5, 2009.
Supplementary EP Search Report for EP07869797.6 dated Sep. 29, 2009.
Supplementary Partial European Search Report for EP 02723192.7 dated Mar. 11, 2005.
Tachibana, (2000), Genbank Accession No. D83793.
Tachibana, (1996), J. Ferment. Bioeng, 82:224-232.
Tachibana, (2000), NCBI Accession No. BAA21130.
Uniprot Accession No. Q8JZK3, Alpha Amylase, Oct. 1, 2002.
Uniprot Database Accession No. Q4WIT7, Aspergillus fumigatus, Jul. 5, 2005.
UniProt, Swiss-Prot Protein Knowledgebase, Swiss Institute of Bioinformatics (SIB) et al., Glycosyl hydrolase families: classification and list of entries <http://www.expasy.ch/cgi-bin/lists?glycosid.txt> Release 55.5, Jun. 10, 2008.
Van De Loo, (1995), Proc. Natl. Acad. Sci. USA, 92(15):6743-6747.
Wang, (2000), UniprotKB Accession No. Q9P9LO.
Whisstock, (2003), Biophysics., 36(3):307-340.
Wishart, (1995), Journal of Biological Chemistry, 270:26782-26785.
Witkowski, (1999), Biochemistry, 38:11643-11650.
Wong, (2000), J. Agric. Food Chem., 48(10):4540-4543.

\* cited by examiner

Example Standard Curve of the Assay of Example 2

FIG. 7A

SEQ ID NO:1

```
atggccaagtactccgagctggaaaagggcggggtcataatgcaggcgttctactggacgtgc
cttcaggaggaatatggtgggacacaatacggcagaagataccggagtggtacgatgccggaat
ctccgcaatatggattccccccgcgagcaagggcatgggcggcgcctattcgatgggctacgac
ccctacgacttctttgacctcgtgagtacgacgcagaaggaacggtagagacgcgctttggct
ccaagcaggagctcgtgaacatgataaacaccgccacgcctatggcatgaaggtaatagccga
tatagtcatcaaccacgcgccggtgacctgaactgagtgaaccctcgtgaacgactatacc
tggaccgacttctcaaagtcgcgtcggtaaatacacggccaactacctcgacttccacccga
acgagctccatgcggctactggctctgggccagcaagtctacgcggctatcctcaggagcatcggc
ctggaccagtactggctctgggcgactacgtcaaggctatgtccctggtcgtcaaggactgctga
atcgatgcctggcgcttcgacctgagatactggagacaccaacgtcgacgctgttctcaactg
actgtggggaggctgggcgttggaagtctctttgacttcgccctctactacaagatgatgaggccttt
ggcatactcgagcggtgccaagtgccaagcgctcgtcctgccctcagaacgcaccgatataatctgaacaagtatcc
gacaacaaaacattccagccgtaaccttgtagcaaaaccacgaccacgatataatctgaacaagtatcc
acccgttcaaggccgtaacctttgtagcaaacccacgaccacgatataatctgaacaagtatcc
agcctacgcgttcatcctcacctacgagggccagccagcagatacatgagaacctcgccgaggaag
tggctcaacaaggataagtcaagaacctcatctggatacatgagaacctcgccgagaagca
ccgacatagtctactacgataacgatgaactcatcttcgtcaggaacggctacgggacaagcc
gggcttataacctacatcaacctaggctcgagcaaggccgaaggtgggtttatgtgccgaag
ttcgcggcgcgtgcatccacgagtatactggtaacctcgaggctggtagacaagtacgtct
actcaagcggctggtctatctcgaagctcgaagcttacgacccctgccaacggcagtatggcta
ctccgtgtggagctactgcggggtgggctga
```

FIG. 7B

```
SEQ ID NO:2
Met Ala Lys Tyr Ser Glu Leu Glu Lys Gly Gly Val Ile Met Gln Ala
Phe Tyr Asp Trp Asp Val Pro Ser Gly Gly Ile Trp Trp Asp Thr Ile Arg
Gln Lys Ile Pro Glu Trp Tyr Asp Ala Gly Ile Ser Ala Ile Trp Ile
Pro Pro Ala Ser Lys Gly Met Gly Gly Ala Tyr Ser Met Gly Tyr Asp
Pro Tyr Asp Phe Phe Asp Leu Gly Glu Glu Tyr Asp Gln Lys Gly Thr Val
Glu Thr Arg Phe Gly Ser Lys Gln Gly Leu Val Asn Met Ile Asn Thr
Ala His Ala Tyr Gly Met Lys Val Ile Ala Asp Ile Val Ile Asn His
Arg Ala Gly Gly Asp Leu Glu Trp Asn Pro Phe Val Asn Asp Tyr Thr
Trp Thr Asp Phe Ser Lys Val Ala Ser Gly Lys Tyr Thr Ala Asn Tyr
Leu Asp Phe His Pro Asn Glu Leu His Ala Gly Asp Ser Gly Thr Phe
Gly Gly Tyr Pro Asp Ile Cys His Asp Lys Ser Trp Asp Gln Tyr Trp
Leu Trp Ala Ser Gln Glu Ser Tyr Ala Ala Tyr Leu Arg Ser Ile Gly
Ile Asp Ala Trp Arg Phe Asp Tyr Val Lys Gly Tyr Ala Pro Trp Val
Val Lys Asp Trp Leu Asn Trp Trp Gly Gly Trp Ala Val Gly Glu Tyr
Trp Asp Thr Asn Val Asp Ala Leu Leu Asn Trp Ala Tyr Ser Ser Gly
Ala Lys Val Phe Asp Phe Ala Leu Tyr Tyr Lys Met Asp Glu Ala Phe
Asp Asn Lys Asn Ile Pro Ala Leu Val Ser Ala Leu Gln Asn Gly Gln
Thr Val Val Ser Arg Asp Pro Phe Lys Ala Val Thr Phe Val Ala Asn
His Asp Thr Asp Ile Ile Trp Asn Lys Tyr Pro Ala Tyr Ala Phe Ile
Leu Thr Tyr Glu Gly Gln Pro Thr Ile Phe Tyr Arg Asp Tyr Glu Glu
Trp Leu Asn Lys Asp Lys Leu Lys Asn Leu Ile Trp Ile His His Glu Asn
Leu Ala Gly Gly Ser Thr Asp Ile Val Tyr Tyr Asp Asn Asp Glu Leu
Ile Phe Val Arg Asn Gly Tyr Gly Pro Gly Leu Ile Thr Tyr
Ile Asn Leu Gly Ser Ser Lys Ala Gly Arg Trp Val Tyr Val Pro Lys
Phe Ala Gly Ala Cys Ile His Glu Tyr Thr Gly Asn Leu Gly Gly Trp
Val Asp Lys Tyr Val Tyr Ser Ser Gly Trp Val Tyr Leu Glu Ala Pro
Ala Tyr Asp Pro Ala Asn Gly Gln Tyr Gly Tyr Ser Val Trp Ser Tyr
Cys Gly Val Gly
```

FIG. 7C

SEQ ID NO:3
atgttcctgctcgcgttttgctcactgcctgctcgctgttctgcccaacaggacagcccgccaagg
ctgccgcaccgtttaacggcaccatgatgcagtatttgaatgtacttgccgatgatggcac
gttatgaccaaagtggccaatgaagcgcaacaacttatccagcctggcatcaccgctctttgg
ctgccgcccgcttacaaaggaacaagccgcagcgacgtaggtacgagtatacgacttgtatg
acctcggcgaattcaatcaaaaaggaccgtccgcacaaatacggaacaaaaagctcaatatct
tcaagccattcaagcgctgacggcacggaatgggtggacgccgtcgaagtgtacgccgatgtcgtgttcgaccat
aaaggcggcgctgacggcacgggtggacgccgtcgaagtcaatccgtccgaccgcaacc
aagaaatctcgggcacctatcaaatccaagcatgacgcgaaatttgattttcccggcggggcaa
cacctactccagcttttaagtgcgctgtgtaccattttgacggcgcttgattgggacgaaagccga
aaattgagccgcattacaaattccgcggcatcgtgccgaccttgatatgcatcccgaagtcgtgac
aaaacggaaactatgactacttaatgtatgccgaccttgatatgatcatgaacattgatggttccggcttgat
cgagctgaaaaactggggaatgtatgtcaacacaacgaacattgatggttccggcttgat
gccgtcaagcatatttcagttttttcctgattggttgtcgtatgtgcgttctcagactg
gcaagccgctattaccgtcggggaatattggagctatgacatcaacaagttgcacaattacat
tacgaaacagacgaacgatgtctttgttgtgatgccccgttacacaacaaatttataccgct
tccaaatcaggggcgcatttgatatgcgcacgttaatgacaccaatactctcatgaaagatcaac
cgacattggccgtcaccttcgttgataatcatgacacgaacccgccaagcgctgcagtcatg
ggtcgaccatggttcaaaccgttggctatttatgcgccagagcagggaaagggcaagagaagcaaaa
tgcgtcttttatggtgactattatgcgcgcaggattatgcttacgaaacgcaacatgattatcttgatca
tcgatccgctcctcatcgggtggacaaggaagggtcactgaaaaaccaggatccgggctggccgca
ctgatcaccgatgggccggaggaagcaaatggatgtactgttggcaaacaacacgctggaaaa
gtgttctatga

FIG. 7D

SEQ ID NO:4
atgaaacaacaaaaacggctttacgcccgattgctgacgctgtatttgcgctcatcttcttgc
tgcctcattctgcagcagcggcggccaacattggaagcggcaaatcttaatggacgctgatgcagtatttgaatggta
catgcccaatgacggccaacattggaagcgcttgcaaaacgactcggcatatttggctgaacac
ggtattactgccgtctggattccccgcatataaggaacgagccaagcggatgtggctacg
gtgcttacgacctttatgattaggggagttcatcaaaaggacggttcgacaaagtacgg
cacaaaaggagagctgcaatctgcgatcaaagcggcgctgatcaaagtcttcattcccgcgacattaacgtttacggg
gatgtggtcatcaaccacacaaaggcggcgctaattcaggagaacaccgaattaaagctggacacatttca
atcccgctgaccgcaaccgcgtaattcaagcgattttaaatgcattggtaccatttttgacggaacc
ttttccggggcgcggcagcacataacgctgaaccgcatctatatagtttcaaggaaaggcttgggattggg
gattgggacgagtcccgaaacgcgcaactatgattaagagatgggcacttggtatgccaatgaactgcaattggacggt
aagttttccaatgaaaacgcaactatgattaagagatgggcactatttctttttgcggattgggttaatcatgtca
tgatgtcgcagcagaaattaagagacacattaaattttctttttgcggattgggttaatcatgtca
ttccgtcttgatgctgtcaaacacattaaattttctttttgcggattgggttaatcatgtca
gggaaaaaacgtatttgaacaaaacaaatgtttacggtagctcattcagtgtttgacgtgccgcttcattatcag
ttccatgctgcatcgacacaggaggcggttacattgtcgataaccatgatacacagccgggcaatc
tttccaagcatccgttgaaagcggttacattgtttaagccgcttgcttctttaaaacagcttctcacaaggaa
gcttgagtcgactgtccagttttctcaggggatatgtacgggacgaaagagactcccagcgcgaaa
tctgataccctcagtttctcaggggatatgtacgggacgatctttaaaagcgagaaaacagtatgcgtacggagc
ttcctgccttgaaacacaaaattgaaccgatcttaaaagcgctgacaaggggcacagctcgtt
acagcatgattattcgaccaccatgcatttaaaagcgctgacaaggggcaaagcgacagctcgtt
gcaaattcaggtttggcgcgcattaataacagacgacgatgcatgatcatgcatgcgaactgctgtcg
gcccgcaaaacgccggtgagacatgacattaacgagacattaccggagacagttcgtacggacagtgtcat
caattcggaaggctggggagagtttcacgtaaacgcgggtcggtttcaatttatgttcaaaga
tag

FIG. 7E

```
SEQ ID NO:5
gtggtgcacatgaagttgaagtacctgccttagttttgttggctgtggcttcgataggcctac
tctcgactggttgggtgctgccaagtactccgaactcgaagagggcgtgttataatgcaggc
cttctactgggatgttcccggaggggaatctggtgggacaccataagacagaaaatcccggag
tggtacgacgctgaatctcggcgatatggattcctccagctagcaaaggatgggcggtggtt
attccatgggctacgatccctacgattcttttgacctcggcgagtactatcagaaggaacagt
tgagacgcgcttcggctcaaaggaggaactggtgaacatgataaacaccgcacactcctatggc
ataaaggtgatagcggacatagtcataaaccaccgcgccggtggagacctttgagtggaacccct
ttgtaaacaactatacttggacagacttctccaaggtcgcctccgtaaatacacggccaacta
ccttgacttccaccaccaaacgaggtcaagtgctgcgatgaggtacatttgtgactttccgac
atcgccacgagaagagctggatcagtacgtactagagctctacgccgcat
atctccggagcataggatcgatgcatggcgtttcgactacgtcaaaggttacggagcgtgggt
tgttaatgactggctcagctgtgtgggaggctgggcgttggagagtacttgggacacgaacgtt
gatgcactccttaactggacataccgacagcggtgccaagtctcttgacttccccgctctactaca
agatgacgaagcctttgacaacaccaacatcccccgctttggttttacgccctccagaacggagg
aacagtcgtttcccgcgatccctcaaggcagtaactttcgttgccaaccacgatacagatata
atctggaacaagtatccggcttatcgcgttcatcctacctatgagggacagcctgttatattt
accgcgactacgaggagtggctcaacaaggataagcttaacaaccttatctgatacacgagca
ccttgccgaggaggcaagccgggcctcataacctccgaaaacgactgggccgagcgct
ggctacgggagcaagcagcaaaaggtttgccggctacacaatccatgaatacacaggcaatctcggtgg
gggtgaacgtcggctcaaagtttgccggctacgatggtgggtaaactgacggcacctcctcatgatccca
ctgggttgacaggtgggtcagtacgatctgagctacgcaggcgtcggatga
gccaacggatattacggctactcagtctgagctacgcaggcgtcggatga
```

FIG. 7F

```
SEQ ID NO:6
atgaagaagtttgtcgccctgttcataaccatgttttcgtagtgagcatggcagtcgttgcac
agccagtcagccgccaaagtattccgagctcgaagaaggcggcgttataatgcaggccttcta
ctggacgtcccagtgaggaatctgtggagacaccatcaggagcaagataccgagtggtac
gaggcggaatatccgccatttgattccgccagccagcaagggatgagcggcggttactcga
tgggctacgatccctacgatttcttgacctcggcgagtacaaccagaaggaaccatcgaaac
gcgctttggctctaaacaggagctcatcaatatgataaacacggcccatgcctacggcataaag
gtcatagcggacatcgtcataaaccaccgcgcaggcggagacctcgagtggaacccgttcgttg
gggactacacctgacggagtcaagtgctgtgacgaggcacatttgaggcttccagacatagcc
cttccaccccaacgagctgggaccagcactggctctgcttgactacgtgaaggctacgagcgcctacctaa
cacgagaagagctggcgttgatgcctggccgcgccctgggcgctgggctactggacacgttgatgca
ggagcatcggcgttgatgcctggccgcgccctgggcgctgggctactggagagcgtgggtcgtcaa
ggactggctcaactggtgggcgctgggcgcgccaaggtcttcgtctgtctcgtttgatgca
ctcctcaactggcctactcgagcggcgcgccaagcgctcgtctctgccctcagaacgccagactgt
atgaggcctttgacaacaaaaacattccagcgctaaccttgtagcaaaccacgacacgatataatctgg
tgtctcccgcgaccgttcaaggccgtaaccttgtagcaaaccacgacaccgtatattctaccgcg
aacaagtaccttgcttatgcttcatcctcacctacgaaggccagcccgtcatattctaccgcg
actacgaggagtgctcaacaaggacaggttgaacaacctcatatgatacacgaccacctcgc
aggtgaagcacgagcatagtctactacgacagcgacgagatgatcttcgtgaggaacggctat
ggaagcaagctggcttatactacattacatcaacctcggctcgagcaaggttgaaggtgggttt
atgtgccgaagttcgcgggcgcgtgcatccacgagtatactggtaacctcggaggctgggtaga
caagtacgtctactcaaggcggctggttctatctcgaagctccagcttacgaccctgccaacggg
cagtatggctactccgtgtggagctattgcggtgttgggtga
```

FIG. 7G

```
SEQ ID NO:7
Met Phe Leu Leu Ala Phe Leu Leu Thr Ala Ser Leu Phe Cys Pro Thr
Gly Gln Pro Ala Lys Ala Ala Pro Asp Phe Asn Gly Leu Trp Met Gln
Tyr Phe Glu Trp Tyr Leu Pro Asp Asp Gly Thr Leu Trp Thr Lys Val
Ala Asn Glu Ala Asn Leu Ser Ser Leu Gly Ile Thr Ala Leu Leu Trp
Leu Pro Pro Ala Tyr Lys Gly Thr Ser Arg Ser Asp Val Gly Tyr Gly
Val Tyr Asp Leu Tyr Asp Leu Gly Glu Phe Asn Gln Lys Gly Thr Val
Arg Thr Lys Tyr Gly Thr Lys Ala Gln Tyr Leu Gln Ala Ile Gln Ala
Ala His Ala Ala Gly Met Gln Val Tyr Ala Asp Val Val Phe Asp His
Lys Gly Gly Ala Asp Gly Thr Met Gln Val Thr Ala Val Glu Val Asn
Pro Ser Asp Arg Asn Gln Glu Thr Ser Gly Thr Tyr Gln Ile Gln Ala
Trp Thr Lys Phe Asp Phe Pro Gly Arg Gly Asn Thr Tyr Ser Ser Phe
Lys Trp Arg Trp Tyr His Phe Asp Gly Val Asp Trp Asp Glu Ser Arg
Lys Leu Ser Arg Ile Tyr Lys Phe Arg Gly Ile Gly Lys Ala Trp Asp
Trp Glu Val Asp Thr Glu Asn Gly Asn Tyr Asp Tyr Leu Met Tyr Ala
Asp Leu Asp Met Asp His Pro Glu Val Val Thr Glu Leu Lys Asn Trp
Gly Lys Trp Tyr Val Asn Thr Thr Asn Ile Asp Gly Phe Arg Leu Asp
Ala Val Lys His Ile Lys Phe Ser Phe Phe Pro Asp Trp Leu Ser Tyr
Val Arg Ser Gln Thr Gly Lys Pro Leu Phe Thr Val Gly Glu Tyr Trp
Ser Tyr Asp Ile Asn Lys Leu His Asn Tyr Ile Thr Lys Thr Asp Gly
Thr Met Ser Leu Phe Asp Ala Pro Leu His Asn Lys Phe Tyr Thr Ala
Ser Lys Ser Gly Gly Ala Phe Asp Met Arg Thr Leu Met Thr Asn Thr
Leu Met Lys Asp Gln Pro Thr Leu Ala Val Thr Phe Val Asp Asn His
Asp Thr Glu Pro Gly Gln Ala Leu Gln Ser Trp Val Asp Pro Trp Phe
Lys Pro Leu Ala Tyr Ala Phe Ile Leu Thr Arg Gln Glu Gly Tyr Pro
Cys Val Phe Tyr Gly Asp Tyr Tyr Gly Ile Pro Gln Tyr Asn Ile Pro
Ser Leu Lys Ser Lys Ile Asp Pro Leu Leu Ile Ala Arg Arg Asp Tyr
Ala Tyr Gly Thr Gln His Asp Tyr Leu Asp His Ser Asp Ile Ile Gly
Trp Thr Arg Glu Gly Val Thr Glu Lys Pro Gly Ser Gly Leu Ala Ala
Leu Ile Thr Asp Gly Pro Gly Gly Ser Lys Trp Met Tyr Cys Trp Gln
Thr Thr Arg Trp Lys Ser Val Leu
```

FIG. 7H

```
SEQ ID NO:8
Met Lys Gln Gln Lys Arg Leu Tyr Ala Arg Leu Leu Thr Leu Leu Phe
Ala Leu Ile Phe Leu Leu Pro His Ser Ala Ala Ala Ala Asn Asp Leu
Asn Gly Thr Leu Met Gln Tyr Phe Glu Trp Tyr Met Pro Asn Asp Gly
Gln His Trp Lys Arg Leu Gln Asn Asp Ser Ala Tyr Leu Ala Glu His
Gly Ile Thr Ala Val Trp Ile Pro Pro Ala Tyr Lys Gly Thr Ser Gln
Ala Asp Val Gly Tyr Gly Ala Tyr Asp Leu Tyr Asp Leu Gly Glu Phe
His Gln Lys Gly Thr Val Arg Thr Lys Tyr Gly Thr Lys Gly Glu Leu
Gln Ser Ala Ile Lys Ser Leu His Ser Arg Asp Ile Asn Val Tyr Gly
Asp Val Val Ile Asn His Lys Gly Gly Ala Asp Ala Thr Glu Asp Val
Thr Ala Val Glu Val Asp Pro Ala Asp Arg Asn Arg Val Ile Ser Gly
Glu His Arg Ile Lys Ala Trp Thr His Phe His Phe Pro Gly Arg Gly
Ser Thr Tyr Ser Asp Phe Lys Trp His Trp Tyr His Phe Asp Gly Thr
Asp Trp Asp Glu Ser Arg Lys Leu Asn Arg Ile Tyr Lys Phe Gln Gly
Lys Ala Trp Asp Trp Glu Val Ser Asn Glu Asn Gly Asn Tyr Asp Tyr
Leu Met Tyr Ala Asp Ile Asp Tyr Asp His Pro Asp Val Ala Ala Glu
Ile Lys Arg Trp Gly Thr Trp Tyr Ala Asn Glu Leu Gln Leu Asp Gly
Phe Arg Leu Asp Ala Val Lys His Ile Lys Phe Ser Phe Leu Arg Asp
Trp Val Asn His Val Arg Glu Lys Thr Gly Lys Glu Met Phe Thr Val
Ala Glu Tyr Trp Gln Asn Asp Leu Gly Ala Leu Glu Asn Tyr Leu Asn
Lys Thr Asn Phe Asn His Ser Val Phe Asp Val Pro Leu His Tyr Gln
Phe His Ala Ala Ser Thr Gln Gly Gly Gly Tyr Asp Met Arg Lys Leu
Leu Asn Gly Thr Val Val Ser Lys His Pro Leu Lys Ala Val Thr Phe
Val Asp Asn His Asp Thr Gln Pro Gly Gln Ser Leu Glu Ser Thr Val
Gln Thr Trp Phe Lys Pro Leu Ala Tyr Ala Phe Ile Leu Thr Arg Glu
Ser Gly Tyr Pro Gln Val Phe Tyr Gly Asp Met Tyr Gly Thr Lys Gly
Asp Ser Gln Arg Glu Ile Pro Ala Leu Lys His Lys Ile Glu Pro Ile
Leu Lys Ala Arg Lys Gln Tyr Ala Tyr Gly Ala Gln His Asp Tyr Phe
Asp His His Asp Ile Val Gly Trp Thr Arg Glu Gly Asp Ser Ser Val
Ala Asn Ser Gly Leu Ala Ala Leu Ile Thr Asp Gly Pro Gly Gly Ala
Lys Arg Met Tyr Val Gly Arg Gln Asn Ala Gly Glu Thr Trp His Asp
Ile Thr Gly Asn Arg Ser Glu Pro Val Val Ile Asn Ser Glu Gly Trp
Gly Glu Phe His Val Asn Gly Gly Ser Val Ser Ile Tyr Val Gln Arg
```

```
SEQ ID NO:9
Val Val His Met Lys Leu Tyr Leu Ala Leu Leu Ala Val
Ala Ser Ile Gly Leu Leu Ser Thr Pro Val Ala Lys Tyr Ser
Glu Leu Glu Glu Gly Val Val Ile Met Gln Ala Phe Tyr Asp Val
Pro Gly Gly Ile Gly Gly Ile Met Asp Thr Ile Arg Gln Lys Ile Pro Glu
Trp Tyr Asp Ala Gly Ile Ala Thr Ile Ile Arg Pro Ala Ser Lys
Gly Met Gly Gly Tyr Ser Met Gly Met Gly Tyr Ile Asp Pro Ala Phe Phe
Asp Leu Gly Glu Tyr Tyr Gln Ser Gly Tyr Asp Pro Tyr Arg Phe Gly
Ser Lys Gly Glu Leu Val Lys Met Ile Thr Val Gly Leu Thr Ala His Ser Tyr Gly Asp
Ile Lys Val Ile Ala Asn Met Ile Ala Leu Val Arg Asn Ser Ala Val Gly Phe Ser
Leu Glu Trp Asn Pro Phe Val Ala Asn Tyr Thr Pro Phe Gly Thr Thr Asp Phe His Pro
Lys Val Ala Ser Gly Leu Lys Tyr Thr Ala Asn Tyr Leu Asp Phe Gly Leu Asp Pro
Asn Glu Val Lys Cys Asp Gly Thr Phe Gly Asp Phe Asp Ala Asn
Ile Ala His Glu Lys Ser Trp Asp Gln Tyr Ile Trp Leu Asp Ala Trp Ser Arg
Glu Ser Tyr Ala Ala Ser Trp Leu Arg Ser Ile Gly Val Ala Asn Asp Trp Asn Val
Phe Asp Tyr Val Lys Gly Trp Ala Val Gly Ala Trp Tyr Asp Thr Phe Asp
Ser Trp Pro Gly Tyr Asp Tyr Ala Gly Ser Gly Ala Phe Asp Leu Lys Val Phe Ala Ser
Asp Ala Leu Asn Trp Leu Ala Phe Asp Ala Tyr Asn Trp Val Asn Thr Ile
Phe Pro Tyr Tyr Tyr Lys Met Gln Ile Ala Asp Thr Thr Tyr Val Ala Ser Asp
Pro Ala Val Tyr Ala Asp Gln Asn Gly Asn His Leu Glu Asn Val Thr Asp Arg Glu Glu
Asp Pro Phe Lys Ala Thr Phe Val Ala Pro Tyr Phe Lys Ile Tyr Asp Tyr Gly Glu Lys
Ile Trp Asn Lys Tyr Pro Asp Tyr Asn Ile Glu Glu Thr Leu Ile Asn Asp Gly
Gln Pro Val Ile Phe Arg Ile Leu Lys His Leu Phe Leu Asp Asn Lys Asp
Lys Leu Asn Asn Trp Asp Leu Asn Val His Ser Gly Asn Phe Leu Gly Ser
Thr Ile Leu Leu Tyr Pro Leu Leu Thr Ile Lys Leu Asn Thr Leu Phe Met Arg Asn
Gly Tyr Gly Ser Lys Gly Ala Lys Val Gly Ser Val Phe Leu Ala Gly
Asp Trp Ala Glu Arg Trp Thr Leu Asn Gly Lys Trp Pro Val Ala Ala Tyr Asp
Thr Ile His Glu Tyr Arg Thr Tyr Phe Lys Asp Leu Arg Arg Arg Ala
Val Gln Tyr Asp Gly Thr Val Asn Val Lys Asp Trp Tyr Met Asp Gln Arg Gln
Ala Asn Gly Tyr Tyr Val Arg Trp Ser Leu Thr Pro Ser Tyr Ala Gly Val Gly

FIG. 7I
```

SEQ ID NO:10
Met Lys Lys Phe Val Ala Leu Phe Ile Thr Met Phe Val Val Ser
Met Ala Val Val Ala Gln Pro Ala Ser Ala Ala Lys Tyr Ser Glu Leu
Glu Glu Gly Gly Val Ile Met Gln Ala Phe Tyr Trp Asp Val Pro Gly
Gly Gly Ile Trp Trp Asp Thr Ile Arg Ser Lys Ile Pro Glu Trp Tyr
Glu Ala Gly Ile Ser Ala Ile Trp Ile Pro Pro Ala Ser Lys Gly Met
Ser Gly Gly Tyr Ser Met Gly Tyr Asp Pro Tyr Asp Phe Phe Asp Leu
Gly Glu Tyr Asn Gln Lys Gly Thr Ile Glu Thr Arg Phe Gly Ser Lys
Gln Glu Leu Ile Asn Met Ile Asn Thr Ala His Ala Tyr Gly Ile Lys
Val Ile Ala Asp Ile Val Ile Asn His Arg Ala Gly Gly Asp Leu Glu
Trp Asn Pro Phe Val Gly Asp Tyr Thr Trp Thr Asp Phe Ser Lys Val
Ala Ser Gly Lys Tyr Thr Ala Asn Tyr Leu Asp Phe His Pro Asn Glu
Val Lys Cys Cys Asp Glu Gly Thr Phe Gly Gly Phe Pro Asp Ile Ala
His Glu Lys Ser Trp Asp Gln Trp Leu Val Trp Leu Ala Ser Glu Ser
Tyr Ala Ala Tyr Leu Arg Ser Ile Gly Val Val Asp Ala Trp Arg Phe Asp
Tyr Val Lys Gly Tyr Gly Ala Val Gly Glu Trp Tyr Asp Thr Asn Val Asp Ala
Trp Gly Gly Trp Ala Tyr Ser Ser Glu Ala Lys Val Phe Asp Pro Phe Pro
Leu Leu Asn Trp Ala Tyr Ser Glu Gly Ala Phe Asn Lys Val Ile Pro Ala
Leu Tyr Tyr Lys Met Asp Phe Gln Thr Val Leu Asn Thr Asp Tyr Asn Pro Tyr Gln Ile Leu
Leu Val Ser Ala Leu Gln Asn Gly Met Ile Phe Val Glu Asn His Asp Ser Ser Leu Asp Arg Thr
Phe Lys Ala Val Thr Phe Phe Ala Phe Ile Phe Thr Leu Pro Gly Ser Ala
Asn Lys Tyr Leu Ala Tyr Ala Phe Ile Leu Thr Tyr Glu Gly Gly Ala Asp Ala Gly
Val Ile Phe Tyr Arg Asp Tyr Glu Glu Leu Pro Lys Leu Asn Leu Ala Asp Arg Leu
Asn Asn Leu Ile Trp Ile His Asp Ile Leu Asn Ala Gly Gly Ser Thr Ser
Ile Val Tyr Tyr Asp Ser Asp Glu Met Ile Phe Thr Arg Asn Gly Tyr
Gly Ser Lys Pro Gly Leu Ile Thr Tyr Ile Ser Asn Leu Gly Ser Ser Lys Cys Ile His
Val Gly Arg Trp Val Val Tyr Arg Gly Pro Lys Ser Phe Ala Gly Ala Ala Tyr Tyr Ser
Glu Tyr Thr Gly Asn Leu Gly Gly Trp Val Asp Lys Tyr Val Tyr Ser
Ser Gly Trp Val Tyr Leu Gly Ala Pro Ala Tyr Arg Asp Pro Ala Asn Gly
Gln Tyr Gly Tyr Ser Val Trp Cys Tyr Tyr Cys Gly Val Gly Gly

FIG. 7K

SEQ ID NO:66
atggctctggaagagggcgggctcataatgcaggccttctactggacgtccccatgggaggaa
tctggtgggacacgatagcccagaagataccggactggcaagcgccggatttcggcgatatg
gatccctcccgagcaaggtatgagcggcggctattcgatgggctacgaccctacgattat
tttgacctcggtgagtactaccagaagaggaacggtgaaacgaggttcggctcaaagcaggagc
tcataaacatgataaacacccgcccacgcctatgggcatgaaggtaatagccgatatagtcatcaa
ccaccgcgccggcggtgacctggagtggaaccccttcgtgaacgactataccctgaccgacttc
tcaaaggtcgcgtcgggtaaatacacggccaactacctcgacttccaccgaacgagctccatg
cgggcgattccgggaacatttggaggctatgctccctgggtcgtcaagactggcatcggtgctgg
ctggctctgggactacgtcaaggctcaaggctatgctccctgggtcgtcaagactggctgatgcctgg
cgcttcgactacgtcaaggctacgtcaaggctatgctccctgggtcgtcgacgctgttctcaactgggcatactcgag
gctgggcggttggagagtactggacaccaacgtcgacgtcgtgttctcaactgggcataacaacaac
cggtgccaaggtctttgacttcgccctctactacaagatgacgaggccttcagccgcgacccgttcaagg
attcccgccctggtggacgcgcctcagatacggtcagacagtggtcagccgcgaccegttcaagg
ctgtgacgttttgtagccaaccacgagccgacataaccgacataatctggaacaagtatccagcctacgcgtt
catcctcacctacgagggccagccagccgacaatacatgacaacctcgcgggaggagcaagccggactgataac
gataagctcaagaacgacgagctgatattcgtgagaaacggctacgaagcaagccggactgataac
actacgacaacctcgcctcaagccggcaatctcggcgcgtcggaacaagtgggttacgttcgaagtgtcg
atacatcaacctcgcctcaagccggcaatctcggcgcgtcggaacaagtgggttgactcaagcggct
tgcatacacgagtacaccggatacatctgataccaagccggaagcggttcacgttcgaagcggtgggtgactcaagcggct
gggtctacctcgaggctcctgcccacgacccggccaacggccagtacggctactccgtctggag
ctactgcggtgttgggtga SEQ ID NO:67
Met Ala Leu Glu Glu Gly Gly Leu Ile Met Gln Ala Phe Tyr Trp Asp
Val Pro Met Gly Gly Ile Trp Trp Asp Thr Ile Ala Gln Lys Ile Pro
Asp Trp Ala Ser Ala Gly Ile Ser Ala Ile Trp Ile Pro Pro Ala Ser
Lys Gly Met Ser Gly Gly Tyr Ser Met Gly Tyr Asp Pro Tyr Asp Tyr
Phe Asp Leu Gly Glu Tyr Tyr Gln Lys Gly Thr Val Glu Thr Arg Phe
Gly Ser Lys Gln Glu Leu Ile Asn Met Ile Asn Thr Ala His Ala Tyr
Gly Met Lys Val Ile Ala Asp Ile Val Ile Asn His Arg Ala Gly Gly
Asp Leu Glu Trp Asn Pro Phe Val Asn Asp Tyr Thr Trp Thr Asp Phe
Ser Lys Val Ala Ser Gly Lys Tyr Thr Ala Asn Tyr Leu Asp Phe His
Pro Asn Glu Leu His Ala Gly Asp Ser Gly Thr Phe Gly Gly Tyr Pro
Asp Ile Cys His Asp Lys Ser Trp Asp Gln Tyr Trp Leu Trp Ala Ser
Gln Glu Ser Tyr Ala Ala Tyr Leu Arg Ser Ile Gly Ile Asp Ala Trp
Arg Phe Asp Tyr Val Lys Gly Tyr Ala Pro Trp Val Val Lys Asp Trp
Leu Asn Trp Trp Gly Gly Trp Ala Val Gly Glu Tyr Trp Asp Thr Asn
Val Asp Ala Val Leu Asn Trp Ser Tyr Ser Ser Gly Ala Lys Val Phe
Asp Phe Ala Leu Tyr Tyr Lys Met Asp Glu Ala Phe Asp Asn Asn Asn
Ile Pro Ala Leu Val Asp Ala Leu Arg Tyr Gly Gln Thr Val Val Ser
Arg Asp Pro Phe Lys Ala Val Thr Phe Val Ala Asn His Asp Thr Asp
Ile Ile Trp Asn Lys Tyr Pro Ala Tyr Ala Phe Ile Leu Thr Tyr Glu
Gly Gln Pro Thr Ile Phe Tyr Arg Asp Tyr Glu Glu Trp Leu Asn Lys
Asp Lys Leu Lys Asn Leu Ile Trp Ile His Asp Asn Leu Ala Gly Gly
Ser Thr Asp Val Tyr Tyr Asp Asn Asp Glu Leu Ile Phe Val Arg
Asn Gly Tyr Gly Ser Lys Pro Gly Leu Ile Thr Tyr Ile Asn Leu Ala
Ser Ser Lys Ala Gly Arg Trp Val Tyr Val Pro Lys Phe Ala Gly Ser
Cys Ile His Glu Tyr Thr Gly Asn Leu Gly Gly Trp Val Asp Lys Trp
Val Asp Ser Ser Gly Trp Val Tyr Leu Glu Ala Pro Ala His Asp Pro
Ala Asn Gly Gln Gly Tyr Gly Tyr Ser Val Trp Ser Tyr Cys Gly Val Gly

SEQ ID NO:68
atgaagcctgcgaaactcctcgtctttgtgctcgtagtctctatcctcgcggggctctacgccc
agcccgcgggggcggccaagtacctggagctcgaagagggcggcgtcataatgcaggcgttcta
ctggacgtgccttcaggaggaatatggtgggacacaatacggcagaagataccggagtggtac
gatgccgaatctccgcaatatggattccccccgcgagcaaggcatggcgcgcctattcga
tgggctacgaccccctacgacttcttgacctcggtgagtacgaccagaaggaacggtagagac
gcgctttggctccaagcaggagctcgtgaacatgataaacaccgcccacgcctacggcatcaag
gtcatcgcagacatagtaatcaaccacgcgcgaaggtcgcttccggcaagtacacggtgaaccccttcgtca
atgactacacctgacggacttctgcagtcaagtgctgcgacgaggttcccgdtgagggttcccgacatagcc
cttccaccccaacgagctggaccagtctctggcgagcaacgagagctacgccgcctacctca
cacgagaagagctggctgttgacgcttcgactacgtcaaggctacgagagctacggagtgggtcgtcaa
ggagcatcggcgtgactggctggggaggctgagctgccgtcggggagtactgggacacaaacgttgatgca
ggactggctgactggtgggaggcctgatgcaaaagtcttcgacttcccgctctactacaagatgg
ctgctcaactgggcctactgcgagcgatgcaaaagtcttcgacttcccgctctactacaagatgg
acgcggcctttgacaacaagaacattcccgcactcgtcgaggccctcaagacacggggcacagt
cgtcagccgcgacgacccgttaaggccgccttcatcctcacctacgagggccagcgacgatattctaccgcg
aacaagtaccggcctacgcctacgccttcatcctcacctacgagggccagcgacgatattctaccgcg
actacgaggagtggctcaacaaggacaggctcaagaacctcatctgatacacgaccacctcgc
cggtggaagcaccgacatagtctataacctcaacctaggctcgagcaaggccggaggtgggtct
ggggacaagccggggcttataaccctacatcaacctaggctcgagcaaggccggaggtgggtct
acgttccgaagttcgcgggagcgtgcatccacggagtacaccggccctgcccacgacccggccaacggc
caagtgggtgactcaagcgggtgggtgtacctcgaggcgtacctcgaggccctgcccacgacccggccaacggc
tattacggctactccgtctgagctactgcgggtgtgggctga SEQ ID NO:69
Met Lys Pro Ala Lys Leu Leu Val Phe Val Leu Val Val Ser Ile Leu
Ala Gly Leu Tyr Ala Gln Pro Ala Gly Ala Phe Tyr Trp Leu Glu Leu
Glu Glu Gly Gly Val Ile Met Gln Ala Phe Tyr Asp Val Pro Ser
Gly Gly Ile Trp Trp Asp Thr Ile Arg Gln Lys Ile Pro Glu Trp Tyr
Asp Ala Gly Ile Ser Ala Ile Trp Ile Pro Pro Ala Ser Lys Gly Met
Gly Gly Ala Tyr Ser Met Gly Tyr Asp Pro Tyr Asp Phe Phe Asp Leu
Gly Glu Tyr Asp Gln Lys Gly Thr Val Glu Thr Arg Phe Gly Ser Lys
Gln Glu Leu Val Asn Met Ile Asn Thr Ala His Ala Tyr Gly Ile Lys
Val Ile Ala Asp Ile Val Ile Asn His Arg Ala Gly Gly Asp Leu Glu
Trp Asn Pro Phe Val Asn Asp Tyr Thr Trp Thr Asp Phe Ser Lys Val
Ala Ser Gly Lys Tyr Thr Ala Asn Tyr Leu Asp Phe His Pro Asn Glu
Val Lys Cys Cys Asp Glu Gly Thr Phe Gly Gly Phe Pro Asp Ile Ala
His Glu Lys Ser Trp Asp Gln Tyr Trp Leu Trp Ala Ser Asn Glu Ser
Tyr Ala Ala Tyr Leu Arg Ser Ile Gly Val Asp Ala Trp Arg Phe Asp
Tyr Val Lys Gly Tyr Gly Ala Trp Val Val Lys Asp Trp Leu Asp Trp
Trp Gly Gly Trp Ala Val Gly Glu Tyr Trp Asp Thr Asn Val Asp Ala
Leu Leu Asn Trp Ala Tyr Ser Ser Asp Ala Lys Val Phe Asp Phe Pro
Leu Tyr Tyr Lys Met Asp Ala Ala Phe Asp Asn Lys Asn Ile Pro Ala
Leu Val Glu Ala Leu Lys Asn Gly Gly Thr Val Val Ser Arg Asp Pro
Phe Lys Ala Val Thr Phe Val Ala Asn His Asp Thr Asp Ile Ile Trp
Asn Lys Tyr Pro Ala Tyr Ala Phe Ile Leu Thr Tyr Glu Gly Gln Pro
Thr Ile Phe Tyr Arg Asp Tyr Glu Glu Trp Leu Asn Lys Asp Arg Leu
Lys Asn Leu Ile Trp Ile His Asp Asn Leu Ala Gly Gly Ser Thr Asp
Ile Val Tyr Asp Asn Asn Asp Glu Leu Ile Phe Val Arg Asn Gly Tyr
Gly Asp Lys Pro Gly Leu Leu Thr Tyr Ile Asn Leu Gly Ser Ser Lys
Ala Gly Arg Trp Val Tyr Val Pro Lys Phe Ala Gly Ala Cys Ile His
Glu Tyr Thr Gly Asn Leu Gly Gly Trp Val Asp Lys Trp Val Asp Ser
Ser Gly Trp Val Tyr Leu Glu Ala Pro Ala His Asp Pro Ala Asn Gly
Tyr Tyr Gly Tyr Ser Val Trp Ser Tyr Cys Gly Val Gly

AMYLASES, NUCLEIC ACIDS ENCODING THEM AND METHOD OF PRODUCING AN OIL

SEQUENCE LISTING

This application is being filed electronically via the USPTO EFS-WEB server, as authorized and set forth in MPEP § 502.05 and this electronic filing includes an electronically submitted sequence listing; the entire content of this sequence listing is hereby incorporated by reference into the specification of this application. The sequence listing is identified on the electronically filed ASCII (.txt) text file as follows:

| File Name | Date of Creation | Size |
|---|---|---|
| 160996US05_sequencelisting.txt | Jun. 5, 2017 | 47.4 KB (48,589 bytes) |

TECHNICAL FIELD

This invention relates to molecular and cellular biology and biochemistry. In one aspect, the invention is directed to polypeptides having an amylase activity, e.g., alpha amylase activity, polynucleotides encoding the polypeptides, and methods for making and using these polynucleotides and polypeptides. In one aspect, the polypeptides of the invention can be used as amylases, for example, alpha amylases, to catalyze the hydrolysis of starch into sugars.

BACKGROUND

Starch is a complex carbohydrate often found in the human diet. The structure of starch is glucose polymers linked by $\alpha$-1,4 and $\alpha$-1,6 glucosidic bonds. Amylase is an enzyme that catalyzes the hydrolysis of starches into sugars. Amylases hydrolyze internal $\beta$-1,4-glucosidic linkages in starch, largely at random, to produce smaller molecular weight malto-dextrins. The breakdown of starch is important in the digestive system and commercially. Amylases are of considerable commercial value, being used in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper; and in animal feed.

Amylases are produced by a wide variety of microorganisms including *Bacillus* and *Aspergillus*, with most commercial amylases being produced from bacterial sources such as *Bacillus licheniformis, Bacillus amyloliquefaciens, Bacillus subtilis*, or *Bacillus stearothermophilus*. In recent years, the enzymes in commercial use have been those from *Bacillus licheniformis* because of their heat stability and performance, at least at neutral and mildly alkaline pHs.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by amylase. A starch granule is composed of: 69-74% amylopectin, 26-31% amylose, 11-14% water, 0.2-0.4% protein, 0.5-0.9% lipid, 0.05-0.1% ash, 0.02-0.03% phosphorus, 0.1% pentosan. Approximately 70% of a granule is amorphous and 30% is crystalline.

A common enzymatic liquefaction process involves adjusting the pH of a granular starch slurry to between 6.0 and 6.5, the pH optimum of alpha-amylase derived from *Bacillus licheniformis*, with the addition of calcium hydroxide, sodium hydroxide or sodium carbonate. The addition of calcium hydroxide has the advantage of also providing calcium ions which are known to stabilize the alpha-amylase against inactivation. Upon addition of alpha-amylase, the suspension is pumped through a steam jet to instantaneously raise the temperature to between 80° C. to 115° C. The starch is immediately gelatinized and, due to the presence of alpha-amylase, depolymerized through random hydrolysis of a (1-4) glycosidic bonds by alpha-amylase to a fluid mass which is easily pumped.

In a second variation to the liquefaction process, alpha-amylase is added to the starch suspension, the suspension is held at a temperature of 80-100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of alpha-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using alpha-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of alpha-amylase until a DE of 10-20 is achieved, usually a period of 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

Corn wet milling is a process which produces corn oil, gluten meal, gluten feed and starch. Alkaline-amylase is used in the liquefaction of starch and glucoamylase is used in saccharification, producing glucose. Corn, a kernel of which consists of a outer seed coat (fiber), starch, a combination of starch and glucose and the inner germ, is subjected to a four step process, which results in the production of starch. The corn is steeped, de-germed, de-fibered, and finally the gluten is separated. In the steeping process, the solubles are taken out. The product remaining after removal of the solubles is de-germed, resulting in production of corn oil and production of an oil cake, which is added to the solubles from the steeping step. The remaining product is de-fibered and the fiber solids are added to the oil cake/ solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification to produce glucose.

Staling of baked products (such as bread) has been recognized as a problem which becomes more serious as more time lies between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. The increase in crumb firmness, which is considered as the most important aspect of staling, is recognized by the consumer a long time before the bread product has otherwise become unsuitable for consumption.

There is a need in the industry for the identification and optimization of amylases, useful for various uses, including commercial cornstarch liquefaction processes. These second generation acid amylases will offer improved manufacturing and/or performance characteristics over the industry standard enzymes from *Bacillus licheniformis*, for example.

There is also a need for the identification and optimization of amylases having utility in automatic dish wash (ADW) products and laundry detergent. In ADW products, the amylase will function at pH 10-11 and at 45-60° C. in the presence of calcium chelators and oxidative conditions. For laundry, activity at pH 9-10 and 40° C. in the appropriate detergent matrix will be required. Amylases are also useful in textile desizing, brewing processes, starch modification in the paper and pulp industry and other processes described in the art.

Amylases can be used commercially in the initial stages (liquefaction) of starch processing; in wet corn milling; in alcohol production; as cleaning agents in detergent matrices; in the textile industry for starch desizing; in baking applications; in the beverage industry; in oilfields in drilling processes; in inking of recycled paper and in animal feed. Amylases are also useful in textile desizing, brewing processes, starch modification in the paper and pulp industry and other processes.

The publications discussed herein are provided solely for their disclosure prior to the filing date of the present application. Nothing herein is to be construed as an admission that the invention is not entitled to antedate such disclosure by virtue of prior invention.

SUMMARY

The invention provides isolated or recombinant nucleic acids comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues, wherein the nucleic acid encodes at least one polypeptide having an amylase activity, and the sequence identities are determined by analysis with a sequence comparison algorithm or by a visual inspection. Exemplary nucleic acids of the invention include isolated or recombinant nucleic acids comprising a nucleic acid sequence as set forth in SEQ ID NO:1, and subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript.

Exemplary nucleic acids of the invention also include isolated or recombinant nucleic acids encoding a polypeptide having a sequence as set forth in SEQ ID NO:2, and subsequences thereof and variants thereof. In one aspect, the polypeptide has an amylase activity, e.g., an alpha amylase activity.

In one aspect, the invention also provides amylase-encoding nucleic acids with a common novelty in that they are derived from mixed cultures. The invention provides amylase-encoding nucleic acids isolated from mixed cultures comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues, wherein the nucleic acid encodes at least one polypeptide having an amylase activity, and the sequence identities are determined by analysis with a sequence comparison algorithm or by a visual inspection. In one aspect, the invention provides amylase-encoding nucleic acids isolated from mixed cultures comprising a nucleic acid sequence as set forth in SEQ ID NO:1, and subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript.

In one aspect, the invention also provides amylase-encoding nucleic acids with a common novelty in that they are derived from environmental sources, e.g., mixed environmental sources. In one aspect, the invention provides amylase-encoding nucleic acids isolated from environmental sources, e.g., mixed environmental sources, comprising a nucleic acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues, wherein the nucleic acid encodes at least one polypeptide having an amylase activity, and the sequence identities are determined by analysis with a sequence comparison algorithm or by a visual inspection. In one aspect, the invention provides amylase-encoding nucleic acids isolated from environmental sources, e.g., mixed environmental sources, comprising a nucleic acid sequence as set forth in SEQ ID NO:1, and subsequences thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of a gene or transcript.

In one aspect, the sequence comparison algorithm is a BLAST version 2.2.2 algorithm where a filtering setting is set to blastall −p blastp −d "nr pataa" −F F, and all other options are set to default.

Another aspect of the invention is an isolated or recombinant nucleic acid including at least 10 consecutive bases of a nucleic acid sequence of the invention, sequences substantially identical thereto, and the sequences complementary thereto.

In one aspect, the amylase activity comprises α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. The amylase activity can comprise a glucoamylase activity, a 1,4-α-D-glucan glucohydrolase activity, an α-amylase activity, an exoamylase activity, or a β-amylase activity.

The amylase activity can comprise hydrolyzing glucosidic bonds. In one aspect, the glucosidic bonds comprise an α-1,4-glucosidic bond. In another aspect, the glucosidic bonds comprise an α-1,6-glucosidic bond. In one aspect, the amylase activity comprises hydrolyzing glucosidic bonds in starch, e.g., liquefied starch. The amylase activity can further comprise hydrolyzing glucosidic bonds into maltodextrins. In one aspect, the amylase activity comprises cleaving a maltose or a D-glucose unit from non-reducing end of the starch.

In one aspect, the isolated or recombinant nucleic acid encodes a polypeptide having an amylase activity which is thermostable. The polypeptide can retain an amylase activity under conditions comprising a temperature range of between about 37° C. to about 95° C.; between about 55° C. to about 85° C., between about 70° C. to about 95° C., or, between about 90° C. to about 95° C.

In another aspect, the isolated or recombinant nucleic acid encodes a polypeptide having an amylase activity which is thermotolerant. The polypeptide can retain an amylase activity after exposure to a temperature in the range from greater than 37° C. to about 95° C. or anywhere in the range from greater than 55° C. to about 85° C. In one aspect, the polypeptide retains an amylase activity after exposure to a temperature in the range from greater than 90° C. to about 95° C. at pH 4.5.

The invention provides isolated or recombinant nucleic acids comprising a sequence that hybridizes under stringent conditions to a nucleic acid comprising a sequence as set forth in SEQ ID NO:1, or fragments or subsequences thereof. In one aspect, the nucleic acid encodes a polypeptide having an amylase activity. The nucleic acid can be at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length or the full length of the gene or transcript. In one aspect, the stringent conditions include a wash step comprising a wash in 0.2×SSC at a temperature of about 65° C. for about 15 minutes.

The invention provides a nucleic acid probe for identifying a nucleic acid encoding a polypeptide having an amylase activity, wherein the probe comprises at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more, consecutive bases of a sequence comprising a sequence of the invention, or fragments or subsequences thereof, wherein the probe identifies the nucleic acid by binding or hybridization. The probe can comprise an oligonucleotide comprising at least about 10 to 50, about 20 to 60, about 30 to 70, about 40 to 80, or about 60 to 100 consecutive bases of a sequence comprising a sequence of the invention, or fragments or subsequences thereof.

The invention provides a nucleic acid probe for identifying a nucleic acid encoding a polypeptide having an amylase activity, wherein the probe comprises a nucleic acid comprising a sequence at least about 10, 15, 20, 30, 40, 50, 60, 70, 80, 90, 100, 150, 200, 250, 300, 350, 400, 450, 500, 550, 600, 650, 700, 750, 800, 850, 900, 950, 1000 or more residues having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to a nucleic acid of the invention, wherein the sequence identities are determined by analysis with a sequence comparison algorithm or by visual inspection.

The probe can comprise an oligonucleotide comprising at least about 10 to 50, about 20 to 60, about 30 to 70, about 40 to 80, or about 60 to 100 consecutive bases of a nucleic acid sequence of the invention, or a subsequence thereof.

The invention provides an amplification primer sequence pair for amplifying a nucleic acid encoding a polypeptide having an amylase activity, wherein the primer pair is capable of amplifying a nucleic acid comprising a sequence of the invention, or fragments or subsequences thereof. One or each member of the amplification primer sequence pair can comprise an oligonucleotide comprising at least about 10 to 50 consecutive bases of the sequence.

The invention provides methods of amplifying a nucleic acid encoding a polypeptide having an amylase activity comprising amplification of a template nucleic acid with an amplification primer sequence pair capable of amplifying a nucleic acid sequence of the invention, or fragments or subsequences thereof.

The invention provides expression cassettes comprising a nucleic acid of the invention or a subsequence thereof. In one aspect, the expression cassette can comprise the nucleic acid that is operably linked to a promoter. The promoter can be a viral, bacterial, mammalian or plant promoter. In one aspect, the plant promoter can be a potato, rice, corn, wheat, tobacco or barley promoter. The promoter can be a constitutive promoter. The constitutive promoter can comprise CaMV35S. In another aspect, the promoter can be an inducible promoter. In one aspect, the promoter can be a tissue-specific promoter or an environmentally regulated or a developmentally regulated promoter. Thus, the promoter can be, e.g., a seed-specific, a leaf-specific, a root-specific, a stem-specific or an abscission-induced promoter. In one aspect, the expression cassette can further comprise a plant or plant virus expression vector.

The invention provides cloning vehicles comprising an expression cassette (e.g., a vector) of the invention or a nucleic acid of the invention. The cloning vehicle can be a viral vector, a plasmid, a phage, a phagemid, a cosmid, a fosmid, a bacteriophage or an artificial chromosome. The viral vector can comprise an adenovirus vector, a retroviral vector or an adeno-associated viral vector. The cloning vehicle can comprise a bacterial artificial chromosome (BAC), a plasmid, a bacteriophage P1-derived vector (PAC), a yeast artificial chromosome (YAC), or a mammalian artificial chromosome (MAC).

The invention provides transformed cell comprising a nucleic acid of the invention or an expression cassette (e.g., a vector) of the invention, or a cloning vehicle of the invention. In one aspect, the transformed cell can be a bacterial cell, a mammalian cell, a fungal cell, a yeast cell, an insect cell or a plant cell. In one aspect, the plant cell can be a potato, wheat, rice, corn, tobacco or barley cell.

The invention provides transgenic non-human animals comprising a nucleic acid of the invention or an expression cassette (e.g., a vector) of the invention. In one aspect, the animal is a mouse.

The invention provides transgenic plants comprising a nucleic acid of the invention or an expression cassette (e.g., a vector) of the invention. The transgenic plant can be a corn plant, a potato plant, a tomato plant, a wheat plant, an oilseed plant, a rapeseed plant, a soybean plant, a rice plant, a barley plant or a tobacco plant.

The invention provides transgenic seeds comprising a nucleic acid of the invention or an expression cassette (e.g., a vector) of the invention. The transgenic seed can be a corn seed, a wheat kernel, an oilseed, a rapeseed, a soybean seed, a palm kernel, a sunflower seed, a sesame seed, a peanut or a tobacco plant seed.

The invention provides an antisense oligonucleotide comprising a nucleic acid sequence complementary to or capable of hybridizing under stringent conditions to a nucleic acid of the invention. The invention provides methods of inhibiting the translation of an amylase message in a cell comprising administering to the cell or expressing in the cell an antisense oligonucleotide comprising a nucleic acid sequence complementary to or capable of hybridizing under stringent conditions to a nucleic acid of the invention.

The invention provides an isolated or recombinant polypeptide comprising an amino acid sequence having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide or peptide of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more residues, or over the full length of the polypeptide, and the sequence identities are determined by analysis with a sequence comparison algorithm or by a visual inspection. Exemplary polypeptide or peptide sequences of the invention include SEQ ID NO:2, and subsequences thereof and variants thereof, e.g., at least about 10, 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500 or more residues in length, or over the full length of an enzyme. Exemplary polypeptide or peptide sequences of the invention include sequence encoded by a nucleic acid of the invention. Exemplary polypeptide or peptide sequences of the invention include polypeptides or peptides specifically bound by an antibody of the invention. In one aspect, a polypeptide of the invention has at least one amylase activity, e.g., an alpha amylase activity.

Another aspect of the invention is an isolated or recombinant polypeptide or peptide including at least 10 consecutive bases of a polypeptide or peptide sequence of the invention, sequences substantially identical thereto, and the sequences complementary thereto.

In one aspect, the amylase activity of a polypeptide or peptide of the invention comprises an α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. The amylase activity can comprise a glucoamylase activity, a 1,4-α-D-glucan glucohydrolase activity, an α-amylase activity, an exoamylase activity, or a β-amylase activity. The amylase activity can comprise hydrolyzing glucosidic bonds. In one aspect, the glucosidic bonds comprise an α-1,4-glucosidic bond. In another aspect, the glucosidic bonds comprise an α-1,6-glucosidic bond. In one aspect, the amylase activity comprises hydrolyzing glucosidic bonds in starch, e.g., liquefied starch. The amylase activity can further comprise hydrolyzing glucosidic bonds into maltodextrins. In one aspect, the amylase activity comprises cleaving a maltose or a D-glucose unit from non-reducing end of the starch.

In one aspect, the amylase activity can be thermostable. The polypeptide can retain an amylase activity under conditions comprising a temperature range of between about 37° C. to about 95° C., between about 55° C. to about 85° C., between about 70° C. to about 95° C., or between about 90° C. to about 95° C. In another aspect, the amylase activity can be thermotolerant. The polypeptide can retain an amylase activity after exposure to a temperature in the range from greater than 37° C. to about 95° C., or in the range from greater than 55° C. to about 85° C. In one aspect, the polypeptide can retain an amylase activity after exposure to a temperature in the range from greater than 90° C. to about 95° C. at pH 4.5.

In one aspect, the isolated or recombinant polypeptide can comprise the polypeptide of the invention that lacks a signal sequence. In one aspect, the isolated or recombinant polypeptide can comprise the polypeptide of the invention comprising a heterologous signal sequence, such as a heterologous amylase or non-amylase signal sequence.

In one aspect, the invention provides a signal sequence comprising an amino terminal peptide of SEQ ID NO:2. In one aspect, the invention provides a signal sequence consisting of a peptide having a subsequence of SEQ ID NO:2. In one aspect, the invention provides chimeric proteins comprising a first domain comprising a signal sequence of the invention and at least a second domain. The protein can be a fusion protein. The second domain can comprise an enzyme. The enzyme can be an amylase (e.g., an amylase of the invention, or, another amylase).

In one aspect, the amylase activity comprises a specific activity at about 37° C. in the range from about 100 to about 1000 units per milligram of protein. In another aspect, the amylase activity comprises a specific activity from about 500 to about 750 units per milligram of protein. Alternatively, the amylase activity comprises a specific activity at 37° C. in the range from about 500 to about 1200 units per milligram of protein. In one aspect, the amylase activity comprises a specific activity at 37° C. in the range from about 750 to about 1000 units per milligram of protein. In another aspect, the thermotolerance comprises retention of at least half of the specific activity of the amylase at 37° C. after being heated to the elevated temperature. Alternatively, the thermotolerance can comprise retention of specific activity at 37° C. in the range from about 500 to about 1200 units per milligram of protein after being heated to the elevated temperature.

The invention provides the isolated or recombinant polypeptide of the invention, wherein the polypeptide comprises at least one glycosylation site. In one aspect, glycosylation can be an N-linked glycosylation. In one aspect, the polypeptide can be glycosylated after being expressed in a *P. pastoris* or a *S. pombe*.

In one aspect, the polypeptide can retain an amylase activity under conditions comprising about pH 6.5, pH 6, pH 5.5, pH 5, pH 4.5 or pH 4. In another aspect, the polypeptide can retain an amylase activity under conditions comprising about pH 7, pH 7.5 pH 8.0, pH 8.5, pH 9, pH 9.5, pH 10, pH 10.5 or pH 11.

The invention provides protein preparations comprising a polypeptide of the invention, wherein the protein preparation comprises a liquid, a solid or a gel.

The invention provides heterodimers comprising a polypeptide of the invention and a second domain. In one aspect, the second domain can be a polypeptide and the heterodimer can be a fusion protein. In one aspect, the second domain can be an epitope or a tag. In one aspect, the invention provides homodimers comprising a polypeptide of the invention.

The invention provides immobilized polypeptides having an amylase activity, wherein the polypeptide comprises a polypeptide of the invention, a polypeptide encoded by a nucleic acid of the invention, or a polypeptide comprising a polypeptide of the invention and a second domain. In one aspect, the polypeptide can be immobilized on a cell, a metal, a resin, a polymer, a ceramic, a glass, a microelectrode, a graphitic particle, a bead, a gel, a plate, an array or a capillary tube.

The invention provides arrays comprising an immobilized nucleic acid of the invention. The invention provides arrays comprising an antibody of the invention.

The invention provides isolated or recombinant antibodies that specifically bind to a polypeptide of the invention or to a polypeptide encoded by a nucleic acid of the invention. The antibody can be a monoclonal or a polyclonal antibody. The invention provides hybridomas comprising an antibody of the invention, e.g., an antibody that specifically binds to a polypeptide of the invention or to a polypeptide encoded by a nucleic acid of the invention.

The invention provides food supplements for an animal comprising a polypeptide of the invention, e.g., a polypeptide encoded by the nucleic acid of the invention. In one aspect, the polypeptide in the food supplement can be glycosylated. The invention provides edible enzyme delivery matrices comprising a polypeptide of the invention, e.g., a polypeptide encoded by the nucleic acid of the invention. In one aspect, the delivery matrix comprises a pellet. In one aspect, the polypeptide can be glycosylated. In one aspect, the amylase activity is thermotolerant. In another aspect, the amylase activity is thermostable.

The invention provides method of isolating or identifying a polypeptide having an amylase activity comprising the steps of: (a) providing an antibody of the invention; (b) providing a sample comprising polypeptides; and (c) contacting the sample of step (b) with the antibody of step (a) under conditions wherein the antibody can specifically bind to the polypeptide, thereby isolating or identifying a polypeptide having an amylase activity.

The invention provides methods of making an anti-amylase antibody comprising administering to a non-human animal a nucleic acid of the invention or a polypeptide of the invention or subsequences thereof in an amount sufficient to generate a humoral immune response, thereby making an anti-amylase antibody. The invention provides methods of making an anti-amylase immune comprising administering to a non-human animal a nucleic acid of the invention or a polypeptide of the invention or subsequences thereof in an amount sufficient to generate an immune response.

The invention provides methods of producing a recombinant polypeptide comprising the steps of: (a) providing a nucleic acid of the invention operably linked to a promoter; and (b) expressing the nucleic acid of step (a) under conditions that allow expression of the polypeptide, thereby producing a recombinant polypeptide. In one aspect, the method can further comprise transforming a host cell with the nucleic acid of step (a) followed by expressing the nucleic acid of step (a), thereby producing a recombinant polypeptide in a transformed cell.

The invention provides methods for identifying a polypeptide having an amylase activity comprising the following steps: (a) providing a polypeptide of the invention; or a polypeptide encoded by a nucleic acid of the invention; (b) providing an amylase substrate; and (c) contacting the polypeptide or a fragment or variant thereof of step (a) with the substrate of step (b) and detecting a decrease in the amount of substrate or an increase in the amount of a reaction product, wherein a decrease in the amount of the substrate or an increase in the amount of the reaction product detects a polypeptide having an amylase activity. In one aspect, the substrate can be a starch, e.g., a liquefied starch.

The invention provides methods for identifying an amylase substrate comprising the following steps: (a) providing a polypeptide of the invention; or a polypeptide encoded by a nucleic acid of the invention; (b) providing a test substrate; and (c) contacting the polypeptide of step (a) with the test substrate of step (b) and detecting a decrease in the amount of substrate or an increase in the amount of reaction product, wherein a decrease in the amount of the substrate or an increase in the amount of a reaction product identifies the test substrate as an amylase substrate.

The invention provides methods of determining whether a test compound specifically binds to a polypeptide comprising the following steps: (a) expressing a nucleic acid or a vector comprising the nucleic acid under conditions permissive for translation of the nucleic acid to a polypeptide, wherein the nucleic acid comprises a nucleic acid of the invention, or, providing a polypeptide of the invention; (b) providing a test compound; (c) contacting the polypeptide with the test compound; and (d) determining whether the test compound of step (b) specifically binds to the polypeptide.

The invention provides methods for identifying a modulator of an amylase activity comprising the following steps: (a) providing a polypeptide of the invention or a polypeptide encoded by a nucleic acid of the invention; (b) providing a test compound; (c) contacting the polypeptide of step (a) with the test compound of step (b) and measuring an activity of the amylase, wherein a change in the amylase activity measured in the presence of the test compound compared to the activity in the absence of the test compound provides a determination that the test compound modulates the amylase activity. In one aspect, the amylase activity can be measured by providing an amylase substrate and detecting a decrease in the amount of the substrate or an increase in the amount of a reaction product, or, an increase in the amount of the substrate or a decrease in the amount of a reaction product. A decrease in the amount of the substrate or an increase in the amount of the reaction product with the test compound as compared to the amount of substrate or reaction product without the test compound identifies the test compound as an activator of amylase activity. An increase in the amount of the substrate or a decrease in the amount of the reaction product with the test compound as compared to the amount of substrate or reaction product without the test compound identifies the test compound as an inhibitor of amylase activity.

The invention provides computer systems comprising a processor and a data storage device wherein said data storage device has stored thereon a polypeptide sequence or a nucleic acid sequence of the invention (e.g., a polypeptide encoded by a nucleic acid of the invention). In one aspect, the computer system can further comprise a sequence comparison algorithm and a data storage device having at least one reference sequence stored thereon. In another aspect, the sequence comparison algorithm comprises a computer program that indicates polymorphisms. In one aspect, the computer system can further comprise an identifier that identifies one or more features in said sequence. The invention provides computer readable media having stored thereon a polypeptide sequence or a nucleic acid sequence of the invention. The invention provides methods for identifying a feature in a sequence comprising the steps of: (a) reading the sequence using a computer program which identifies one or more features in a sequence, wherein the sequence comprises a polypeptide sequence or a nucleic acid sequence of the invention; and (b) identifying one or more features in the sequence with the computer program. The invention provides methods for comparing a first sequence to a second sequence comprising the steps of: (a) reading the first sequence and the second sequence through use of a computer program which compares sequences, wherein the first sequence comprises a polypeptide sequence or a nucleic acid sequence of the invention; and (b) determining differences between the first sequence and the second sequence with the computer program. The step of determining differences between the first sequence and the second sequence can further comprise the step of identifying polymorphisms. In one aspect, the method can further comprise an identifier that identifies one or more features in a sequence. In another aspect, the method can comprise reading the first sequence using a computer program and identifying one or more features in the sequence.

The invention provides methods for isolating or recovering a nucleic acid encoding a polypeptide having an amylase activity from an environmental sample comprising the steps of: (a) providing an amplification primer sequence pair for amplifying a nucleic acid encoding a polypeptide having an amylase activity, wherein the primer pair is capable of amplifying a nucleic acid of the invention; (b) isolating a nucleic acid from the environmental sample or treating the environmental sample such that nucleic acid in the sample is accessible for hybridization to the amplification primer pair; and, (c) combining the nucleic acid of step (b) with the amplification primer pair of step (a) and amplifying nucleic acid from the environmental sample, thereby isolating or recovering a nucleic acid encoding a polypeptide having an amylase activity from an environmental sample. One or each member of the amplification primer sequence pair can comprise an oligonucleotide comprising at least about 10 to 50 consecutive bases of a sequence of the invention.

The invention provides methods for isolating or recovering a nucleic acid encoding a polypeptide having an amylase activity from an environmental sample comprising the steps of: (a) providing a polynucleotide probe comprising a nucleic acid of the invention or a subsequence thereof; (b) isolating a nucleic acid from the environmental sample or treating the environmental sample such that nucleic acid in the sample is accessible for hybridization to a polynucleotide probe of step (a); (c) combining the isolated nucleic acid or the treated environmental sample of step (b) with the polynucleotide probe of step (a); and (d) isolating a nucleic acid that specifically hybridizes with the polynucleotide probe of step (a), thereby isolating or recovering a nucleic acid encoding a polypeptide having an amylase activity from an environmental sample. The environmental sample can comprise a water sample, a liquid sample, a soil sample, an air sample or a biological sample. In one aspect, the biological sample can be derived from a bacterial cell, a protozoan cell, an insect cell, a yeast cell, a plant cell, a fungal cell or a mammalian cell.

The invention provides methods of generating a variant of a nucleic acid encoding a polypeptide having an amylase activity comprising the steps of: (a) providing a template nucleic acid comprising a nucleic acid of the invention; and (b) modifying, deleting or adding one or more nucleotides in the template sequence, or a combination thereof, to generate a variant of the template nucleic acid. In one aspect, the method can further comprise expressing the variant nucleic acid to generate a variant amylase polypeptide. The modifications, additions or deletions can be introduced by a method comprising error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

In one aspect, the method can be iteratively repeated until an amylase having an altered or different activity or an altered or different stability from that of a polypeptide encoded by the template nucleic acid is produced. In one aspect, the variant amylase polypeptide is thermotolerant, and retains some activity after being exposed to an elevated temperature. In another aspect, the variant amylase polypeptide has increased glycosylation as compared to the amylase encoded by a template nucleic acid. Alternatively, the variant amylase polypeptide has an amylase activity under a high temperature, wherein the amylase encoded by the template nucleic acid is not active under the high temperature. In one aspect, the method can be iteratively repeated until an amylase coding sequence having an altered codon usage from that of the template nucleic acid is produced. In another aspect, the method can be iteratively repeated until an amylase gene having higher or lower level of message expression or stability from that of the template nucleic acid is produced.

The invention provides methods for modifying codons in a nucleic acid encoding a polypeptide having an amylase activity to increase its expression in a host cell, the method comprising the following steps: (a) providing a nucleic acid of the invention encoding a polypeptide having an amylase activity; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying codons in a nucleic acid encoding a polypeptide having an amylase activity; the method comprising the following steps: (a) providing a nucleic acid of the invention; and, (b) identifying a codon in the nucleic acid of step (a) and replacing it with a different codon encoding the same amino acid as the replaced codon, thereby modifying codons in a nucleic acid encoding an amylase.

The invention provides methods for modifying codons in a nucleic acid encoding a polypeptide having an amylase activity to increase its expression in a host cell, the method comprising the following steps: (a) providing a nucleic acid of the invention encoding an amylase polypeptide; and, (b) identifying a non-preferred or a less preferred codon in the nucleic acid of step (a) and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the nucleic acid to increase its expression in a host cell.

The invention provides methods for modifying a codon in a nucleic acid encoding a polypeptide having an amylase activity to decrease its expression in a host cell, the method comprising the following steps: (a) providing a nucleic acid of the invention; and (b) identifying at least one preferred codon in the nucleic acid of step (a) and replacing it with a non-preferred or less preferred codon encoding the same amino acid as the replaced codon, wherein a preferred codon is a codon over-represented in coding sequences in genes in a host cell and a non-preferred or less preferred codon is a codon under-represented in coding sequences in genes in the host cell, thereby modifying the nucleic acid to decrease its expression in a host cell. In one aspect, the host cell can be a bacterial cell, a fungal cell, an insect cell, a yeast cell, a plant cell or a mammalian cell.

The invention provides methods for producing a library of nucleic acids encoding a plurality of modified amylase active sites or substrate binding sites, wherein the modified active sites or substrate binding sites are derived from a first nucleic acid comprising a sequence encoding a first active site or a first substrate binding site the method comprising the following steps: (a) providing a first nucleic acid encoding a first active site or first substrate binding site, wherein the first nucleic acid sequence comprises a sequence that hybridizes under stringent conditions to a nucleic acid of the invention, and the nucleic acid encodes an amylase active site or an amylase substrate binding site; (b) providing a set of mutagenic oligonucleotides that encode naturally-occurring amino acid variants at a plurality of targeted codons in the first nucleic acid; and, (c) using the set of mutagenic oligonucleotides to generate a set of active site-encoding or substrate binding site-encoding variant nucleic acids encoding a range of amino acid variations at each amino acid codon that was mutagenized, thereby producing a library of nucleic acids encoding a plurality of modified amylase active sites or substrate binding sites. In one aspect, the method comprises mutagenizing the first nucleic acid of step (a) by a method comprising an optimized directed evolution system, gene site-saturation mutagenesis (GSSM), synthetic ligation reassembly (SLR), error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR) and a combination thereof. In another aspect, the method comprises mutagenizing the first nucleic acid of step (a) or variants by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof.

The invention provides methods for making a small molecule comprising the following steps: (a) providing a plurality of biosynthetic enzymes capable of synthesizing or modifying a small molecule, wherein one of the enzymes comprises an amylase enzyme encoded by a nucleic acid of the invention; (b) providing a substrate for at least one of the enzymes of step (a); and (c) reacting the substrate of step (b) with the enzymes under conditions that facilitate a plurality of biocatalytic reactions to generate a small molecule by a series of biocatalytic reactions. The invention provides methods for modifying a small molecule comprising the following steps: (a) providing an amylase enzyme, wherein the enzyme comprises a polypeptide of the invention, or, a polypeptide encoded by a nucleic acid of the invention, or a subsequence thereof; (b) providing a small molecule; and (c) reacting the enzyme of step (a) with the small molecule of step (b) under conditions that facilitate an enzymatic reaction catalyzed by the amylase enzyme, thereby modifying a small molecule by an amylase enzymatic reaction. In one aspect, the method can comprise a plurality of small molecule substrates for the enzyme of step (a), thereby generating a library of modified small molecules produced by at least one enzymatic reaction catalyzed by the amylase enzyme. In one aspect, the method can comprise a plurality of additional enzymes under conditions that facilitate a plurality of biocatalytic reactions by the enzymes to form a library of modified small molecules produced by the plurality of enzymatic reactions. In another aspect, the method can further comprise the step of testing the library to determine if a particular modified small molecule which exhibits a desired activity is present within the library. The step of testing the library can further comprise the steps of systematically eliminating all but one of the biocatalytic reactions used to produce a portion of the plurality of the modified small molecules within the library by testing the portion of the modified small molecule for the presence or absence of the particular modified small molecule with a desired activity, and identifying at least one specific biocatalytic reaction that produces the particular modified small molecule of desired activity.

The invention provides methods for determining a functional fragment of an amylase enzyme comprising the steps of: (a) providing an amylase enzyme, wherein the enzyme comprises a polypeptide of the invention, or a polypeptide encoded by a nucleic acid of the invention, or a subsequence thereof; and (b) deleting a plurality of amino acid residues from the sequence of step (a) and testing the remaining subsequence for an amylase activity, thereby determining a functional fragment of an amylase enzyme. In one aspect, the amylase activity is measured by providing an amylase substrate and detecting a decrease in the amount of the substrate or an increase in the amount of a reaction product.

The invention provides methods for whole cell engineering of new or modified phenotypes by using real-time metabolic flux analysis, the method comprising the following steps: (a) making a modified cell by modifying the genetic composition of a cell, wherein the genetic composition is modified by addition to the cell of a nucleic acid of the invention; (b) culturing the modified cell to generate a plurality of modified cells; (c) measuring at least one metabolic parameter of the cell by monitoring the cell culture of step (b) in real time; and, (d) analyzing the data of step (c) to determine if the measured parameter differs from a comparable measurement in an unmodified cell under similar conditions, thereby identifying an engineered phenotype in the cell using real-time metabolic flux analysis. In one aspect, the genetic composition of the cell can be modified by a method comprising deletion of a sequence or modification of a sequence in the cell, or, knocking out the expression of a gene. In one aspect, the method can further comprise selecting a cell comprising a newly engineered phenotype. In another aspect, the method can comprise culturing the selected cell, thereby generating a new cell strain comprising a newly engineered phenotype.

The invention provides methods for hydrolyzing a starch comprising the following steps: (a) providing a polypeptide having an amylase activity, wherein the polypeptide comprises a polypeptide of the invention; (b) providing a composition comprising a starch; and (c) contacting the polypeptide of step (a) with the composition of step (b) under conditions wherein the polypeptide hydrolyzes the starch. In one aspect, the composition comprising starch that comprises an $\alpha$-1,4-glucosidic bond or an $\alpha$-1,6-glucosidic bond. In one aspect, the amylase activity is an $\alpha$-amylase activity. In one aspect, the $\alpha$-amylase activity hydrolyzes internal bonds in a starch or other polysaccharide.

The invention provides methods for liquefying or removing a starch from a composition comprising the following steps: (a) providing a polypeptide having an amylase activity, wherein the polypeptide comprises a polypeptide of the invention; (b) providing a composition comprising a starch; and (c) contacting the polypeptide of step (a) with the composition of step (b) under conditions wherein the polypeptide removes or liquefies the starch.

The invention provides methods of increasing thermotolerance or thermostability of an amylase polypeptide, the method comprising glycosylating an amylase polypeptide, wherein the polypeptide comprises at least thirty contiguous amino acids of a polypeptide of the invention; or a polypeptide encoded by a nucleic acid sequence of the invention, thereby increasing the thermotolerance or thermostability of the amylase polypeptide. In one aspect, the amylase specific activity can be thermostable or thermotolerant at a temperature in the range from greater than about 37° C. to about 95° C.

The invention provides methods for overexpressing a recombinant amylase polypeptide in a cell comprising expressing a vector comprising a nucleic acid comprising a nucleic acid of the invention or a nucleic acid sequence of the invention, wherein the sequence identities are determined by analysis with a sequence comparison algorithm or by visual inspection, wherein overexpression is effected by use of a high activity promoter, a dicistronic vector or by gene amplification of the vector.

The invention provides detergent compositions comprising a polypeptide of the invention or a polypeptide encoded by a nucleic acid of the invention, wherein the polypeptide comprises an amylase activity. In one aspect, the amylase can be a nonsurface-active amylase. In another aspect, the amylase can be a surface-active amylase.

The invention provides methods for washing an object comprising the following steps: (a) providing a composition comprising a polypeptide having an amylase activity, wherein the polypeptide comprises: a polypeptide of the invention or a polypeptide encoded by a nucleic acid of the invention; (b) providing an object; and (c) contacting the polypeptide of step (a) and the object of step (b) under conditions wherein the composition can wash the object.

The invention provides methods for hydrolyzing starch, e.g., in a feed or a food prior to consumption by an animal, comprising the following steps: (a) obtaining a composition, e.g., a feed material, comprising a starch, wherein the polypeptide comprises: a polypeptide of the invention or a polypeptide encoded by a nucleic acid of the invention; and (b) adding the polypeptide of step (a) to the composition, e.g., the feed or food material, in an amount sufficient for a sufficient time period to cause hydrolysis of the starch, thereby hydrolyzing the starch. In one aspect, the food or feed comprises rice, corn, barley, wheat, legumes, or potato.

The invention provides methods for textile desizing comprising the following steps: (a) providing a polypeptide having an amylase activity, wherein the polypeptide comprises a polypeptide of the invention or a polypeptide encoded by a nucleic acid of the invention; (b) providing a fabric; and (c) contacting the polypeptide of step (a) and the fabric of step (b) under conditions wherein the amylase can desize the fabric.

The invention provides methods for deinking of paper or fibers comprising the following steps: (a) providing a polypeptide having an amylase activity, wherein the polypeptide comprises a polypeptide of the invention; (b) providing a composition comprising paper or fiber; and (c) contacting the polypeptide of step (a) and the composition of step (b) under conditions wherein the polypeptide can deink the paper or fiber.

The invention provides methods for treatment of lignocellulosic fibers comprising the following steps: (a) providing a polypeptide having an amylase activity, wherein the polypeptide comprises a polypeptide of the invention; (b) providing a lignocellulosic fiber; and (c) contacting the polypeptide of step (a) and the fiber of step (b) under conditions wherein the polypeptide can treat the fiber thereby improving the fiber properties.

The invention provides methods for producing a high-maltose or a high-glucose syrup comprising the following steps: (a) providing a polypeptide having an amylase activity, wherein the polypeptide comprises a polypeptide of the invention; (b) providing a composition comprising a starch; and (c) contacting the polypeptide of step (a) and the fabric of step (b) under conditions wherein the polypeptide of step (a) can liquefy the composition of step (b) thereby producing a soluble starch hydrolysate and saccharify the soluble starch hydrolysate thereby producing the syrup. In one aspect, the starch can be from rice, corn, barley, wheat, legumes, potato, or sweet potato.

The invention provides methods for improving the flow of the starch-containing production fluids comprising the following steps: (a) providing a polypeptide having an amylase activity, wherein the polypeptide comprises a polypeptide of the invention; (b) providing production fluid; and (c) contacting the polypeptide of step (a) and the production fluid of step (b) under conditions wherein the amylase can hydrolyze the starch in the production fluid thereby improving its flow by decreasing its density. In one aspect, the production fluid can be from a subterranean formation.

The invention provides anti-staling compositions comprising a polypeptide of the invention or a polypeptide encoded by a nucleic acid of the invention. The invention provides methods for preventing staling of the baked products comprising the following steps: (a) providing a polypeptide having an amylase activity, wherein the polypeptide comprises a polypeptide of the invention; (b) providing a composition containing starch used for baking; (c) combining the polypeptide of step (a) with the composition of the step (b) under conditions wherein the polypeptide can hydrolyze the starch in the composition used for baking thereby preventing staling of the baked product. In one aspect, the baked product can be bread.

The invention provides methods for using amylase in brewing or alcohol production comprising the following steps: (a) providing a polypeptide having an amylase activity, wherein the polypeptide comprises a polypeptide of the invention; (b) providing a composition containing starch and used for brewing or in alcohol production; (c) combining the polypeptide of step (a) with the composition of the step (b) under conditions wherein the polypeptide can hydrolyze the starch in the composition used for brewing or in alcohol production. In one aspect, the composition containing starch can be beer.

The invention provides methods of making a transgenic plant comprising the following steps: (a) introducing a heterologous nucleic acid sequence into the cell, wherein the heterologous nucleic sequence comprises a nucleic acid sequence of the invention, thereby producing a transformed plant cell; and (b) producing a transgenic plant from the transformed cell. In one aspect, the step (a) can further comprise introducing the heterologous nucleic acid sequence by electroporation or microinjection of plant cell protoplasts. In another aspect, the step (a) can further comprise introducing the heterologous nucleic acid sequence directly to plant tissue by DNA particle bombardment. Alternatively, the step (a) can further comprise introducing the heterologous nucleic acid sequence into the plant cell DNA using an *Agrobacterium tumefaciens* host. In one aspect, the plant cell can be a potato, corn, rice, wheat, tobacco, or barley cell.

The invention provides methods of expressing a heterologous nucleic acid sequence in a plant cell comprising the following steps: (a) transforming the plant cell with a heterologous nucleic acid sequence operably linked to a promoter, wherein the heterologous nucleic sequence comprises a nucleic acid of the invention; (b) growing the plant under conditions wherein the heterologous nucleic acids sequence is expressed in the plant cell.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase. The use of the amylase in accordance with the present invention provides an improved anti-staling effect as measured by, e.g. less crumb firming, retained crumb elasticity, improved sliceability (e.g. fewer crumbs, non-gummy crumb), improved palatability or flavor.

The invention provides an isolated nucleic acid having a sequence as set forth in SEQ ID NO: 1 and variants thereof having at least 50% sequence identity to SEQ ID NO: 1 and encoding polypeptides having alpha amylase activity. One aspect of the invention is an isolated nucleic acid having a sequence as set forth in SEQ ID NO: 1, sequences substantially identical thereto, and sequences complementary thereto. Another aspect of the invention is an isolated nucleic acid including at least 10 consecutive bases of a sequence as set forth in SEQ ID NO:1 nucleic acid sequences, sequences substantially identical thereto, and the sequences complementary thereto. In yet another aspect, the invention provides an isolated nucleic acid encoding a polypeptide having a sequence as set forth in SEQ ID NO.: 2 and variants thereof encoding a polypeptide having alpha amylase activity and having at least 50% sequence identity to such sequences. Another aspect of the invention is an isolated nucleic acid encoding a polypeptide or a functional fragment thereof having a sequence as set forth in SEQ ID NO: 2 and sequences substantially identical thereto. Another aspect of the invention is an isolated nucleic acid encoding a polypeptide having at least 10 consecutive amino acids of a sequence as set forth in SEQ ID NO:2, and sequences substantially identical thereto. In yet another aspect, the invention provides a purified polypeptide having a sequence as set forth in SEQ ID NO:2 and sequences substantially identical thereto. Another aspect of the invention is an isolated or purified antibody that specifically binds to a polypeptide having a sequence as set forth in SEQ ID NO:2, and sequences substantially identical thereto. Another aspect of the invention is an isolated or purified antibody or binding fragment thereof, which specifically binds to a polypeptide having at least 10 consecutive amino acids of one of the polypeptides of SEQ ID NO:2, and sequences substantially identical thereto. Another aspect of the invention is a method of making a polypeptide having a sequence as set forth in SEQ ID NO:2, and sequences substantially identical thereto.

The method includes introducing a nucleic acid encoding the polypeptide into a host cell, wherein the nucleic acid is operably linked to a promoter, and culturing the host cell under conditions that allow expression of the nucleic acid. Another aspect of the invention is a method of making a polypeptide having at least 10 amino acids of a sequence as set forth in SEQ ID NO:2, and sequences substantially identical thereto. The method includes introducing a nucleic acid encoding the polypeptide into a host cell, wherein the nucleic acid is operably linked to a promoter, and culturing the host cell under conditions that allow expression of the nucleic acid, thereby producing the polypeptide. Another aspect of the invention is a method of generating a variant including obtaining a nucleic acid having a sequence as set forth in SEQ ID NO:1 nucleic acid sequences, sequences substantially identical thereto, sequences complementary to the sequences of SEQ ID NO:1 nucleic acid sequences, fragments comprising at least 30 consecutive nucleotides of the foregoing sequences, and changing one or more nucleotides in the sequence to another nucleotide, deleting one or more nucleotides in the sequence, or adding one or more nucleotides to the sequence.

Another aspect of the invention is a computer readable medium having stored thereon a sequence as set forth in SEQ ID NO:1 nucleic acid sequences, and sequences substantially identical thereto, or a polypeptide sequence as set forth in SEQ ID NO:2, and sequences substantially identical thereto. Another aspect of the invention is a computer system including a processor and a data storage device wherein the data storage device has stored thereon a sequence as set forth in SEQ ID NO:1 nucleic acid sequences, and sequences substantially identical thereto, or a polypeptide having a sequence as set forth in SEQ ID NO:2, and sequences substantially identical thereto. Another aspect of the invention is a method for comparing a first sequence to a reference sequence wherein the first sequence is a nucleic acid having a sequence as set forth in SEQ ID NO:1 nucleic acid sequences, and sequences substantially identical thereto, or a polypeptide code of SEQ ID NO:2, and sequences substantially identical thereto. The method includes reading the first sequence and the reference sequence through use of a computer program which compares sequences; and determining differences between the first sequence and the reference sequence with the computer program. Another aspect of the invention is a method for identifying a feature in a sequence as set forth in SEQ ID NO:1 nucleic acid sequences, and sequences substantially identical thereto, or a polypeptide having a sequence as set forth in SEQ ID NO:2, and sequences substantially identical thereto, including reading the sequence through the use of a computer program which identifies features in sequences; and identifying features in the sequence with the computer program. Another aspect of the invention is an assay for identifying fragments or variants of SEQ ID NO:, and sequences substantially identical thereto, which retain the enzymatic function of the polypeptides of SEQ ID NO:2, and sequences substantially identical thereto. The assay includes contacting the polypeptide of SEQ ID NO:2, sequences substantially identical thereto, or polypeptide fragment or variant with a substrate molecule under conditions which allow the polypeptide fragment or variant to function, and detecting either a decrease in the level of substrate or an increase in the level of the specific reaction product of the reaction between the polypeptide and substrate thereby identifying a fragment or variant of such sequences.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase. The use of the amylase in accordance with the present invention provides an improved anti-staling effect as measured by, e.g. less crumb firming, retained crumb elasticity, improved sliceability (e.g. fewer crumbs, non-gummy crumb), improved palatability or flavor.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DESCRIPTION OF DRAWINGS

FIG. 6A shows the molecular weight fragments in syrups using enzymes of the invention.

FIG. 6B shows the molecular weight fragments in syrups using commercial enzymes.

FIGS. 7A-7N show sequences of the invention.

FIG. 7A shows SEQ ID NO:1 of the invention.

FIG. 7B shows SEQ ID NO:2 of the invention.

FIG. 7C shows SEQ ID NO:3 of the invention.

FIG. 7D shows SEQ ID NO:4 of the invention.

FIG. 7E shows SEQ ID NO:5 of the invention.

FIG. 7F shows SEQ ID NO:6 of the invention.

FIG. 7G shows SEQ ID NO:7 of the invention.

FIG. 7H shows SEQ ID NO:8 of the invention.

FIG. 7I shows SEQ ID NO:9 of the invention.

FIG. 7J shows SEQ ID NO:10 of the invention.

FIG. 7K shows SEQ ID NO:66 of the invention.

FIG. 7L shows SEQ ID NO:67 of the invention.

FIG. 7M shows SEQ ID NO:68 of the invention.

FIG. 7N shows SEQ ID NO:69 of the invention.

Like reference symbols in the various drawings indicate like elements.

Figure 1:
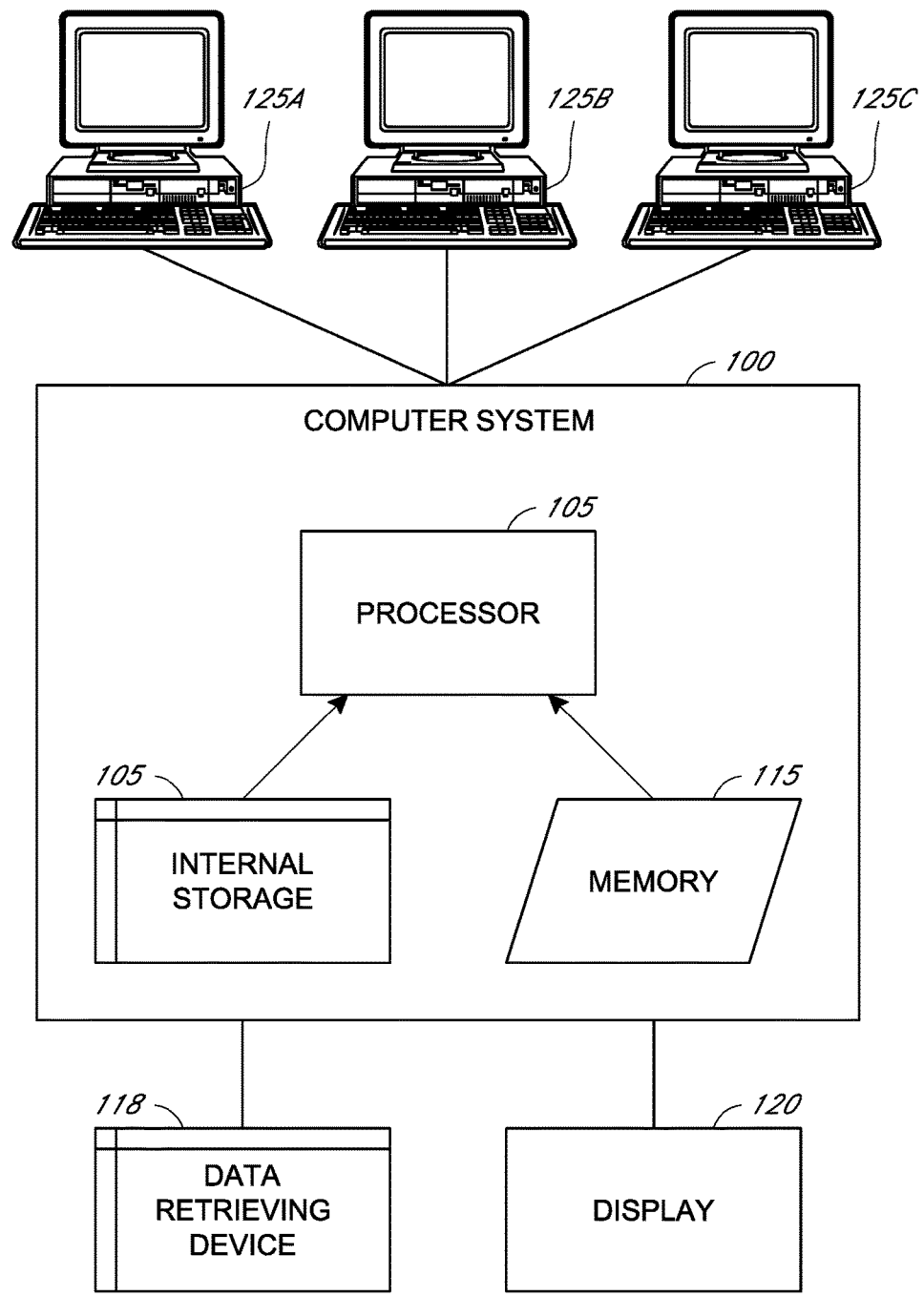
FIG. 1 is a block diagram of a computer system.

Sequences of the invention are additionally provided in a sequence listing.

DETAILED DESCRIPTION

The invention provides amylase enzymes, e.g., an alpha amylase, polynucleotides encoding the enzymes, methods of making and using these polynucleotides and polypeptides. The invention is directed to novel polypeptides having an amylase activity, e.g., an alpha amylase activity, nucleic acids encoding them and antibodies that bind to them. The polypeptides of the invention can be used in a variety of diagnostic, therapeutic, and industrial contexts. The polypeptides of the invention can be used as, e.g., an additive for a detergent, for processing foods and for chemical synthesis utilizing a reverse reaction. Additionally, the polypeptides of the invention can be used in fabric treatment, alcohol production, and as additives to food or animal feed.

In one aspect, the amylases of the invention are active at a high and/or at a low temperature, or, over a wide range of temperature. For example, they can be active in the temperatures ranging between 20° C. to 90° C., between 30° C. to 80° C., or between 40° C. to 70° C. The invention also provides amylases that have activity at alkaline pHs or at acidic pHs, e.g., low water acidity. In alternative aspects, the amylases of the invention can have activity in acidic pHs as low as pH 5.0, pH 4.5, pH 4.0, and pH 3.5. In alternative aspects, the amylases of the invention can have activity in alkaline pHs as high as pH 9.5, pH 10, pH 10.5, and pH 11. In one aspect, the amylases of the invention are active in the temperature range of between about 40° C. to about 70° C. under conditions of low water activity (low water content).

The invention also provides methods for further modifying the exemplary amylases of the invention to generate proteins with desirable properties. For example, amylases generated by the methods of the invention can have altered enzymatic activity, thermal stability, pH/activity profile, pH/stability profile (such as increased stability at low, e.g. pH<6 or pH<5, or high, e.g. pH>9, pH values), stability towards oxidation, $Ca^{2+}$ dependency, specific activity and the like. The invention provides for altering any property of interest. For instance, the alteration may result in a variant which, as compared to a parent enzyme, has altered enzymatic activity, or, pH or temperature activity profiles.

In one aspect, the present invention relates to alpha amylases and polynucleotides encoding them. As used herein, the term "alpha amylase" encompasses enzymes having alpha amylase activity, for example, enzymes capable of hydrolyzing starch to sugars. Unlike many known amylases, the exemplary amylase of the invention, set forth in SEQ ID NO:2, is not a calcium-dependent enzyme.

It is highly desirable to be able to decrease the $Ca^{2+}$ dependency of an alpha amylase. Accordingly, one aspect of the invention provides an amylase enzyme that has a decreased $Ca^{2+}$ dependency as compared to commercial or parent amylases. Decreased $Ca^{2+}$ dependency will in general have the functional consequence that the variant exhibits a satisfactory amylolytic activity in the presence of a lower concentration of calcium ion in the extraneous medium than is necessary for a commercial or parent enzyme. It will further often have the consequence that the variant is less sensitive to calcium ion-depleting conditions such as those obtained in media containing calcium-complexing agents (such as certain detergent builders).

The polynucleotides of the invention have been identified as encoding polypeptides having alpha amylase activity. An exemplary alpha amylase enzyme of the invention is shown in SEQ ID NO:2, also referred to herein as SEQ ID NO:2. Such amylases of the invention are particularly useful in corn-wet milling processes, detergents, baking processes, beverages and in oilfields (fuel ethanol).

Alterations in properties which may be achieved in variants of the invention are alterations in, e.g., substrate specificity, substrate binding, substrate cleavage pattern, thermal stability, pH/activity profile, pH/stability profile, such as increased stability at low (e.g. pH<6, in particular pH<5) or high (e.g. pH>9) pH values], stability towards oxidation, $Ca^{2+}$ dependency, specific activity, and other properties of interest. For instance, the alteration may result in a variant which, as compared to the parent amylase, has a reduced $Ca^{2+}$ dependency and/or an altered pH/activity profile.

Figure 6A:
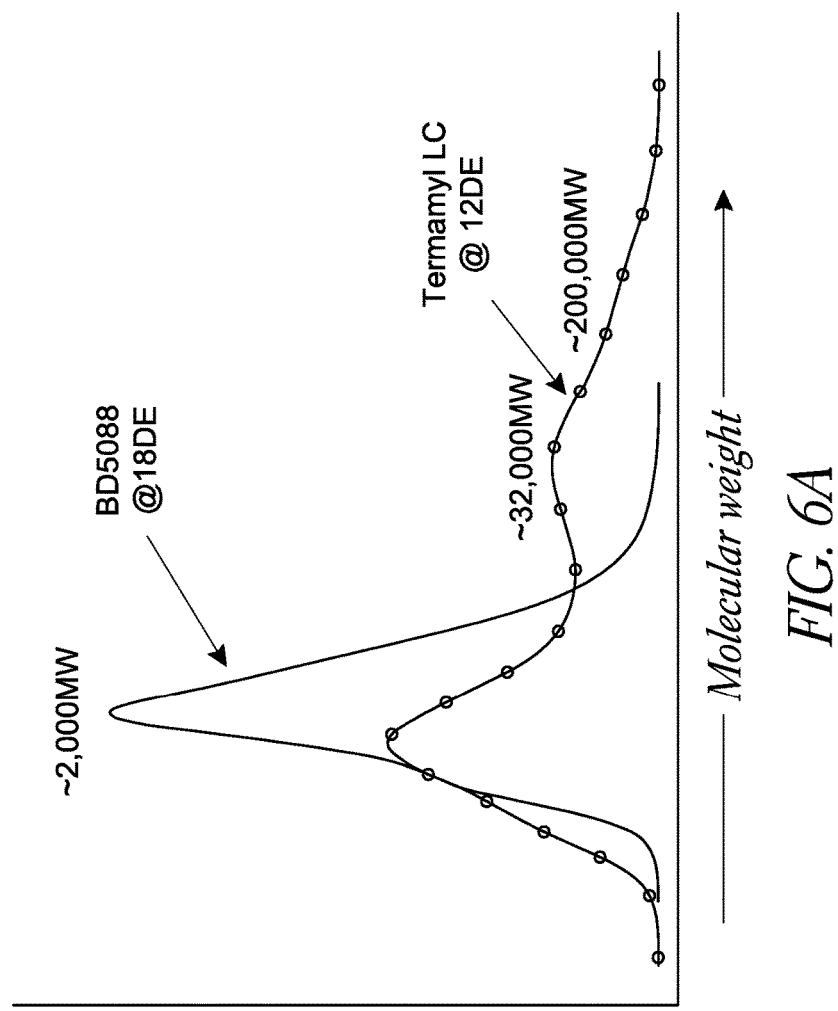
FIGS. 6A and 6B show the molecular weight fragments in syrups using enzymes of the invention and commercial enzymes, as discussed below.
Figure 6B:
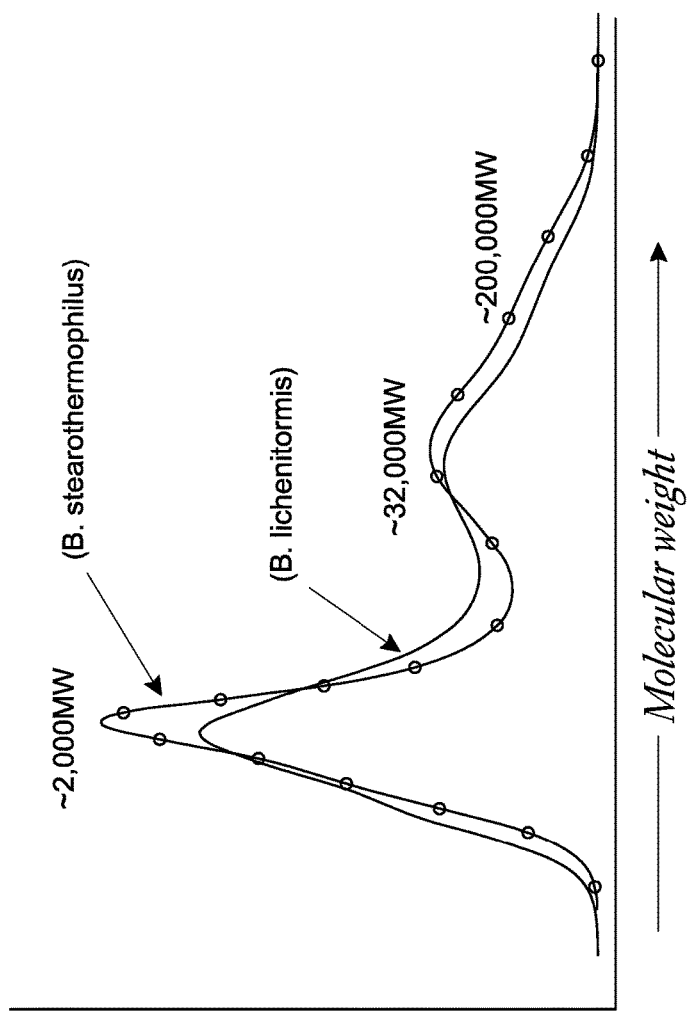
Figure 8:
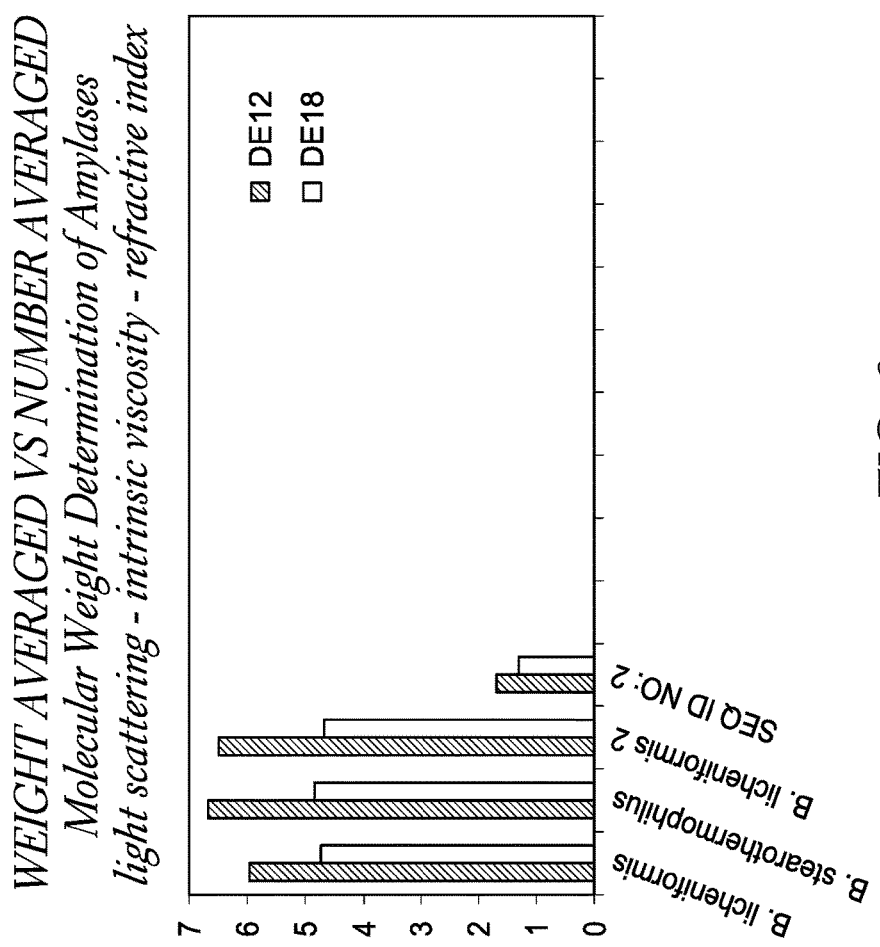
FIG. 8 shows a comparison of oligosaccharide profiles for SEQ ID NO:2 and commercial amylases.

Corn wet milling is a process which produces corn oil, gluten meal, gluten feed and starch. Amylases of the invention, including SEQ ID NO:2, are used in the liquefaction of starch and glucoamylase is used in saccharification, producing glucose. The properties of the amylases of the present invention are unique in that they allow production of liquefied syrups which can be converted to higher dextrose levels than a conventional *Bacillus* amylase liquefied syrup. As can be seen in FIG. 6a and FIG. 6b and in the Examples, the molecular weight profile of liquefied starch produced by commercial amylases derived from *Bacillus licheniformis* and *Bacillus stearothermophilus* exhibit a bimodal distribution with a primary peak at 1000-2000 MW representing approximately 60% of the mass with a secondary peak at 30,000-40,000 MW. In addition, there is a substantial fraction at greater than 100,000 MW. The amylases of the invention exhibit a homogeneous MW distribution centered at 1000-2000 MW with less than 10% of the mass greater than 25,000 MW. The higher MW oligosaccharides are not fully converted to glucose during saccharification. Consequently, the commercial amylases will contain less dextrose than saccharified syrups from the liquefaction process carried out by amylase enzymes of the present invention, such as that represented in SEQ ID NO:2 and functional equivalents thereof.

Maltodextrins are utilized in a wide variety of food and coating applications. Amylases from Archeal sources generate an extremely uniform maltodextrin composition (see also Leveque et al., Enzyme and Microbial Technology 26:3-14, 2000, herein incorporated by reference). The use of the amylases of the invention to liquefy corn starch results in a uniform maltodextrin composition. The liquefaction can be performed at a pH of about 4.5-6.5, and preferably around pH 5.0 and at temperatures of up to 105 degrees C. or higher. In one aspect, the liquefaction is performed at a pH of 4.5.

In addition to the benefits demonstrated in saccharification, the liquefied syrups can be carbon treated, spray dried and utilized as food additives, thickeners, low caloric bulking agents, film forming agents, etc. It is anticipated (but not yet proven) that the homogenous molecular weight profile maltodextrins will have performance advantages vs. the bimodal distribution maltodextrins produced by the conventional *Bacillus* enzymes.

Definitions

The term "amylase" includes all polypeptides, e.g., enzymes, which catalyze the hydrolysis of starches. For example, an amylase activity of the invention includes α-amylase activity, including the ability to hydrolyze internal alpha-1,4-glucosidic linkages in starch to produce smaller molecular weight malto-dextrins. In one aspect, the α-amylase activity includes hydrolyzing internal alpha-1,4-glucosidic linkages in starch at random. An amylase activity of the invention includes polypeptides having glucoamylase activity, such as the ability to hydrolase glucose polymers linked by α-1,4- and α-1,6-glucosidic bonds. In one aspect, the polypeptides of the invention have glucoamylase activity, hydrolyzing internal α-1,4-glucosidic linkages to yield smaller molecular weight malto-dextrins. An amylase activity of the invention also includes glucan 1,4-α-glucosidase activity, or, 1,4-α-D-glucan glucohydrolase, commonly called glucoamylase but also called amyloglucosidase and γ-amylase that, in one aspect, releases 3-D-glucose from 1,4-α-, 1,6-α- and 1,3-α-linked glucans. An amylase activity of the invention also includes exo-amylase activity. An amylase activity of the invention also includes hydrolyzing starch at high temperatures, low temperatures, alkaline pHs and at acidic pHs. An "amylase variant" comprises an amino acid sequence which is derived from the amino acid sequence of a "precursor amylase". The precursor amylase can include naturally-occurring amylases and recombinant amylases. The amino acid sequence of the amylase variant can be "derived" from the precursor amylase amino acid sequence by the substitution, deletion or insertion of one or more amino acids of the precursor amino acid sequence. Such modification can be of the "precursor DNA sequence" which encodes the amino acid sequence of the precursor amylase rather than manipulation of the precursor amylase enzyme per se. Suitable methods for such manipulation of the precursor DNA sequence include methods disclosed herein, as well as methods known to those skilled in the art.

Liquefaction" or "liquefy" means a process by which starch is converted to shorter chain and less viscous dextrins. Generally, this process involves gelatinization of starch simultaneously with or followed by the addition of alpha amylase. In commercial processes, it is preferred that the granular starch is derived from a source comprising corn, wheat, milo, sorghum, rye or bulgher. However, the present invention applies to any grain starch source which is useful in liquefaction, e.g., any other grain or vegetable source known to produce starch suitable for liquefaction.

"Granular starch" or "starch granules" means a water-insoluble component of edible grains which remains after removal of the hull, fiber, protein, fat, germ, and solubles through the steeping, mechanical cracking, separations, screening, countercurrent rinsing and centrifugation steps typical of the grain wet-milling process. Granular starch comprises intact starch granules containing, almost exclusively, packed starch molecules (i.e., amylopectin and amylose). In corn, the granular starch component comprises about 99% starch; the remaining 1% being comprised of protein, fat, ash, fiber and trace components tightly associated with the granules. The packing structure of granular starch severely retards the ability of .alpha.-amylase to hydrolyze starch. Gelatinization of the starch is utilized to disrupt the granules to form a soluble starch solution and facilitate enzymatic hydrolysis.

"Starch solution" means the water soluble gelatinized starch which results from heating granular starch. Upon heating of the granules to above about 72 degrees C., granular starch dissociates to form an aqueous mixture of loose starch molecules. This mixture comprising, for example, about 75% amylopectin and 25% amylose in yellow dent corn forms a viscous solution in water. In commercial processes to form glucose or fructose, it is the starch solution which is liquefied to form a soluble dextrin solution. "alpha amylase" means an enzymatic activity which cleaves or hydrolyzes the alpha (1-4) glycosidic bond, e.g., that in starch, amylopectin or amylose polymers. Suitable alpha amylases are the naturally occurring alpha amylases as well as recombinant or mutant amylases which are useful in liquefaction of starch. Techniques for producing variant amylases having activity at a pH or temperature, for example, that is different from the wild-type amylase, are included herein.

In practicing the invention, the temperature range of the liquefaction can be any liquefaction temperature which is known to be effective in liquefying starch. The temperature of the starch can be between about 80° C. to about 115° C., or from about 100° C. to about 110° C., and/or from about 105° C. to about 108° C.

The term "antibody" includes a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

The terms "array" or "microarray" or "biochip" or "chip" as used herein is a plurality of target elements, each target element comprising a defined amount of one or more polypeptides (including antibodies) or nucleic acids immobilized onto a defined area of a substrate surface, as discussed in further detail, below.

As used herein, the terms "computer," "computer program" and "processor" are used in their broadest general contexts and incorporate all such devices, as described in detail, below. A "coding sequence of" or a "sequence encodes" a particular polypeptide or protein, is a nucleic acid sequence which is transcribed and translated into a polypeptide or protein when placed under the control of appropriate regulatory sequences.

The term "expression cassette" as used herein refers to a nucleotide sequence which is capable of affecting expression of a structural gene (i.e., a protein coding sequence, such as an amylase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers. Thus, expression cassettes also include plasmids, expression vectors, recombinant viruses, any form of recombinant "naked DNA" vector, and the like.

"Operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

As used herein, the term "promoter" includes all sequences capable of driving transcription of a coding sequence in a cell, e.g., a plant cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

"Tissue-specific" promoters are transcriptional control elements that are only active in particular cells or tissues or organs, e.g., in plants or animals. Tissue-specific regulation may be achieved by certain intrinsic factors which ensure that genes encoding proteins specific to a given tissue are expressed. Such factors are known to exist in mammals and plants so as to allow for specific tissues to develop.

The term "plant" includes whole plants, plant parts (e.g., leaves, stems, flowers, roots, etc.), plant protoplasts, seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous states. As used herein, the term "transgenic plant" includes plants or plant cells into which a heterologous nucleic acid sequence has been inserted, e.g., the nucleic acids and various recombinant constructs (e.g., expression cassettes) of the invention.

"Plasmids" can be commercially available, publicly available on an unrestricted basis, or can be constructed from available plasmids in accord with published procedures. Equivalent plasmids to those described herein are known in the art and will be apparent to the ordinarily skilled artisan.

The term "gene" includes a nucleic acid sequence comprising a segment of DNA involved in producing a transcription product (e.g., a message), which in turn is translated to produce a polypeptide chain, or regulates gene transcription, reproduction or stability. Genes can include regions preceding and following the coding region, such as leader and trailer, promoters and enhancers, as well as, where applicable, intervening sequences (introns) between individual coding segments (exons).

The phrases "nucleic acid" or "nucleic acid sequence" includes oligonucleotide, nucleotide, polynucleotide, or to a fragment of any of these, to DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

"Amino acid" or "amino acid sequence" include an oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like. The term also includes glycosylated polypeptides. The peptides and polypeptides of the invention also include all "mimetic" and "peptidomimetic" forms, as described in further detail, below.

The term "isolated" includes a material removed from its original environment, e.g., the natural environment if it is naturally occurring. For example, a naturally occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids which have been purified from genomic DNA or from other sequences in a library or other environment by at least one, two, three, four, five or more orders of magnitude.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the invention include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 10%, 15%, 20%, 30%, 40%, 50%, 60%, 70%, 80%, 90%, 95%, 98% or more of the number of nucleic acid inserts in the population of recombinant backbone molecules. "Recombinant" polypeptides or proteins refer to polypeptides or proteins produced by recombinant DNA techniques; e.g., produced from cells transformed by an exogenous DNA construct encoding the desired polypeptide or protein. "Synthetic" polypeptides or protein are those prepared by chemical synthesis, as described in further detail, below.

A promoter sequence can be "operably linked to" a coding sequence when RNA polymerase which initiates transcription at the promoter will transcribe the coding sequence into mRNA, as discussed further, below.

"Oligonucleotide" includes either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide can ligate to a fragment that has not been dephosphorylated.

The phrase "substantially identical" in the context of two nucleic acids or polypeptides, can refer to two or more sequences that have, e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more nucleotide or amino acid residue (sequence) identity, when compared and aligned for maximum correspondence, as measured using one any known sequence comparison algorithm, as discussed in detail below, or by visual inspection. In alternative aspects, the invention provides nucleic acid and polypeptide sequences having substantial identity to an exemplary sequence of the invention, e.g., SEQ ID NO:1, SEQ ID NO:2, over a region of at least about 10, 20, 30, 40, 50, 100, 150, 200, 250, 300, 350, 400, 450, 500, 550, 600, 650, 700, 750, 800, 850, 900, 950, 1000 or more residues, or a region ranging from between about 50 residues to the full length of the nucleic acid or polypeptide. Nucleic acid sequences of the invention can be substantially identical over the entire length of a polypeptide coding region.

A "substantially identical" amino acid sequence also can include a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an amylase, resulting in modification of the structure of the polypeptide, without significantly altering its biological activity. For example, amino- or carboxyl-terminal amino acids that are not required for amylase activity can be removed.

"Hybridization" includes the process by which a nucleic acid strand joins with a complementary strand through base pairing. Hybridization reactions can be sensitive and selective so that a particular sequence of interest can be identified even in samples in which it is present at low concentrations. Stringent conditions can be defined by, for example, the concentrations of salt or formamide in the prehybridization and hybridization solutions, or by the hybridization temperature, and are well known in the art. For example, stringency can be increased by reducing the concentration of salt, increasing the concentration of formamide, or raising the hybridization temperature, altering the time of hybridization, as described in detail, below. In alternative aspects, nucleic acids of the invention are defined by their ability to hybridize under various stringency conditions (e.g., high, medium, and low), as set forth herein.

"Variant" includes polynucleotides or polypeptides of the invention modified at one or more base pairs, codons, introns, exons, or amino acid residues (respectively) yet still retain the biological activity of an amylase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM and any combination thereof. Techniques for producing variant amylase having activity at a pH or temperature, for example, that is different from a wild-type amylase, are included herein.

The term "saturation mutagenesis" or "GSSM" includes a method that uses degenerate oligonucleotide primers to introduce point mutations into a polynucleotide, as described in detail, below.

The term "optimized directed evolution system" or "optimized directed evolution" includes a method for reassembling fragments of related nucleic acid sequences, e.g., related genes, and explained in detail, below.

The term "synthetic ligation reassembly" or "SLR" includes a method of ligating oligonucleotide fragments in a non-stochastic fashion, and explained in detail, below.

Generating and Manipulating Nucleic Acids

The invention provides nucleic acids, including expression cassettes such as expression vectors, encoding the polypeptides of the invention. The invention also includes methods for discovering new amylase sequences using the nucleic acids of the invention. The invention also includes methods for inhibiting the expression of amylase genes, transcripts and polypeptides using the nucleic acids of the invention. Also provided are methods for modifying the nucleic acids of the invention by, e.g., synthetic ligation reassembly, optimized directed evolution system and/or saturation mutagenesis.

The nucleic acids of the invention can be made, isolated and/or manipulated by, e.g., cloning and expression of cDNA libraries, amplification of message or genomic DNA by PCR, and the like. In practicing the methods of the invention, homologous genes can be modified by manipulating a template nucleic acid, as described herein. The invention can be practiced in conjunction with any method or protocol or device known in the art, which are well described in the scientific and patent literature.

General Techniques

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect or plant cell expression systems.

Alternatively, these nucleic acids can be synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods of the invention is to clone from genomic samples, and, if desired, screen and re-clone inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In one aspect, a nucleic acid encoding a polypeptide of the invention is assembled in appropriate phase with a leader sequence capable of directing secretion of the translated polypeptide or fragment thereof.

The invention provides fusion proteins and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Transcriptional and Translational Control Sequences

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector. Exemplary bacterial promoters include lad, lacZ, T3, T7, gpt, lambda PR, PL and trp. Exemplary eukaryotic promoters include CMV immediate early, HSV thymidine kinase, early and late SV40, LTRs from retrovirus, and mouse metallothionein I.

Promoters suitable for expressing a polypeptide in bacteria include the *E. coli* lac or trp promoters, the lad promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), and the acid phosphatase promoter. Eukaryotic promoters include the CMV immediate early promoter, the HSV thymidine kinase promoter, heat shock promoters, the early and late SV40 promoter, LTRs from retroviruses, and the mouse metallothionein-I promoter. Other promoters known to control expression of genes in prokaryotic or eukaryotic cells or their viruses may also be used.

Tissue-Specific Plant Promoters

The invention provides expression cassettes that can be expressed in a tissue-specific manner, e.g., that can express an amylase of the invention in a tissue-specific manner. The invention also provides plants or seeds that express an amylase of the invention in a tissue-specific manner. The tissue-specificity can be seed specific, stem specific, leaf specific, root specific, fruit specific and the like.

In one aspect, a constitutive promoter such as the CaMV 35S promoter can be used for expression in specific parts of the plant or seed or throughout the plant. For example, for overexpression, a plant promoter fragment can be employed which will direct expression of a nucleic acid in some or all tissues of a plant, e.g., a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Such genes include, e.g., ACT11 from *Arabidopsis* (Huang (1996) Plant Mol. Biol. 33:125-139); Cat3 from *Arabidopsis* (GenBank No. U43147, Zhong (1996) Mol. Gen. Genet. 251:196-203); the gene encoding stearoyl-acyl carrier protein desaturase from *Brassica napus* (Genbank No. X74782, Solocombe (1994) Plant Physiol. 104:1167-1176); GPc1 from maize (GenBank No. X15596; Martinez (1989) J. Mol. Biol 208:551-565); the Gpc2 from maize (GenBank No. U45855, Manjunath (1997) Plant Mol. Biol. 33:97-112); plant promoters described in U.S. Pat. Nos. 4,962,028; 5,633,440.

The invention uses tissue-specific or constitutive promoters derived from viruses which can include, e.g., the tobamovirus subgenomic promoter (Kumagai (1995) Proc. Natl. Acad. Sci. USA 92:1679-1683; the rice tungro baciliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) Plant Mol. Biol. 31:1129-1139).

Alternatively, the plant promoter may direct expression of amylase-expressing nucleic acid in a specific tissue, organ or cell type (i.e. tissue-specific promoters) or may be otherwise under more precise environmental or developmental control or under the control of an inducible promoter. Examples of environmental conditions that may affect transcription include anaerobic conditions, elevated temperature, the presence of light, or sprayed with chemicals/hormones. For example, the invention incorporates the drought-inducible promoter of maize (Busk (1997) supra); the cold, drought, and high salt inducible promoter from potato (Kirch (1997) Plant Mol. Biol. 33:897 909).

Tissue-specific promoters can promote transcription only within a certain time frame of developmental stage within that tissue. See, e.g., Blazquez (1998) Plant Cell 10:791-800, characterizing the *Arabidopsis* LEAFY gene promoter. See also Cardon (1997) *Plant J* 12:367-77, describing the transcription factor SPL3, which recognizes a conserved sequence motif in the promoter region of the *A. thaliana* floral meristem identity gene AP1; and Mandel (1995) Plant Molecular Biology, Vol. 29, pp 995-1004, describing the meristem promoter eIF4. Tissue specific promoters which are active throughout the life cycle of a particular tissue can be used. In one aspect, the nucleic acids of the invention are operably linked to a promoter active primarily only in cotton fiber cells. In one aspect, the nucleic acids of the invention are operably linked to a promoter active primarily during the stages of cotton fiber cell elongation, e.g., as described by Rinehart (1996) supra. The nucleic acids can be operably linked to the Fbl2A gene promoter to be preferentially expressed in cotton fiber cells (Ibid). See also, John (1997) Proc. Natl. Acad. Sci. USA 89:5769-5773; John, et al., U.S. Pat. Nos. 5,608,148 and 5,602,321, describing cotton fiber-specific promoters and methods for the construction of transgenic cotton plants. Root-specific promoters may also be used to express the nucleic acids of the invention. Examples of root-specific promoters include the promoter from the alcohol dehydrogenase gene (DeLisle (1990) Int. Rev. Cytol. 123:39-60). Other promoters that can be used to express the nucleic acids of the invention include, e.g., ovule-specific, embryo-specific, endosperm-specific, integument-specific, seed coat-specific promoters, or some combination thereof; a leaf-specific promoter (see, e.g., Busk (1997) Plant J. 11:1285 1295, describing a leaf-specific promoter in maize); the ORF13 promoter from *Agrobacterium rhizogenes* (which exhibits high activity in roots, see, e.g., Hansen (1997) supra); a maize pollen specific promoter (see, e.g., Guerrero (1990) Mol. Gen. Genet. 224:161 168); a tomato promoter active during fruit ripening, senescence and abscission of leaves and, to a lesser extent, of flowers can be used (see, e.g., Blume (1997) Plant J. 12:731 746); a pistil-specific promoter from the potato SK2 gene (see, e.g., Ficker (1997) Plant Mol. Biol. 35:425 431); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BEL1 gene (see, e.g., Reiser (1995) Cell 83:735-742, GenBank No. U39944); and/or, the promoter in Klee, U.S. Pat. No. 5,589,583, describing a plant promoter region is capable of conferring high levels of transcription in meristematic tissue and/or rapidly dividing cells.

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (Sheen (1996) Science 274:1900-1902).

The nucleic acids of the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324). Using chemically- (e.g., hormone- or pesticide-) induced promoters, i.e., promoter responsive to a chemical which can be applied to the transgenic plant in the field, expression of a polypeptide of the invention can be induced at a particular stage of development of the plant. Thus, the invention also provides for transgenic plants containing an inducible gene encoding for polypeptides of the invention whose host range is limited to target plant species, such as corn, rice, barley, wheat, potato or other crops, inducible at any stage of development of the crop.

One of skill will recognize that a tissue-specific plant promoter may drive expression of operably linked sequences in tissues other than the target tissue. Thus, a tissue-specific promoter is one that drives expression preferentially in the target tissue or cell type, but may also lead to some expression in other tissues as well.

The nucleic acids of the invention can also be operably linked to plant promoters which are inducible upon exposure to chemicals reagents. These reagents include, e.g., herbicides, synthetic auxins, or antibiotics which can be applied, e.g., sprayed, onto transgenic plants. Inducible expression of the amylase-producing nucleic acids of the invention will allow the grower to select plants with the optimal starch/sugar ratio. The development of plant parts can thus controlled. In this way the invention provides the means to facilitate the harvesting of plants and plant parts. For example, in various embodiments, the maize In2-2 promoter, activated by benzenesulfonamide herbicide safeners, is used (De Veylder (1997) Plant Cell Physiol. 38:568-577); application of different herbicide safeners induces distinct gene expression patterns, including expression in the root, hydathodes, and the shoot apical meristem. Coding sequences of the invention are also under the control of a tetracycline-inducible promoter, e.g., as described with transgenic tobacco plants containing the *Avena sativa* L. (oat) arginine decarboxylase gene (Masgrau (1997) Plant J. 11:465-473); or, a salicylic acid-responsive element (Stange (1997) Plant J. 11:1315-1324).

If proper polypeptide expression is desired, a polyadenylation region at the 3'-end of the coding region should be included. The polyadenylation region can be derived from the natural gene, from a variety of other plant genes, or from genes in the Agrobacterial T-DNA.

Expression Vectors and Cloning Vehicles

The invention provides expression vectors and cloning vehicles comprising nucleic acids of the invention, e.g., sequences encoding the amylases of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available. Exemplary vectors are include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present invention.

The expression vector can comprise a promoter, a ribosome binding site for translation initiation and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some aspects, DNA sequences derived from the SV40 splice and polyadenylation sites may be used to provide the required non-transcribed genetic elements.

In one aspect, the expression vectors contain one or more selectable marker genes to permit selection of host cells containing the vector. Such selectable markers include genes encoding dihydrofolate reductase or genes conferring neomycin resistance for eukaryotic cell culture, genes conferring tetracycline or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook. Such procedures and others are deemed to be within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by, e.g., Sambrook.

Particular bacterial vectors which can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pKK233-3, DR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

The nucleic acids of the invention can be expressed in expression cassettes, vectors or viruses and transiently or stably expressed in plant cells and seeds. One exemplary transient expression system uses episomal expression systems, e.g., cauliflower mosaic virus (CaMV) viral RNA generated in the nucleus by transcription of an episomal mini-chromosome containing supercoiled DNA, see, e.g., Covey (1990) Proc. Natl. Acad. Sci. USA 87:1633-1637. Alternatively, coding sequences, i.e., all or sub-fragments of sequences of the invention can be inserted into a plant host cell genome becoming an integral part of the host chromosomal DNA. Sense or antisense transcripts can be expressed in this manner. A vector comprising the sequences (e.g., promoters or coding regions) from nucleic acids of the invention can comprise a marker gene that confers a selectable phenotype on a plant cell or a seed. For example, the marker may encode biocide resistance, particularly antibiotic resistance, such as resistance to kanamycin, G418, bleomycin, hygromycin, or herbicide resistance, such as resistance to chlorosulfuron or Basta.

Expression vectors capable of expressing nucleic acids and proteins in plants are well known in the art, and can include, e.g., vectors from *Agrobacterium* spp., potato virus X (see, e.g., Angell (1997) EMBO J. 16:3675-3684), tobacco mosaic virus (see, e.g., Casper (1996) Gene 173: 69-73), tomato bushy stunt virus (see, e.g., Hillman (1989) Virology 169:42-50), tobacco etch virus (see, e.g., Dolja (1997) Virology 234:243-252), bean golden mosaic virus (see, e.g., Morinaga (1993) Microbiol Immunol. 37:471-476), cauliflower mosaic virus (see, e.g., Cecchini (1997) Mol. Plant Microbe Interact. 10:1094-1101), maize Ac/Ds transposable element (see, e.g., Rubin (1997) Mol. Cell. Biol. 17:6294-6302; Kunze (1996) Curr. Top. Microbiol. Immunol. 204:161-194), and the maize suppressor-mutator (Spm) transposable element (see, e.g., Schlappi (1996) Plant Mol. Biol. 32:717-725); and derivatives thereof.

In one aspect, the expression vector can have two replication systems to allow it to be maintained in two organisms, for example in mammalian or insect cells for expression and in a prokaryotic host for cloning and amplification. Furthermore, for integrating expression vectors, the expression vector can contain at least one sequence homologous to the host cell genome. It can contain two homologous sequences which flank the expression construct. The integrating vector can be directed to a specific locus in the host cell by selecting the appropriate homologous sequence for inclusion in the vector. Constructs for integrating vectors are well known in the art.

Expression vectors of the invention may also include a selectable marker gene to allow for the selection of bacterial strains that have been transformed, e.g., genes which render the bacteria resistant to drugs such as ampicillin, chloramphenicol, erythromycin, kanamycin, neomycin and tetracycline. Selectable markers can also include biosynthetic genes, such as those in the histidine, tryptophan and leucine biosynthetic pathways.

Host Cells and Transformed Cells

The invention also provides a transformed cell comprising a nucleic acid sequence of the invention, e.g., a sequence encoding an amylase of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art. Techniques for transforming a wide variety of higher plant species are well known and described in the technical and scientific literature. See, e.g., Weising (1988) Ann. Rev. Genet. 22:421-477, U.S. Pat. No. 5,750,870.

The vector can be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation (Davis, L., Dibner, M., Battey, I., Basic Methods in Molecular Biology, (1986)).

In one aspect, the nucleic acids or vectors of the invention are introduced into the cells for screening, thus, the nucleic acids enter the cells in a manner suitable for subsequent expression of the nucleic acid. The method of introduction is largely dictated by the targeted cell type. Exemplary methods include $CaPO_4$ precipitation, liposome fusion, lipofection (e.g., LIPOFECTIN™), electroporation, viral infection, etc. The candidate nucleic acids may stably integrate into the genome of the host cell (for example, with retroviral introduction) or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting such targets are preferred.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Amplification of Nucleic Acids

In practicing the invention, nucleic acids of the invention and nucleic acids encoding the polypeptides of the invention, or modified nucleic acids of the invention, can be reproduced by amplification. Amplification can also be used to clone or modify the nucleic acids of the invention. Thus, the invention provides amplification primer sequence pairs for amplifying nucleic acids of the invention. One of skill in the art can design amplification primer sequence pairs for any part of or the full length of these sequences.

Amplification reactions can also be used to quantify the amount of nucleic acid in a sample (such as the amount of message in a cell sample), label the nucleic acid (e.g., to apply it to an array or a blot), detect the nucleic acid, or quantify the amount of a specific nucleic acid in a sample. In one aspect of the invention, message isolated from a cell or a cDNA library are amplified.

The skilled artisan can select and design suitable oligonucleotide amplification primers. Amplification methods are also well known in the art, and include, e.g., polymerase chain reaction, PCR (see, e.g., PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477-1491), automated Q-beta replicase amplification assay (see, e.g., Burg (1996) Mol. Cell. Probes 10:257-271) and other RNA polymerase mediated techniques (e.g., NASBA, Cangene, Mississauga, Ontario); see also Berger (1987) Methods Enzymol. 152:307-316; Sambrook; Ausubel; U.S. Pat. Nos. 4,683,195 and 4,683,202; Sooknanan (1995) Biotechnology 13:563-564.

Determining the Degree of Sequence Identity

The invention provides nucleic acids comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary nucleic acid of the invention over a region of at least about 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550 or more, residues. The invention provides polypeptides comprising sequences having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity to an exemplary polypeptide of the invention. The extent of sequence identity (homology) may be determined using any computer program and associated parameters, including those described herein, such as BLAST 2.2.2. or FASTA version 3.0t78, with the default parameters.

Homologous sequences also include RNA sequences in which uridines replace the thymines in the nucleic acid sequences. The homologous sequences may be obtained using any of the procedures described herein or may result from the correction of a sequencing error. It will be appreciated that the nucleic acid sequences as set forth herein can be represented in the traditional single character format (see, e.g., Stryer, Lubert. Biochemistry, 3rd Ed., W. H Freeman & Co., New York) or in any other format which records the identity of the nucleotides in a sequence.

Various sequence comparison programs identified herein are used in this aspect of the invention. Protein and/or nucleic acid sequence identities (homologies) may be evaluated using any of the variety of sequence comparison algorithms and programs known in the art. Such algorithms and programs include, but are not limited to, TBLASTN, BLASTP, FASTA, TFASTA, and CLUSTALW (Pearson and Lipman, Proc. Natl. Acad. Sci. USA 85(8):2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993).

Homology or identity can be measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence, e.g., a sequence of the invention, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, contiguous residues ranging anywhere from 20 to the full length of an exemplary polypeptide or nucleic acid sequence of the invention are compared to a reference sequence of the same number of contiguous positions after the two sequences are optimally aligned. If the reference sequence has the requisite sequence identity to an exemplary polypeptide or nucleic acid sequence of the invention, e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more sequence identity to a sequence of the invention, that sequence is within the scope of the invention. In alternative embodiments, subsequences ranging from about 20 to 600, about 50 to 200, and about 100 to 150 are compared to a reference sequence of the same number of contiguous positions after the two sequences are optimally aligned. Methods of alignment of sequence for comparison are well known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (Gibbs, 1995). Several genomes have been sequenced, e.g., *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Databases containing genomic information annotated with some functional information are maintained by different organizations, and are accessible via the internet.

BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1990) supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff (1989) Proc. Natl. Acad. Sci. USA 89:10915) alignments (B) of 50, expectation (E) of 10, M=5, N=−4, and a comparison of both strands. The BLAST algorithm also performs a statistical analysis of the similarity between two sequences (see, e.g., Karlin & Altschul (1993) Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001. In one aspect, protein and nucleic acid sequence homologies are evaluated using the Basic Local Alignment Search Tool ("BLAST"). For example, five specific BLAST programs can be used to perform the following task: (1) BLASTP and BLAST3 compare an amino acid query sequence against a protein sequence database; (2) BLASTN compares a nucleotide query sequence against a nucleotide sequence database; (3) BLASTX compares the six-frame conceptual translation products of a query nucleotide sequence (both strands) against a protein sequence database; (4) TBLASTN compares a query protein sequence against a nucleotide sequence database translated in all six reading frames (both strands); and, (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation).

In one aspect of the invention, to determine if a nucleic acid has the requisite sequence identity to be within the scope of the invention, the NCBI BLAST 2.2.2 programs is used, default options to blastp. There are about 38 setting options in the BLAST 2.2.2 program. In this exemplary aspect of the invention, all default values are used except for the default filtering setting (i.e., all parameters set to default except filtering which is set to OFF); in its place a "−F F" setting is used, which disables filtering. Use of default filtering often results in Karlin-Altschul violations due to short length of sequence.

The default values used in this exemplary aspect of the invention include:

"Filter for low complexity: ON
Word Size: 3
Matrix: Blosum62
Gap Costs: Existence:11
Extension:1"

Other default settings can be: filter for low complexity OFF, word size of 3 for protein, BLOSUM62 matrix, gap existence penalty of −11 and a gap extension penalty of −1. An exemplary NCBI BLAST 2.2.2 program setting has the "−W" option default to 0. This means that, if not set, the word size defaults to 3 for proteins and 11 for nucleotides.

Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM) as well as other types of other media known to those skilled in the art.

Aspects of the invention include systems (e.g., internet based systems), particularly computer systems, which store and manipulate the sequences and sequence information described herein. One example of a computer system 100 is illustrated in block diagram form in FIG. 1. As used herein, "a computer system" refers to the hardware components, software components, and data storage components used to analyze a nucleotide or polypeptide sequence of the invention. The computer system 100 can include a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines. The computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one aspect, the computer system 100 includes a processor 105 connected to a bus which is connected to a main memory 115 (preferably implemented as RAM) and one or more internal data storage devices 110, such as a hard drive and/or other computer readable media having data recorded thereon. The computer system 100 can further include one or more data retrieving device 118 for reading the data stored on the internal data storage devices 110. The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device. The computer system 100 includes a display 120 which is used to display output to a computer user. It should also be noted that the computer system 100 can be linked to other computer systems 125a-c in a network or wide area network to provide centralized access to the computer system 100. Software for accessing and processing the nucleotide or amino acid sequences of the invention can reside in main memory 115 during execution. In some aspects, the computer system 100 may further comprise a sequence comparison algorithm for comparing a nucleic acid sequence of the invention. The algorithm and sequence(s) can be stored on a computer readable medium. A "sequence comparison algorithm" refers to one or more programs which are implemented (locally or remotely) on the computer system 100 to compare a nucleotide sequence with other nucleotide sequences and/or compounds stored within a data storage means. For example, the sequence comparison algorithm may compare the nucleotide sequences of the invention stored on a computer readable medium to reference sequences stored on a computer readable medium to identify homologies or structural motifs.

Figure 2:
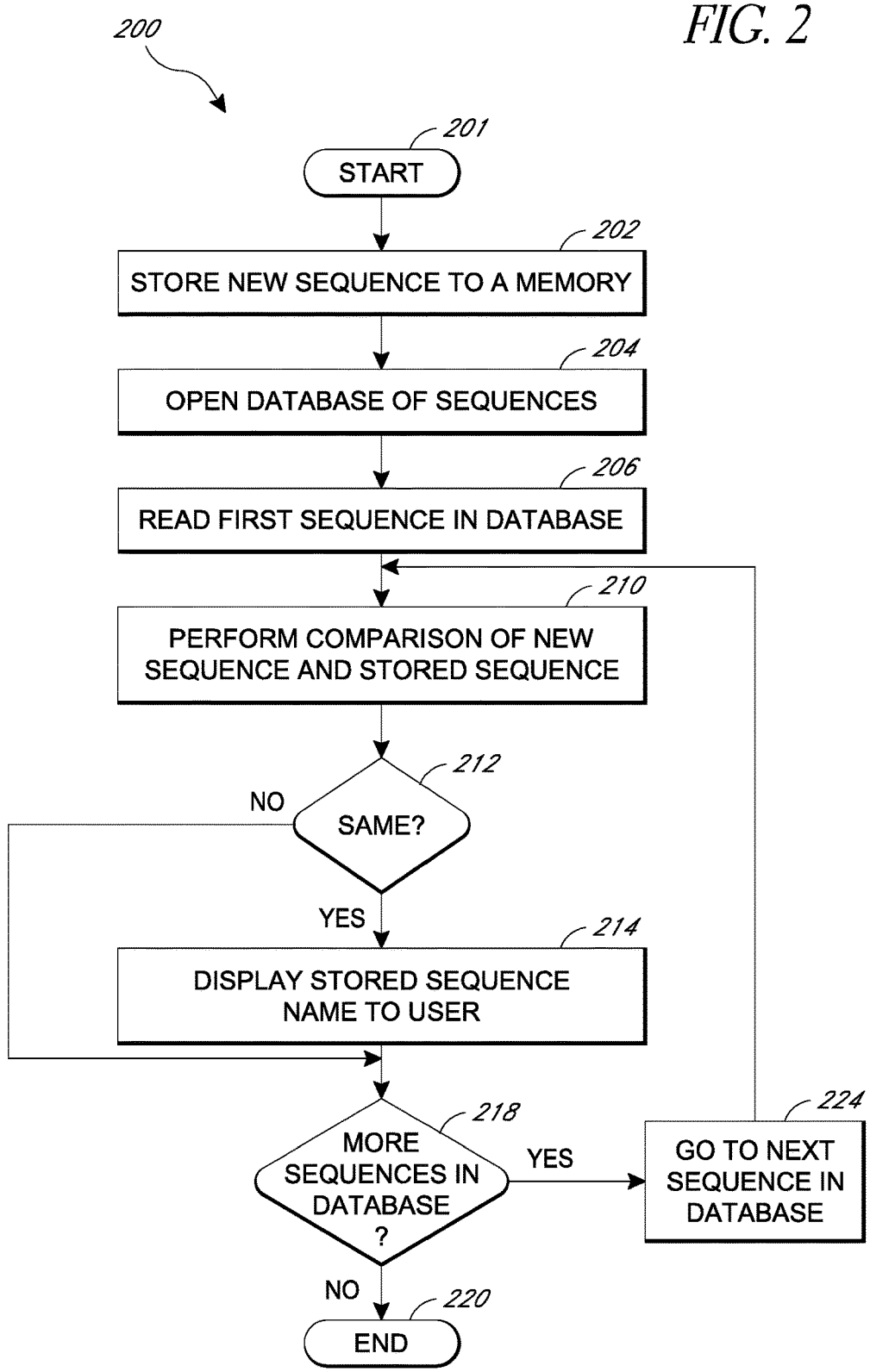
FIG. 2 is a flow diagram illustrating one aspect of a process for comparing a new nucleotide or protein sequence with a database of sequences in order to determine the homology levels between the new sequence and the sequences in the database.
Figure 3:
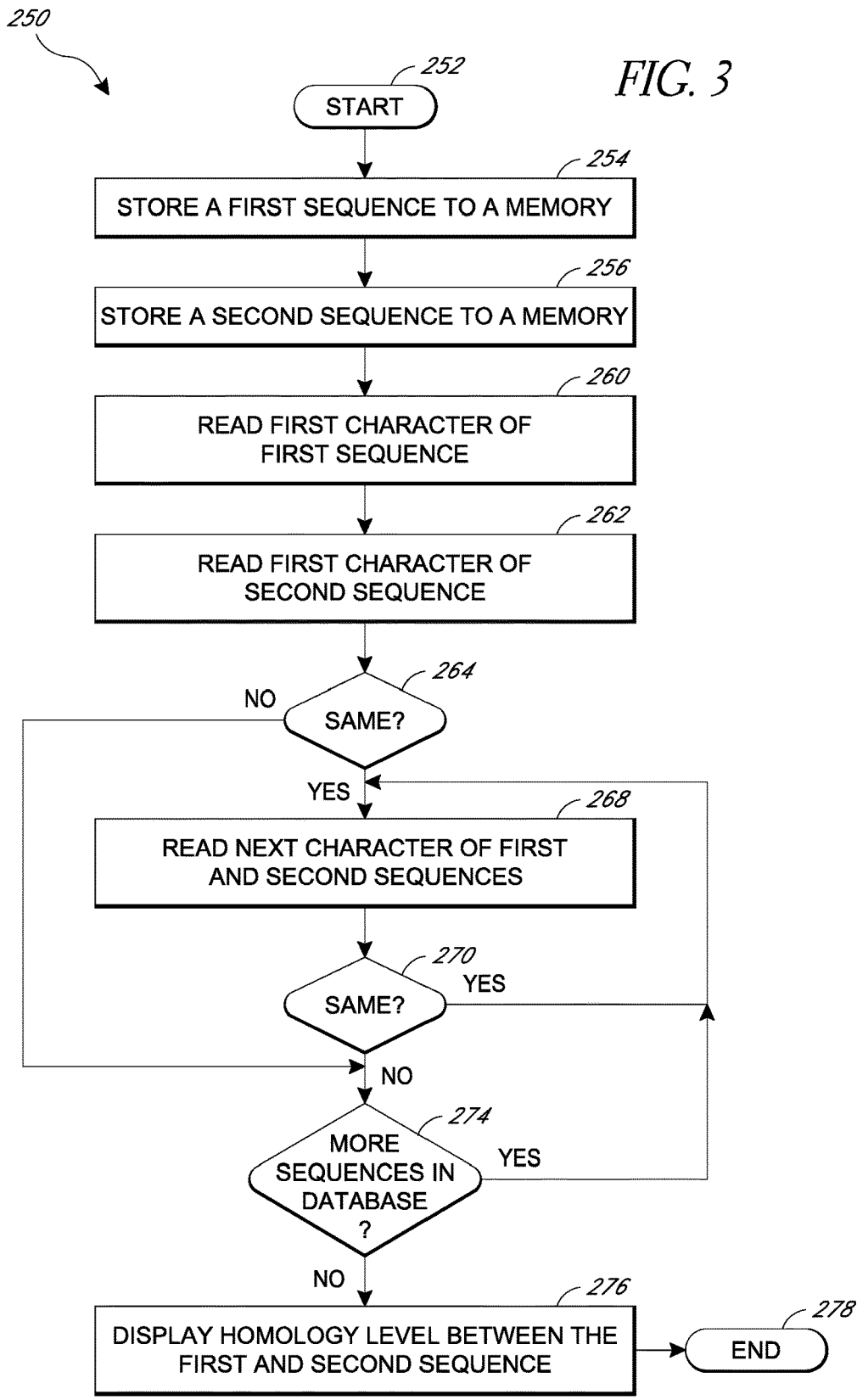
FIG. 3 is a flow diagram illustrating one aspect of a process in a computer for determining whether two sequences are homologous.

The parameters used with the above algorithms may be adapted depending on the sequence length and degree of homology studied. In some aspects, the parameters may be the default parameters used by the algorithms in the absence of instructions from the user. FIG. 2 is a flow diagram illustrating one aspect of a process 200 for comparing a new nucleotide or protein sequence with a database of sequences in order to determine the homology levels between the new sequence and the sequences in the database. The database of sequences can be a private database stored within the computer system 100, or a public database such as GEN-BANK that is available through the Internet. The process 200 begins at a start state 201 and then moves to a state 202 wherein the new sequence to be compared is stored to a memory in a computer system 100. As discussed above, the memory could be any type of memory, including RAM or an internal storage device. The process 200 then moves to a state 204 wherein a database of sequences is opened for analysis and comparison. The process 200 then moves to a state 206 wherein the first sequence stored in the database is read into a memory on the computer. A comparison is then performed at a state 210 to determine if the first sequence is the same as the second sequence. It is important to note that this step is not limited to performing an exact comparison between the new sequence and the first sequence in the database. Well-known methods are known to those of skill in the art for comparing two nucleotide or protein sequences, even if they are not identical. For example, gaps can be introduced into one sequence in order to raise the homology level between the two tested sequences. The parameters that control whether gaps or other features are introduced into a sequence during comparison are normally entered by the user of the computer system. Once a comparison of the two sequences has been performed at the state 210, a determination is made at a decision state 210 whether the two sequences are the same. Of course, the term "same" is not limited to sequences that are absolutely identical. Sequences that are within the homology parameters entered by the user will be marked as "same" in the process 200. If a determination is made that the two sequences are the same, the process 200 moves to a state 214 wherein the name of the sequence from the database is displayed to the user. This state notifies the user that the sequence with the displayed name fulfills the homology constraints that were entered. Once the name of the stored sequence is displayed to the user, the process 200 moves to a decision state 218 wherein a determination is made whether more sequences exist in the database. If no more sequences exist in the database, then the process 200 terminates at an end state 220. However, if more sequences do exist in the database, then the process 200 moves to a state 224 wherein a pointer is moved to the next sequence in the database so that it can be compared to the new sequence. In this manner, the new sequence is aligned and compared with every sequence in the database. It should be noted that if a determination had been made at the decision state 212 that the sequences were not homologous, then the process 200 would move immediately to the decision state 218 in order to determine if any other sequences were available in the database for comparison. Accordingly, one aspect of the invention is a computer system comprising a processor, a data storage device having stored thereon a nucleic acid sequence of the invention and a sequence comparer for conducting the comparison. The sequence comparer may indicate a homology level between the sequences compared or identify structural motifs, or it may identify structural motifs in sequences which are compared to these nucleic acid codes and polypeptide codes. FIG. 3 is a flow diagram illustrating one embodiment of a process 250 in a computer for determining whether two sequences are homologous. The process 250 begins at a start state 252 and then moves to a state 254 wherein a first sequence to be compared is stored to a memory. The second sequence to be compared is then stored to a memory at a state 256. The process 250 then moves to a state 260 wherein the first character in the first sequence is read and then to a state 262 wherein the first character of the second sequence is read. It should be understood that if the sequence is a nucleotide sequence, then the character would normally be either A, T, C, G or U. If the sequence is a protein sequence, then it can be a single letter amino acid code so that the first and sequence sequences can be easily compared. A determination is then made at a decision state 264 whether the two characters are the same. If they are the same, then the process 250 moves to a state 268 wherein the next characters in the first and second sequences are read. A determination is then made whether the next characters are the same. If they are, then the process 250 continues this loop until two characters are not the same. If a determination is made that the next two characters are not the same, the process 250 moves to a decision state 274 to determine whether there are any more characters either sequence to read. If there are not any more characters to read, then the process 250 moves to a state 276 wherein the level of homology between the first and second sequences is displayed to the user. The level of homology is determined by calculating the proportion of characters between the sequences that were the same out of the total number of sequences in the first sequence. Thus, if every character in a first 100 nucleotide sequence aligned with an every character in a second sequence, the homology level would be 100%.

Alternatively, the computer program can compare a reference sequence to a sequence of the invention to determine whether the sequences differ at one or more positions. The program can record the length and identity of inserted, deleted or substituted nucleotides or amino acid residues with respect to the sequence of either the reference or the invention. The computer program may be a program which determines whether a reference sequence contains a single nucleotide polymorphism (SNP) with respect to a sequence of the invention, or, whether a sequence of the invention comprises a SNP of a known sequence. Thus, in some aspects, the computer program is a program which identifies SNPs. The method may be implemented by the computer systems described above and the method illustrated in FIG. 3. The method can be performed by reading a sequence of the invention and the reference sequences through the use of the computer program and identifying differences with the computer program.

Figure 4:
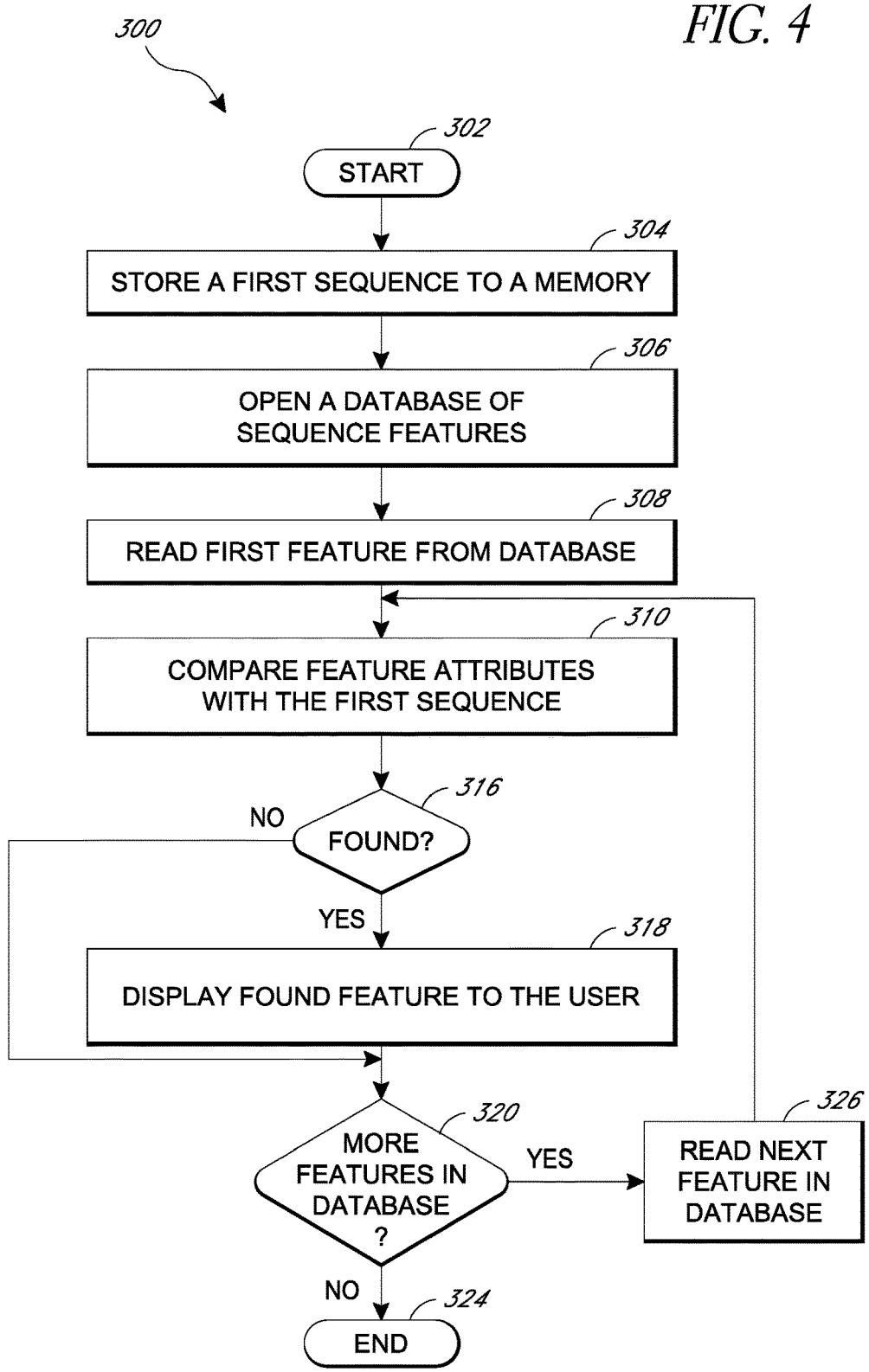
FIG. 4 is a flow diagram illustrating one aspect of an identifier process 300 for detecting the presence of a feature in a sequence.

In other aspects the computer based system comprises an identifier for identifying features within a nucleic acid or polypeptide of the invention. An "identifier" refers to one or more programs which identifies certain features within a nucleic acid sequence. For example, an identifier may comprise a program which identifies an open reading frame (ORF) in a nucleic acid sequence. FIG. 4 is a flow diagram illustrating one aspect of an identifier process 300 for detecting the presence of a feature in a sequence. The process 300 begins at a start state 302 and then moves to a state 304 wherein a first sequence that is to be checked for features is stored to a memory 115 in the computer system 100. The process 300 then moves to a state 306 wherein a database of sequence features is opened. Such a database would include a list of each feature's attributes along with the name of the feature. For example, a feature name could be "Initiation Codon" and the attribute would be "ATG". Another example would be the feature name "TAATAA Box" and the feature attribute would be "TAATAA". An example of such a database is produced by the University of Wisconsin Genetics Computer Group. Alternatively, the features may be structural polypeptide motifs such as alpha helices, beta sheets, or functional polypeptide motifs such as enzymatic active sites, helix-turn-helix motifs or other motifs known to those skilled in the art. Once the database of features is opened at the state 306, the process 300 moves to a state 308 wherein the first feature is read from the database. A comparison of the attribute of the first feature with the first sequence is then made at a state 310. A determination is then made at a decision state 316 whether the attribute of the feature was found in the first sequence. If the attribute was found, then the process 300 moves to a state 318 wherein the name of the found feature is displayed to the user. The process 300 then moves to a decision state 320 wherein a determination is made whether move features exist in the database. If no more features do exist, then the process 300 terminates at an end state 324. However, if more features do exist in the database, then the process 300 reads the next sequence feature at a state 326 and loops back to the state 310 wherein the attribute of the next feature is compared against the first sequence. If the feature attribute is not found in the first sequence at the decision state 316, the process 300 moves directly to the decision state 320 in order to determine if any more features exist in the database. Thus, in one aspect, the invention provides a computer program that identifies open reading frames (ORFs).

A polypeptide or nucleic acid sequence of the invention can be stored and manipulated in a variety of data processor programs in a variety of formats. For example, a sequence can be stored as text in a word processing file, such as MicrosoftWORD or WORDPERFECT or as an ASCII file in a variety of database programs familiar to those of skill in the art, such as DB2, SYBASE, or ORACLE. In addition, many computer programs and databases may be used as sequence comparison algorithms, identifiers, or sources of reference nucleotide sequences or polypeptide sequences to be compared to a nucleic acid sequence of the invention. The programs and databases used to practice the invention include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, J. Mol. Biol. 215: 403, 1990), FASTA (Pearson and Lipman, Proc. Natl. Acad. Sci. USA, 85: 2444, 1988), FASTDB (Brutlag et al. Comp. App. Biosci. 6:237-245, 1990), Catalyst (Molecular Simulations Inc.), Catalyst/SHAPE (Molecular Simulations Inc.), Cerius2.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the MDL Available Chemicals Directory database, the MDL Drug Data Report data base, the Comprehensive Medicinal Chemistry database, Derwent's World Drug Index database, the BioByteMasterFile database, the Genbank database, and the Genseqn database. Many other programs and data bases would be apparent to one of skill in the art given the present disclosure.

Motifs which may be detected using the above programs include sequences encoding leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

Hybridization of Nucleic Acids

The invention provides isolated or recombinant nucleic acids that hybridize under stringent conditions to an exemplary sequence of the invention, or a nucleic acid that encodes a polypeptide of the invention. The stringent conditions can be highly stringent conditions, medium stringent conditions, low stringent conditions, including the high and reduced stringency conditions described herein. In one aspect, it is the stringency of the wash conditions that set forth the conditions which determine whether a nucleic acid is within the scope of the invention, as discussed below.

In alternative embodiments, nucleic acids of the invention as defined by their ability to hybridize under stringent conditions can be between about five residues and the full length of nucleic acid of the invention; e.g., they can be at least 5, 10, 15, 20, 25, 30, 35, 40, 50, 55, 60, 65, 70, 75, 80, 90, 100, 150, 200, 250, 300, 350, 400, 450, 500, 550, 600, 650, 700, 750, 800, 850, 900, 950, 1000, or more, residues in length. Nucleic acids shorter than full length are also included. These nucleic acids can be useful as, e.g., hybridization probes, labeling probes, PCR oligonucleotide probes, iRNA, antisense or sequences encoding antibody binding peptides (epitopes), motifs, active sites and the like.

In one aspect, nucleic acids of the invention are defined by their ability to hybridize under high stringency comprises conditions of about 50% formamide at about 37° C. to 42° C. In one aspect, nucleic acids of the invention are defined by their ability to hybridize under reduced stringency comprising conditions in about 35% to 25% formamide at about 30° C. to 35° C.

Alternatively, nucleic acids of the invention are defined by their ability to hybridize under high stringency comprising conditions at 42° C. in 50% formamide, 5×SSPE, 0.3% SDS, and a repetitive sequence blocking nucleic acid, such as cot-1 or salmon sperm DNA (e.g., 200 n/ml sheared and denatured salmon sperm DNA). In one aspect, nucleic acids of the invention are defined by their ability to hybridize under reduced stringency conditions comprising 35% formamide at a reduced temperature of 35° C.

Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

The temperature range corresponding to a particular level of stringency can be further narrowed by calculating the purine to pyrimidine ratio of the nucleic acid of interest and adjusting the temperature accordingly. Nucleic acids of the invention are also defined by their ability to hybridize under high, medium, and low stringency conditions as set forth in Ausubel and Sambrook. Variations on the above ranges and conditions are well known in the art. Hybridization conditions are discussed further, below.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. A specific example of "moderate" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

These methods may be used to isolate nucleic acids of the invention.

Oligonucleotides Probes and Methods for Using Them

The invention also provides nucleic acid probes that can be used, e.g., for identifying nucleic acids encoding a polypeptide with an amylase activity or fragments thereof or for identifying amylase genes. In one aspect, the probe comprises at least 10 consecutive bases of a nucleic acid of the invention. Alternatively, a probe of the invention can be at least about 5, 6, 7, 8, 9, 10, 15, 20, 25, 30, 35, 40, 45, 50, 60, 70, 80, 90, 100, 110, 120, 130, 150 or about 10 to 50, about 20 to 60 about 30 to 70, consecutive bases of a sequence as set forth in a nucleic acid of the invention. The probes identify a nucleic acid by binding and/or hybridization. The probes can be used in arrays of the invention, see discussion below, including, e.g., capillary arrays. The probes of the invention can also be used to isolate other nucleic acids or polypeptides.

The probes of the invention can be used to determine whether a biological sample, such as a soil sample, contains an organism having a nucleic acid sequence of the invention or an organism from which the nucleic acid was obtained. In such procedures, a biological sample potentially harboring the organism from which the nucleic acid was isolated is obtained and nucleic acids are obtained from the sample. The nucleic acids are contacted with the probe under conditions which permit the probe to specifically hybridize to any complementary sequences present in the sample. Where necessary, conditions which permit the probe to specifically hybridize to complementary sequences may be determined by placing the probe in contact with complementary sequences from samples known to contain the complementary sequence, as well as control sequences which do not contain the complementary sequence. Hybridization conditions, such as the salt concentration of the hybridization buffer, the formamide concentration of the hybridization buffer, or the hybridization temperature, may be varied to identify conditions which allow the probe to hybridize specifically to complementary nucleic acids (see discussion on specific hybridization conditions).

If the sample contains the organism from which the nucleic acid was isolated, specific hybridization of the probe is then detected. Hybridization may be detected by labeling the probe with a detectable agent such as a radioactive isotope, a fluorescent dye or an enzyme capable of catalyzing the formation of a detectable product. Many methods for using the labeled probes to detect the presence of complementary nucleic acids in a sample are familiar to those skilled in the art. These include Southern Blots, Northern Blots, colony hybridization procedures, and dot blots. Protocols for each of these procedures are provided in Ausubel and Sambrook.

Alternatively, more than one probe (at least one of which is capable of specifically hybridizing to any complementary sequences which are present in the nucleic acid sample), may be used in an amplification reaction to determine whether the sample contains an organism containing a nucleic acid sequence of the invention (e.g., an organism from which the nucleic acid was isolated). In one aspect, the probes comprise oligonucleotides. In one aspect, the amplification reaction may comprise a PCR reaction. PCR protocols are described in Ausubel and Sambrook (see discussion on amplification reactions). In such procedures, the nucleic acids in the sample are contacted with the probes, the amplification reaction is performed, and any resulting amplification product is detected. The amplification product may be detected by performing gel electrophoresis on the reaction products and staining the gel with an intercalator such as ethidium bromide. Alternatively, one or more of the probes may be labeled with a radioactive isotope and the presence of a radioactive amplification product may be detected by autoradiography after gel electrophoresis.

Probes derived from sequences near the 3' or 5' ends of a nucleic acid sequence of the invention can also be used in chromosome walking procedures to identify clones containing additional, e.g., genomic sequences. Such methods allow the isolation of genes which encode additional proteins of interest from the host organism.

In one aspect, nucleic acid sequences of the invention are used as probes to identify and isolate related nucleic acids. In some aspects, the so-identified related nucleic acids may be cDNAs or genomic DNAs from organisms other than the one from which the nucleic acid of the invention was first isolated. In such procedures, a nucleic acid sample is contacted with the probe under conditions which permit the probe to specifically hybridize to related sequences. Hybridization of the probe to nucleic acids from the related organism is then detected using any of the methods described above.

In nucleic acid hybridization reactions, the conditions used to achieve a particular level of stringency can vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter. Hybridization can be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2\times10^7$ cpm (specific activity $4\text{-}9\times10^8$ cpm/ug) of $^{32}P$ end-labeled oligonucleotide probe can then added to the solution. After 12-16 hours of incubation, the membrane is washed for 30 minutes at room temperature (RT) in 1×SET (150 mM NaCl, 20 mM Tris hydrochloride, pH 7.8, 1 mM $Na_2EDTA$) containing 0.5% SDS, followed by a 30 minute wash in fresh 1×SET at Tm-10° C. for the oligonucleotide probe. The membrane is then exposed to auto-radiographic film for detection of hybridization signals.

By varying the stringency of the hybridization conditions used to identify nucleic acids, such as cDNAs or genomic DNAs, which hybridize to the detectable probe, nucleic acids having different levels of homology to the probe can be identified and isolated. Stringency may be varied by conducting the hybridization at varying temperatures below the melting temperatures of the probes. The melting temperature, Tm, is the temperature (under defined ionic strength and pH) at which 50% of the target sequence hybridizes to a perfectly complementary probe. Very stringent conditions are selected to be equal to or about 5° C. lower than the Tm for a particular probe. The melting temperature of the probe may be calculated using the following exemplary formulas. For probes between 14 and 70 nucleotides in length the melting temperature (Tm) is calculated using the formula: Tm=81.5+16.6(log [Na+])+0.41(fraction G+C)−(600/N) where N is the length of the probe. If the hybridization is carried out in a solution containing formamide, the melting temperature may be calculated using the equation: Tm=81.5+16.6(log [Na+])+0.41(fraction G+C)−(0.63% formamide)−(600/N) where N is the length of the probe. Prehybridization may be carried out in 6×SSC, 5×Denhardt's reagent, 0.5% SDS, 100 µg denatured fragmented salmon sperm DNA or 6×SSC, 5×Denhardt's reagent, 0.5% SDS, 100 µg denatured fragmented salmon sperm DNA, 50% formamide. Formulas for SSC and Denhardt's and other solutions are listed, e.g., in Sambrook.

Hybridization is conducted by adding the detectable probe to the prehybridization solutions listed above. Where the probe comprises double stranded DNA, it is denatured before addition to the hybridization solution. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. In one aspect, hybridizations in 6×SSC are conducted at approximately 68° C. In one aspect, hybridizations in 50% formamide containing solutions are conducted at approximately 42° C. All of the foregoing hybridizations would be considered to be under conditions of high stringency.

Following hybridization, the filter is washed to remove any non-specifically bound detectable probe. The stringency used to wash the filters can also be varied depending on the nature of the nucleic acids being hybridized, the length of the nucleic acids being hybridized, the degree of complementarity, the nucleotide sequence composition (e.g., GC v. AT content), and the nucleic acid type (e.g., RNA v. DNA). Examples of progressively higher stringency condition washes are as follows: 2×SSC, 0.1% SDS at room temperature for 15 minutes (low stringency); 0.1×SSC, 0.5% SDS at room temperature for 30 minutes to 1 hour (moderate stringency); 0.1×SSC, 0.5% SDS for 15 to 30 minutes at between the hybridization temperature and 68° C. (high stringency); and 0.15M NaCl for 15 minutes at 72° C. (very high stringency). A final low stringency wash can be conducted in 0.1×SSC at room temperature. The examples above are merely illustrative of one set of conditions that can be used to wash filters. One of skill in the art would know that there are numerous recipes for different stringency washes.

Nucleic acids which have hybridized to the probe can be identified by autoradiography or other conventional techniques. The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate" conditions above 50° C. and "low" conditions below 50° C. An example of "moderate" hybridization conditions is when the above hybridization is conducted at 55° C. An example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate" conditions above 25% formamide and "low" conditions below 25% formamide. A specific example of "moderate" hybridization conditions is when the above hybridization is conducted at 30% formamide. A specific example of "low stringency" hybridization conditions is when the above hybridization is conducted at 10% formamide.

These probes and methods of the invention can be used to isolate nucleic acids having a sequence with at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% homology to a nucleic acid sequence of the invention comprising at least about 10, 15, 20, 25, 30, 35, 40, 50, 75, 100, 150, 200, 250, 300, 350, 400, 500, 550, 600, 650, 700, 750, 800, 850, 900, 950, 1000, or more consecutive bases thereof, and the sequences complementary thereto. Homology may be measured using an alignment algorithm, as discussed herein. For example, the homologous polynucleotides may have a coding sequence which is a naturally occurring allelic variant of one of the coding sequences described herein. Such allelic variants may have a substitution, deletion or addition of one or more nucleotides when compared to a nucleic acid of the invention.

Additionally, the probes and methods of the invention can be used to isolate nucleic acids which encode polypeptides having at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% sequence identity (homology) to a polypeptide of the invention comprising at least 5, 10, 15, 20, 25, 30, 35, 40, 50, 75, 100, or 150 consecutive amino acids, as determined using a sequence alignment algorithm (e.g., such as the FASTA version 3.0t78 algorithm with the default parameters, or a BLAST 2.2.2 program with exemplary settings as set forth herein).

Inhibiting Expression of Amylase

The invention provides nucleic acids complementary to (e.g., antisense sequences to) the nucleic acid sequences of the invention. Antisense sequences are capable of inhibiting the transport, splicing or transcription of amylase-encoding genes. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind amylase gene or message, in either case preventing or inhibiting the production or function of amylase. The association can be through sequence specific hybridization. Another useful class of inhibitors includes oligonucleotides which cause inactivation or cleavage of amylase message. The oligonucleotide can have enzyme activity which causes such cleavage, such as ribozymes. The oligonucleotide can be chemically modified or conjugated to an enzyme or composition capable of cleaving the complementary nucleic acid. A pool of many different such oligonucleotides can be screened for those with the desired activity.

Antisense Oligonucleotides

The invention provides antisense oligonucleotides capable of binding amylase message which can inhibit proteolytic activity by targeting mRNA. Strategies for designing antisense oligonucleotides are well described in the scientific and patent literature, and the skilled artisan can design such amylase oligonucleotides using the novel reagents of the invention. For example, gene walking/RNA mapping protocols to screen for effective antisense oligonucleotides are well known in the art, see, e.g., Ho (2000) Methods Enzymol. 314:168-183, describing an RNA mapping assay, which is based on standard molecular techniques to provide an easy and reliable method for potent antisense sequence selection. See also Smith (2000) Eur. J. Pharm. Sci. 11:191-198.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2- aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene (methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense amylase sequences of the invention (see, e.g., Gold (1995) J. of Biol. Chem. 270:13581-13584).

Inhibitory Ribozymes

The invention provides ribozymes capable of binding amylase message. These ribozymes can inhibit amylase activity by, e.g., targeting mRNA. Strategies for designing ribozymes and selecting the amylase-specific antisense sequence for targeting are well described in the scientific and patent literature, and the skilled artisan can design such ribozymes using the novel reagents of the invention. Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The ribozyme of the invention, e.g., an enzymatic ribozyme RNA molecule, can be formed in a hammerhead motif, a hairpin motif, as a hepatitis delta virus motif, a group I intron motif and/or an RNaseP-like RNA in association with an RNA guide sequence. Examples of hammerhead motifs are described by, e.g., Rossi (1992) Aids Research and Human Retroviruses 8:183; hairpin motifs by Hampel (1989) Biochemistry 28:4929, and Hampel (1990) Nuc. Acids Res. 18:299; the hepatitis delta virus motif by Perrotta (1992) Biochemistry 31:16; the RNaseP motif by Guerrier-Takada (1983) Cell 35:849; and the group I intron by Cech U.S. Pat. No. 4,987,071. The recitation of these specific motifs is not intended to be limiting. Those skilled in the art will recognize that a ribozyme of the invention, e.g., an enzymatic RNA molecule of this invention, can have a specific substrate binding site complementary to one or more of the target gene RNA regions. A ribozyme of the invention can have a nucleotide sequence within or surrounding that substrate binding site which imparts an RNA cleaving activity to the molecule.

RNA Interference (RNAi)

In one aspect, the invention provides an RNA inhibitory molecule, a so-called "RNAi" molecule, comprising an amylase sequence of the invention. The RNAi molecule comprises a double-stranded RNA (dsRNA) molecule. The RNAi can inhibit expression of an amylase gene. In one aspect, the RNAi is about 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi is the breaking of a double-stranded RNA (dsRNA) matching a specific gene sequence into short pieces called short interfering RNA, which trigger the degradation of mRNA that matches its sequence. In one aspect, the RNAi's of the invention are used in gene-silencing therapeutics, see, e.g., Shuey (2002) Drug Discov. Today 7:1040-1046. In one aspect, the invention provides methods to selectively degrade RNA using the RNAi's of the invention. The process may be practiced in vitro, ex vivo or in vivo. In one aspect, the RNAi molecules of the invention can be used to generate a loss-of-function mutation in a cell, an organ or an animal. Methods for making and using RNAi molecules for selectively degrade RNA are well known in the art, see, e.g., U.S. Pat. Nos. 6,506,559; 6,511,824; 6,515,109; 6,489,127.

Modification of Nucleic Acids

The invention provides methods of generating variants of the nucleic acids of the invention, e.g., those encoding an amylase. These methods can be repeated or used in various combinations to generate amylases having an altered or different activity or an altered or different stability from that of an amylase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

A nucleic acid of the invention can be altered by any means. For example, random or stochastic methods, or, non-stochastic, or "directed evolution," methods, see, e.g., U.S. Pat. No. 6,361,974. Methods for random mutation of genes are well known in the art, see, e.g., U.S. Pat. No. 5,830,696. For example, mutagens can be used to randomly mutate a gene. Mutagens include, e.g., ultraviolet light or gamma irradiation, or a chemical mutagen, e.g., mitomycin, nitrous acid, photoactivated psoralens, alone or in combination, to induce DNA breaks amenable to repair by recombination. Other chemical mutagens include, for example, sodium bisulfite, nitrous acid, hydroxylamine, hydrazine or formic acid. Other mutagens are analogues of nucleotide precursors, e.g., nitrosoguanidine, 5-bromouracil, 2-aminopurine, or acridine. These agents can be added to a PCR reaction in place of the nucleotide precursor thereby mutating the sequence. Intercalating agents such as proflavine, acriflavine, quinacrine and the like can also be used.

Any technique in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

The following publications describe a variety of recursive recombination procedures and/or methods which can be incorporated into the methods of the invention: Stemmer (1999) "Molecular breeding of viruses for targeting and other clinical properties" Tumor Targeting 4:1-4; Ness (1999) Nature Biotechnology 17:893-896; Chang (1999) "Evolution of a cytokine using DNA family shuffling" Nature Biotechnology 17:793-797; Minshull (1999) "Protein evolution by molecular breeding" Current Opinion in Chemical Biology 3:284-290; Christians (1999) "Directed evolution of thymidine kinase for AZT phosphorylation using DNA family shuffling" Nature Biotechnology 17:259-264; Crameri (1998) "DNA shuffling of a family of genes from diverse species accelerates directed evolution" Nature 391:288-291; Crameri (1997) "Molecular evolution of an arsenate detoxification pathway by DNA shuffling," Nature Biotechnology 15:436-438; Zhang (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Gates et al. (1996) "Affinity selective isolation of ligands from peptide libraries through display on a lac repressor 'headpiece dimer'" Journal of Molecular Biology 255:373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al. (1995) "Single-step assembly of a gene and entire plasmid form large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787 (1985); Nakamaye (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154: 350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional protocols that can be used to practice the invention include point mismatch repair (Kramer (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh (1986) "Use of oligonucleotides to generate large deletions" Nucl. Acids Res. 14: 5115), restriction-selection and restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316), double-strand break repair (Mandecki (1986); Arnold (1993) "Protein engineering for unusual environments" Current Opinion in Biotechnology 4:450-455. "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Protocols that can be used to practice the invention are described, e.g., in U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/27230 by Stemmer et al., "Methods for Optimization of Gene Therapy by Recursive Sequence Shuffling and Selection," WO 00/00632, "Methods for Generating Highly Diverse Libraries," WO 00/09679, "Methods for Obtaining in Vitro Recombined Polynucleotide Sequence Banks and Resulting Sequences," WO 98/42832 by Arnold et al., "Recombination of Polynucleotide Sequences Using Random or Defined Primers," WO 99/29902 by Arnold et al., "Method for Creating Polynucleotide and Polypeptide Sequences," WO 98/41653 by Vind, "An in Vitro Method for Construction of a DNA Library," WO 98/41622 by Borchert et al., "Method for Constructing a Library Using DNA Shuffling," and WO 98/42727 by Pati and Zarling, "Sequence Alterations using Homologous Recombination."

Protocols that can be used to practice the invention (providing details regarding various diversity generating methods) are described, e.g., in U.S. patent application Ser. No. 09/407,800, "SHUFFLING OF CODON ALTERED GENES" by Patten et al. filed Sep. 28, 1999; "EVOLUTION OF WHOLE CELLS AND ORGANISMS BY RECURSIVE SEQUENCE RECOMBINATION" by del Cardayre et al., U.S. Pat. No. 6,379,964; "OLIGONUCLEOTIDE MEDIATED NUCLEIC ACID RECOMBINATION" by Crameri et al., U.S. Pat. Nos. 6,319,714; 6,368,861; 6,376,246; 6,423,542; 6,426,224 and PCT/US00/01203; "USE OF CODON-VARIED OLIGONUCLEOTIDE SYNTHESIS FOR SYNTHETIC SHUFFLING" by Welch et al., U.S. Pat. No. 6,436,675; "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (PCT/US00/01202) and, e.g. "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer, filed Jan. 18, 2000 (PCT/US00/01138); and "SINGLE-STRANDED NUCLEIC ACID TEMPLATE-MEDIATED RECOMBINATION AND NUCLEIC ACID FRAGMENT ISOLATION" by Affholter, filed Sep. 6, 2000 (U.S. Ser. No. 09/656,549); and U.S. Pat. Nos. 6,177,263; 6,153,410.

Non-stochastic, or "directed evolution," methods include, e.g., saturation mutagenesis (GSSM), synthetic ligation reassembly (SLR), or a combination thereof are used to modify the nucleic acids of the invention to generate amylases with new or altered properties (e.g., activity under highly acidic or alkaline conditions, high temperatures, and the like). Polypeptides encoded by the modified nucleic acids can be screened for an activity before testing for proteolytic or other activity. Any testing modality or protocol can be used, e.g., using a capillary array platform. See, e.g., U.S. Pat. Nos. 6,361,974; 6,280,926; 5,939,250.

Saturation Mutagenesis, or, GSSM

In one aspect, codon primers containing a degenerate N,N,G/T sequence are used to introduce point mutations into a polynucleotide, e.g., an amylase or an antibody of the invention, so as to generate a set of progeny polypeptides in which a full range of single amino acid substitutions is represented at each amino acid position, e.g., an amino acid residue in an enzyme active site or ligand binding site targeted to be modified. These oligonucleotides can comprise a contiguous first homologous sequence, a degenerate N,N,G/T sequence, and, optionally, a second homologous sequence. The downstream progeny translational products from the use of such oligonucleotides include all possible amino acid changes at each amino acid site along the polypeptide, because the degeneracy of the N,N,G/T sequence includes codons for all 20 amino acids. In one aspect, one such degenerate oligonucleotide (comprised of, e.g., one degenerate N,N,G/T cassette) is used for subjecting each original codon in a parental polynucleotide template to a full range of codon substitutions. In another aspect, at least two degenerate cassettes are used—either in the same oligonucleotide or not, for subjecting at least two original codons in a parental polynucleotide template to a full range of codon substitutions. For example, more than one N,N,G/T sequence can be contained in one oligonucleotide to introduce amino acid mutations at more than one site. This plurality of N,N,G/T sequences can be directly contiguous, or separated by one or more additional nucleotide sequence(s). In another aspect, oligonucleotides serviceable for introducing additions and deletions can be used either alone or in combination with the codons containing an N,N,G/T sequence, to introduce any combination or permutation of amino acid additions, deletions, and/or substitutions.

In one aspect, simultaneous mutagenesis of two or more contiguous amino acid positions is done using an oligonucleotide that contains contiguous N,N,G/T triplets, i.e. a degenerate (N,N,G/T)n sequence. In another aspect, degenerate cassettes having less degeneracy than the N,N,G/T sequence are used. For example, it may be desirable in some instances to use (e.g. in an oligonucleotide) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g. in an oligo) a degenerate N,N,N triplet sequence.

In one aspect, use of degenerate triplets (e.g., N,N,G/T triplets) allows for systematic and easy generation of a full range of possible natural amino acids (for a total of 20 amino acids) into each and every amino acid position in a polypeptide (in alternative aspects, the methods also include generation of less than all possible substitutions per amino acid residue, or codon, position). For example, for a 100 amino acid polypeptide, 2000 distinct species (i.e. 20 possible amino acids per position×100 amino acid positions) can be generated. Through the use of an oligonucleotide or set of oligonucleotides containing a degenerate N,N,G/T triplet, 32 individual sequences can code for all 20 possible natural amino acids. Thus, in a reaction vessel in which a parental polynucleotide sequence is subjected to saturation mutagenesis using at least one such oligonucleotide, there are generated 32 distinct progeny polynucleotides encoding 20 distinct polypeptides. In contrast, the use of a non-degenerate oligonucleotide in site-directed mutagenesis leads to only one progeny polypeptide product per reaction vessel. Nondegenerate oligonucleotides can optionally be used in combination with degenerate primers disclosed; for example, nondegenerate oligonucleotides can be used to generate specific point mutations in a working polynucleotide. This provides one means to generate specific silent point mutations, point mutations leading to corresponding amino acid changes, and point mutations that cause the generation of stop codons and the corresponding expression of polypeptide fragments.

In one aspect, each saturation mutagenesis reaction vessel contains polynucleotides encoding at least 20 progeny polypeptide (e.g., amylases) molecules such that all 20 natural amino acids are represented at the one specific amino acid position corresponding to the codon position mutagenized in the parental polynucleotide (other aspects use less than all 20 natural combinations). The 32-fold degenerate progeny polypeptides generated from each saturation mutagenesis reaction vessel can be subjected to clonal amplification (e.g. cloned into a suitable host, e.g., E. coli host, using, e.g., an expression vector) and subjected to expression screening. When an individual progeny polypeptide is identified by screening to display a favorable change in property (when compared to the parental polypeptide, such as increased proteolytic activity under alkaline or acidic conditions), it can be sequenced to identify the correspondingly favorable amino acid substitution contained therein.

In one aspect, upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined–6 single point mutations (i.e. 2 at each of three positions) and no change at any position.

In another aspect, site-saturation mutagenesis can be used together with another stochastic or non-stochastic means to vary sequence, e.g., synthetic ligation reassembly (see below), shuffling, chimerization, recombination and other mutagenizing processes and mutagenizing agents. This invention provides for the use of any mutagenizing process (es), including saturation mutagenesis, in an iterative manner.

Synthetic Ligation Reassembly (SLR)

The invention provides a non-stochastic gene modification system termed "synthetic ligation reassembly," or simply "SLR," a "directed evolution process," to generate polypeptides, e.g., amylases or antibodies of the invention, with new or altered properties. SLR is a method of ligating oligonucleotide fragments together non-stochastically. This method differs from stochastic oligonucleotide shuffling in that the nucleic acid building blocks are not shuffled, concatenated or chimerized randomly, but rather are assembled non-stochastically. See, e.g., U.S. patent application Ser. No. 09/332,835 entitled "Synthetic Ligation Reassembly in Directed Evolution" and filed on Jun. 14, 1999 ("U.S. Ser. No. 09/332,835"). In one aspect, SLR comprises the following steps: (a) providing a template polynucleotide, wherein the template polynucleotide comprises sequence encoding a homologous gene; (b) providing a plurality of building block polynucleotides, wherein the building block polynucleotides are designed to cross-over reassemble with the template polynucleotide at a predetermined sequence, and a building block polynucleotide comprises a sequence that is a variant of the homologous gene and a sequence homologous to the template polynucleotide flanking the variant sequence; (c) combining a building block polynucleotide with a template polynucleotide such that the building block polynucleotide cross-over reassembles with the template polynucleotide to generate polynucleotides comprising homologous gene sequence variations.

SLR does not depend on the presence of high levels of homology between polynucleotides to be rearranged. Thus, this method can be used to non-stochastically generate libraries (or sets) of progeny molecules comprised of over 10100 different chimeras. SLR can be used to generate libraries comprised of over 101000 different progeny chimeras. Thus, aspects of the present invention include non-stochastic methods of producing a set of finalized chimeric nucleic acid molecule shaving an overall assembly order that is chosen by design. This method includes the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, the overall assembly order in which the nucleic acid building blocks can be coupled is specified by the design of the ligatable ends. If more than one assembly step is to be used, then the overall assembly order in which the nucleic acid building blocks can be coupled is also specified by the sequential order of the assembly step(s). In one aspect, the annealed building pieces are treated with an enzyme, such as a ligase (e.g. T4 DNA ligase), to achieve covalent bonding of the building pieces.

In one aspect, the design of the oligonucleotide building blocks is obtained by analyzing a set of progenitor nucleic acid sequence templates that serve as a basis for producing a progeny set of finalized chimeric polynucleotides. These parental oligonucleotide templates thus serve as a source of sequence information that aids in the design of the nucleic acid building blocks that are to be mutagenized, e.g., chimerized or shuffled. In one aspect of this method, the sequences of a plurality of parental nucleic acid templates are aligned in order to select one or more demarcation points. The demarcation points can be located at an area of homology, and are comprised of one or more nucleotides. These demarcation points are preferably shared by at least two of the progenitor templates. The demarcation points can thereby be used to delineate the boundaries of oligonucleotide building blocks to be generated in order to rearrange the parental polynucleotides. The demarcation points identified and selected in the progenitor molecules serve as potential chimerization points in the assembly of the final chimeric progeny molecules. A demarcation point can be an area of homology (comprised of at least one homologous nucleotide base) shared by at least two parental polynucleotide sequences. Alternatively, a demarcation point can be an area of homology that is shared by at least half of the parental polynucleotide sequences, or, it can be an area of homology that is shared by at least two thirds of the parental polynucleotide sequences. Even more preferably a serviceable demarcation points is an area of homology that is shared by at least three fourths of the parental polynucleotide sequences, or, it can be shared by at almost all of the parental polynucleotide sequences. In one aspect, a demarcation point is an area of homology that is shared by all of the parental polynucleotide sequences.

In one aspect, a ligation reassembly process is performed exhaustively in order to generate an exhaustive library of progeny chimeric polynucleotides. In other words, all possible ordered combinations of the nucleic acid building blocks are represented in the set of finalized chimeric nucleic acid molecules. At the same time, in another aspect, the assembly order (i.e. the order of assembly of each building block in the 5' to 3 sequence of each finalized chimeric nucleic acid) in each combination is by design (or non-stochastic) as described above. Because of the non-stochastic nature of this invention, the possibility of unwanted side products is greatly reduced.

In another aspect, the ligation reassembly method is performed systematically. For example, the method is performed in order to generate a systematically compartmentalized library of progeny molecules, with compartments that can be screened systematically, e.g. one by one. In other words this invention provides that, through the selective and judicious use of specific nucleic acid building blocks, coupled with the selective and judicious use of sequentially stepped assembly reactions, a design can be achieved where specific sets of progeny products are made in each of several reaction vessels. This allows a systematic examination and screening procedure to be performed. Thus, these methods allow a potentially very large number of progeny molecules to be examined systematically in smaller groups. Because of its ability to perform chimerizations in a manner that is highly flexible yet exhaustive and systematic as well, particularly when there is a low level of homology among the progenitor molecules, these methods provide for the generation of a library (or set) comprised of a large number of progeny molecules. Because of the non-stochastic nature of the instant ligation reassembly invention, the progeny molecules generated preferably comprise a library of finalized chimeric nucleic acid molecules having an overall assembly order that is chosen by design. The saturation mutagenesis and optimized directed evolution methods also can be used to generate different progeny molecular species. It is appreciated that the invention provides freedom of choice and control regarding the selection of demarcation points, the size and number of the nucleic acid building blocks, and the size and design of the couplings. It is appreciated, furthermore, that the requirement for intermolecular homology is highly relaxed for the operability of this invention. In fact, demarcation points can even be chosen in areas of little or no intermolecular homology. For example, because of codon wobble, i.e. the degeneracy of codons, nucleotide substitutions can be introduced into nucleic acid building blocks without altering the amino acid originally encoded in the corresponding progenitor template. Alternatively, a codon can be altered such that the coding for an originally amino acid is altered. This invention provides that such substitutions can be introduced into the nucleic acid building block in order to increase the incidence of intermolecular homologous demarcation points and thus to allow an increased number of couplings to be achieved among the building blocks, which in turn allows a greater number of progeny chimeric molecules to be generated.

In another aspect, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g. by mutagenesis) or in an in vivo process (e.g. by utilizing the gene splicing ability of a host organism). It is appreciated that in many instances the introduction of these nucleotides may also be desirable for many other reasons in addition to the potential benefit of creating a serviceable demarcation point.

In one aspect, a nucleic acid building block is used to introduce an intron. Thus, functional introns are introduced into a man-made gene manufactured according to the methods described herein. The artificially introduced intron(s)

can be functional in a host cells for gene splicing much in the way that naturally-occurring introns serve functionally in gene splicing.

Optimized Directed Evolution System

The invention provides a non-stochastic gene modification system termed "optimized directed evolution system" to generate polypeptides, e.g., amylases or antibodies of the invention, with new or altered properties. Optimized directed evolution is directed to the use of repeated cycles of reductive reassortment, recombination and selection that allow for the directed molecular evolution of nucleic acids through recombination. Optimized directed evolution allows generation of a large population of evolved chimeric sequences, wherein the generated population is significantly enriched for sequences that have a predetermined number of crossover events.

A crossover event is a point in a chimeric sequence where a shift in sequence occurs from one parental variant to another parental variant. Such a point is normally at the juncture of where oligonucleotides from two parents are ligated together to form a single sequence. This method allows calculation of the correct concentrations of oligonucleotide sequences so that the final chimeric population of sequences is enriched for the chosen number of crossover events. This provides more control over choosing chimeric variants having a predetermined number of crossover events.

In addition, this method provides a convenient means for exploring a tremendous amount of the possible protein variant space in comparison to other systems. Previously, if one generated, for example, $10^{13}$ chimeric molecules during a reaction, it would be extremely difficult to test such a high number of chimeric variants for a particular activity. Moreover, a significant portion of the progeny population would have a very high number of crossover events which resulted in proteins that were less likely to have increased levels of a particular activity. By using these methods, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

One method for creating a chimeric progeny polynucleotide sequence is to create oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. Additional information can also be found, e.g., in U.S. Ser. No. 09/332,835; U.S. Pat. No. 6,361,974.

The number of oligonucleotides generated for each parental variant bears a relationship to the total number of resulting crossovers in the chimeric molecule that is ultimately created. For example, three parental nucleotide sequence variants might be provided to undergo a ligation reaction in order to find a chimeric variant having, for example, greater activity at high temperature. As one example, a set of 50 oligonucleotide sequences can be generated corresponding to each portions of each parental variant. Accordingly, during the ligation reassembly process there could be up to 50 crossover events within each of the chimeric sequences. The probability that each of the generated chimeric polynucleotides will contain oligonucleotides from each parental variant in alternating order is very low. If each oligonucleotide fragment is present in the ligation reaction in the same molar quantity it is likely that in some positions oligonucleotides from the same parental polynucleotide will ligate next to one another and thus not result in a crossover event. If the concentration of each oligonucleotide from each parent is kept constant during any ligation step in this example, there is a ⅓ chance (assuming 3 parents) that an oligonucleotide from the same parental variant will ligate within the chimeric sequence and produce no crossover.

Accordingly, a probability density function (PDF) can be determined to predict the population of crossover events that are likely to occur during each step in a ligation reaction given a set number of parental variants, a number of oligonucleotides corresponding to each variant, and the concentrations of each variant during each step in the ligation reaction. The statistics and mathematics behind determining the PDF is described below. By utilizing these methods, one can calculate such a probability density function, and thus enrich the chimeric progeny population for a predetermined number of crossover events resulting from a particular ligation reaction. Moreover, a target number of crossover events can be predetermined, and the system then programmed to calculate the starting quantities of each parental oligonucleotide during each step in the ligation reaction to result in a probability density function that centers on the predetermined number of crossover events. These methods are directed to the use of repeated cycles of reductive reassortment, recombination and selection that allow for the directed molecular evolution of a nucleic acid encoding a polypeptide through recombination. This system allows generation of a large population of evolved chimeric sequences, wherein the generated population is significantly enriched for sequences that have a predetermined number of crossover events. A crossover event is a point in a chimeric sequence where a shift in sequence occurs from one parental variant to another parental variant. Such a point is normally at the juncture of where oligonucleotides from two parents are ligated together to form a single sequence. The method allows calculation of the correct concentrations of oligonucleotide sequences so that the final chimeric population of sequences is enriched for the chosen number of crossover events. This provides more control over choosing chimeric variants having a predetermined number of crossover events.

In addition, these methods provide a convenient means for exploring a tremendous amount of the possible protein variant space in comparison to other systems. By using the methods described herein, the population of chimerics molecules can be enriched for those variants that have a particular number of crossover events. Thus, although one can still generate $10^{13}$ chimeric molecules during a reaction, each of the molecules chosen for further analysis most likely has, for example, only three crossover events. Because the resulting progeny population can be skewed to have a predetermined number of crossover events, the boundaries on the functional variety between the chimeric molecules is reduced. This provides a more manageable number of variables when calculating which oligonucleotide from the original parental polynucleotides might be responsible for affecting a particular trait.

In one aspect, the method creates a chimeric progeny polynucleotide sequence by creating oligonucleotides corresponding to fragments or portions of each parental sequence. Each oligonucleotide preferably includes a unique region of overlap so that mixing the oligonucleotides together results in a new variant that has each oligonucleotide fragment assembled in the correct order. See also U.S. Ser. No. 09/332,835.

Determining Crossover Events

Aspects of the invention include a system and software that receive a desired crossover probability density function (PDF), the number of parent genes to be reassembled, and the number of fragments in the reassembly as inputs. The output of this program is a "fragment PDF" that can be used to determine a recipe for producing reassembled genes, and the estimated crossover PDF of those genes. The processing described herein is preferably performed in MATLAB™ (The Mathworks, Natick, Mass.) a programming language and development environment for technical computing.

Iterative Processes

In practicing the invention, these processes can be iteratively repeated. For example, a nucleic acid (or, the nucleic acid) responsible for an altered or new amylase phenotype is identified, re-isolated, again modified, re-tested for activity. This process can be iteratively repeated until a desired phenotype is engineered. For example, an entire biochemical anabolic or catabolic pathway can be engineered into a cell, including, e.g., starch hydrolysis activity.

Similarly, if it is determined that a particular oligonucleotide has no affect at all on the desired trait (e.g., a new amylase phenotype), it can be removed as a variable by synthesizing larger parental oligonucleotides that include the sequence to be removed. Since incorporating the sequence within a larger sequence prevents any crossover events, there will no longer be any variation of this sequence in the progeny polynucleotides. This iterative practice of determining which oligonucleotides are most related to the desired trait, and which are unrelated, allows more efficient exploration all of the possible protein variants that might be provide a particular trait or activity.

In Vivo Shuffling

In vivo shuffling of molecules is use in methods of the invention that provide variants of polypeptides of the invention, e.g., antibodies, amylases, and the like. In vivo shuffling can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In one aspect, the invention provides a method for producing a hybrid polynucleotide from at least a first polynucleotide (e.g., an amylase of the invention) and a second polynucleotide (e.g., an enzyme, such as an amylase of the invention or any other amylase, or, a tag or an epitope). The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

Producing Sequence Variants

The invention also provides additional methods for making sequence variants of the nucleic acid (e.g., amylase) sequences of the invention. The invention also provides additional methods for isolating amylases using the nucleic acids and polypeptides of the invention. In one aspect, the invention provides for variants of an amylase coding sequence (e.g., a gene, cDNA or message) of the invention, which can be altered by any means, including, e.g., random or stochastic methods, or, non-stochastic, or "directed evolution," methods, as described above.

The isolated variants may be naturally occurring. Variant can also be created in vitro. Variants may be created using genetic engineering techniques such as site directed mutagenesis, random chemical mutagenesis, Exonuclease III deletion procedures, and standard cloning techniques. Alternatively, such variants, fragments, analogs, or derivatives may be created using chemical synthesis or modification procedures. Other methods of making variants are also familiar to those skilled in the art. These include procedures in which nucleic acid sequences obtained from natural isolates are modified to generate nucleic acids which encode polypeptides having characteristics which enhance their value in industrial or laboratory applications. In such procedures, a large number of variant sequences having one or more nucleotide differences with respect to the sequence obtained from the natural isolate are generated and characterized. These nucleotide differences can result in amino acid changes with respect to the polypeptides encoded by the nucleic acids from the natural isolates.

For example, variants may be created using error prone PCR. In error prone PCR, PCR is performed under conditions where the copying fidelity of the DNA polymerase is low, such that a high rate of point mutations is obtained along the entire length of the PCR product. Error prone PCR is described, e.g., in Leung, D. W., et al., Technique, 1:11-15, 1989) and Caldwell, R. C. & Joyce G. F., PCR Methods Applic., 2:28-33, 1992. Briefly, in such procedures, nucleic acids to be mutagenized are mixed with PCR primers, reaction buffer, $MgCl_2$, $MnCl_2$, Taq polymerase and an appropriate concentration of dNTPs for achieving a high rate of point mutation along the entire length of the PCR product. For example, the reaction may be performed using 20 fmoles of nucleic acid to be mutagenized, 30 pmole of each PCR primer, a reaction buffer comprising 50 mM KCl, 10 mM Tris HCl (pH 8.3) and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR may be performed for 30 cycles of 94° C. for 1 min, 45° C. for 1 min, and 72° C. for 1 min. However, it will be appreciated that these parameters may be varied as appropriate. The mutagenized nucleic acids are cloned into an appropriate vector and the activities of the polypeptides encoded by the mutagenized nucleic acids is evaluated.

Variants may also be created using oligonucleotide directed mutagenesis to generate site-specific mutations in any cloned DNA of interest. Oligonucleotide mutagenesis is described, e.g., in Reidhaar-Olson (1988) Science 241:53-57. Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, e.g., U.S. Pat. No. 5,965,408.

Still another method of generating variants is sexual PCR mutagenesis. In sexual PCR mutagenesis, forced homologous recombination occurs between DNA molecules of different but highly related DNA sequence in vitro, as a result of random fragmentation of the DNA molecule based on sequence homology, followed by fixation of the crossover by primer extension in a PCR reaction. Sexual PCR mutagenesis is described, e.g., in Stemmer (1994) Proc. Natl. Acad. Sci. USA 91:10747-10751. Briefly, in such procedures a plurality of nucleic acids to be recombined are digested with DNase to generate fragments having an average size of 50-200 nucleotides. Fragments of the desired average size are purified and resuspended in a PCR mixture. PCR is conducted under conditions which facilitate recombination between the nucleic acid fragments. For example, PCR may be performed by resuspending the purified fragments at a concentration of 10-30 ng/:1 in a solution of 0.2 mM of each dNTP, 2.2 mM $MgCl_2$, 50 mM KCL, 10 mM Tris HCl, pH 9.0, and 0.1% Triton X-100. 2.5 units of Taq polymerase per 100:1 of reaction mixture is added and PCR is performed using the following regime: 94° C. for 60 seconds, 94° C. for 30 seconds, 50-55° C. for 30 seconds, 72° C. for 30 seconds (30-45 times) and 72° C. for 5 minutes. However, it will be appreciated that these parameters may be varied as appropriate. In some aspects, oligonucleotides may be included in the PCR reactions. In other aspects, the Klenow fragment of DNA polymerase I may be used in a first set of PCR reactions and Taq polymerase may be used in a subsequent set of PCR reactions. Recombinant sequences are isolated and the activities of the polypeptides they encode are assessed.

Variants may also be created by in vivo mutagenesis. In some aspects, random mutations in a sequence of interest are generated by propagating the sequence of interest in a bacterial strain, such as an *E. coli* strain, which carries mutations in one or more of the DNA repair pathways. Such "mutator" strains have a higher random mutation rate than that of a wild-type parent. Propagating the DNA in one of these strains will eventually generate random mutations within the DNA. Mutator strains suitable for use for in vivo mutagenesis are described, e.g., in PCT Publication No. WO 91/16427.

Variants may also be generated using cassette mutagenesis. In cassette mutagenesis a small region of a double stranded DNA molecule is replaced with a synthetic oligonucleotide "cassette" that differs from the native sequence. The oligonucleotide often contains completely and/or partially randomized native sequence.

Recursive ensemble mutagenesis may also be used to generate variants. Recursive ensemble mutagenesis is an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described, e.g., in Arkin (1992) Proc. Natl. Acad. Sci. USA 89:7811-7815.

In some aspects, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described, e.g., in Delegrave (1993) Biotechnology Res. 11:1548-1552. Random and site-directed mutagenesis are described, e.g., in Arnold (1993) Current Opinion in Biotechnology 4:450-455.

In some aspects, the variants are created using shuffling procedures wherein portions of a plurality of nucleic acids which encode distinct polypeptides are fused together to create chimeric nucleic acid sequences which encode chimeric polypeptides as described in, e.g., U.S. Pat. Nos. 5,965,408; 5,939,250 (see also discussion, above).

The invention also provides variants of polypeptides of the invention (e.g., amylases) comprising sequences in which one or more of the amino acid residues (e.g., of an exemplary polypeptide of the invention) are substituted with a conserved or non-conserved amino acid residue (e.g., a conserved amino acid residue) and such substituted amino acid residue may or may not be one encoded by the genetic code. Conservative substitutions are those that substitute a given amino acid in a polypeptide by another amino acid of like characteristics. Thus, polypeptides of the invention include those with conservative substitutions of sequences of the invention, e.g., the exemplary polypeptides of the invention, including but not limited to the following replacements: replacements of an aliphatic amino acid such as Alanine, Valine, Leucine and Isoleucine with another aliphatic amino acid; replacement of a Serine with a Threonine or vice versa; replacement of an acidic residue such as Aspartic acid and Glutamic acid with another acidic residue; replacement of a residue bearing an amide group, such as Asparagine and Glutamine, with another residue bearing an amide group; exchange of a basic residue such as Lysine and Arginine with another basic residue; and replacement of an aromatic residue such as Phenylalanine, Tyrosine with another aromatic residue. Other variants are those in which one or more of the amino acid residues of the polypeptides of the invention includes a substituent group.

Other variants within the scope of the invention are those in which the polypeptide is associated with another compound, such as a compound to increase the half-life of the polypeptide, for example, polyethylene glycol.

Additional variants within the scope of the invention are those in which additional amino acids are fused to the polypeptide, such as a leader sequence, a secretory sequence, a proprotein sequence or a sequence which facilitates purification, enrichment, or stabilization of the polypeptide.

In some aspects, the variants, fragments, derivatives and analogs of the polypeptides of the invention retain the same biological function or activity as the exemplary polypeptides, e.g., amylase activity, as described herein. In other aspects, the variant, fragment, derivative, or analog includes a proprotein, such that the variant, fragment, derivative, or analog can be activated by cleavage of the proprotein portion to produce an active polypeptide.

Optimizing Codons to Achieve High Levels of Protein Expression in Host Cells

The invention provides methods for modifying amylase-encoding nucleic acids to modify codon usage. In one aspect, the invention provides methods for modifying codons in a nucleic acid encoding an amylase to increase or decrease its expression in a host cell. The invention also provides nucleic acids encoding an amylase modified to increase its expression in a host cell, amylase so modified, and methods of making the modified amylases. The method comprises identifying a "non-preferred" or a "less preferred" codon in amylase-encoding nucleic acid and replacing one or more of these non-preferred or less preferred codons with a "preferred codon" encoding the same amino acid as the replaced codon and at least one non-preferred or less preferred codon in the nucleic acid has been replaced by a preferred codon encoding the same amino acid. A preferred codon is a codon over-represented in coding sequences in genes in the host cell and a non-preferred or less preferred codon is a codon under-represented in coding sequences in genes in the host cell.

Host cells for expressing the nucleic acids, expression cassettes and vectors of the invention include bacteria, yeast, fungi, plant cells, insect cells and mammalian cells. Thus, the invention provides methods for optimizing codon usage in all of these cells, codon-altered nucleic acids and polypeptides made by the codon-altered nucleic acids. Exemplary host cells include gram negative bacteria, such as *Escherichia coli* and *Pseudomonas fluorescens*; gram positive bacteria, such as *Streptomyces diversa, Lactobacillus gasseri, Lactococcus lactis, Lactococcus cremoris, Bacillus subtilis*. Exemplary host cells also include eukaryotic organisms, e.g., various yeast, such as *Saccharomyces* sp., including *Saccharomyces cerevisiae, Schizosaccharomyces pombe, Pichia pastoris*, and *Kluyveromyces lactis, Hansenula polymorpha, Aspergillus niger*, and mammalian cells and cell lines and insect cells and cell lines. Thus, the invention also includes nucleic acids and polypeptides optimized for expression in these organisms and species.

For example, the codons of a nucleic acid encoding an amylase isolated from a bacterial cell are modified such that the nucleic acid is optimally expressed in a bacterial cell different from the bacteria from which the amylase was derived, a yeast, a fungi, a plant cell, an insect cell or a mammalian cell. Methods for optimizing codons are well known in the art, see, e.g., U.S. Pat. No. 5,795,737; Baca (2000) Int. J. Parasitol. 30:113-118; Hale (1998) Protein Expr. Purif. 12:185-188; Narum (2001) Infect. Immun. 69:7250-7253. See also Narum (2001) Infect. Immun. 69:7250-7253, describing optimizing codons in mouse systems; Outchkourov (2002) Protein Expr. Purif. 24:18-24, describing optimizing codons in yeast; Feng (2000) Biochemistry 39:15399-15409, describing optimizing codons in *E. coli*; Humphreys (2000) Protein Expr. Purif. 20:252-264, describing optimizing codon usage that affects secretion in *E. coli*.

Transgenic Non-Human Animals

The invention provides transgenic non-human animals comprising a nucleic acid, a polypeptide (e.g., an amylase), an expression cassette or vector or a transfected or transformed cell of the invention. The invention also provides methods of making and using these transgenic non-human animals.

The transgenic non-human animals can be, e.g., goats, rabbits, sheep, pigs, cows, rats and mice, comprising the nucleic acids of the invention. These animals can be used, e.g., as in vivo models to study amylase activity, or, as models to screen for agents that change the amylase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art; see, e.g., U.S. Pat. Nos. 6,211,428; 6,187,992; 6,156,952; 6,118,044; 6,111,166; 6,107,541; 5,959,171; 5,922,854; 5,892,070; 5,880,327; 5,891,698; 5,639,940; 5,573,933; 5,387,742; 5,087,571, describing making and using transformed cells and eggs and transgenic mice, rats, rabbits, sheep, pigs and cows. See also, e.g., Pollock (1999) J. Immunol. Methods 231:147-157, describing the production of recombinant proteins in the milk of transgenic dairy animals; Baguisi (1999) Nat. Biotechnol. 17:456-461, demonstrating the production of transgenic goats. U.S. Pat. No. 6,211,428, describes making and using transgenic non-human mammals which express in their brains a nucleic acid construct comprising a DNA sequence. U.S. Pat. No. 5,387,742, describes injecting cloned recombinant or synthetic DNA sequences into fertilized mouse eggs, implanting the injected eggs in pseudo-pregnant females, and growing to term transgenic mice whose cells express proteins related to the pathology of Alzheimer's disease. U.S. Pat. No. 6,187,992, describes making and using a transgenic mouse whose genome comprises a disruption of the gene encoding amyloid precursor protein (APP).

"Knockout animals" can also be used to practice the methods of the invention. For example, in one aspect, the transgenic or modified animals of the invention comprise a "knockout animal," e.g., a "knockout mouse," engineered not to express an endogenous gene, which is replaced with a gene expressing an amylase of the invention, or, a fusion protein comprising an amylase of the invention.

Transgenic Plants and Seeds

The invention provides transgenic plants and seeds comprising a nucleic acid, a polypeptide (e.g., an amylase, such as an alpha amylase), an expression cassette or vector or a transfected or transformed cell of the invention. The invention also provides plant products, e.g., oils, seeds, leaves, extracts and the like, comprising a nucleic acid and/or a polypeptide (e.g., an amylase, such as an alpha amylase) of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

Nucleic acids and expression constructs of the invention can be introduced into a plant cell by any means. For example, nucleic acids or expression constructs can be introduced into the genome of a desired plant host, or, the nucleic acids or expression constructs can be episomes. Introduction into the genome of a desired plant can be such that the host's α-amylase production is regulated by endogenous transcriptional or translational control elements. The invention also provides "knockout plants" where insertion of gene sequence by, e.g., homologous recombination, has disrupted the expression of the endogenous gene. Means to generate "knockout" plants are well-known in the art, see, e.g., Strepp (1998) Proc Natl. Acad. Sci. USA 95:4368-4373; Miao (1995) Plant J 7:359-365. See discussion on transgenic plants, below.

The nucleic acids of the invention can be used to confer desired traits on essentially any plant, e.g., on starch-producing plants, such as potato, wheat, rice, barley, and the like. Nucleic acids of the invention can be used to manipulate metabolic pathways of a plant in order to optimize or alter host's expression of α-amylase. The can change the ratio of starch/sugar conversion in a plant. This can facilitate industrial processing of a plant. Alternatively, alpha-amylases of the invention can be used in production of a transgenic plant to produce a compound not naturally produced by that plant. This can lower production costs or create a novel product.

In one aspect, the first step in production of a transgenic plant involves making an expression construct for expression in a plant cell. These techniques are well known in the art. They can include selecting and cloning a promoter, a coding sequence for facilitating efficient binding of ribosomes to mRNA and selecting the appropriate gene terminator sequences. One exemplary constitutive promoter is CaMV35S, from the cauliflower mosaic virus, which generally results in a high degree of expression in plants. Other promoters are more specific and respond to cues in the plant's internal or external environment. An exemplary light-inducible promoter is the promoter from the cab gene, encoding the major chlorophyll a/b binding protein.

In one aspect, the nucleic acid is modified to achieve greater expression in a plant cell. For example, a sequence of the invention is likely to have a higher percentage of A-T nucleotide pairs compared to that seen in a plant, some of which prefer G-C nucleotide pairs. Therefore, A-T nucleotides in the coding sequence can be substituted with G-C nucleotides without significantly changing the amino acid sequence to enhance production of the gene product in plant cells.

Selectable marker gene can be added to the gene construct in order to identify plant cells or tissues that have successfully integrated the transgene. This may be necessary because achieving incorporation and expression of genes in plant cells is a rare event, occurring in just a few percent of the targeted tissues or cells. Selectable marker genes encode proteins that provide resistance to agents that are normally toxic to plants, such as antibiotics or herbicides. Only plant cells that have integrated the selectable marker gene will survive when grown on a medium containing the appropriate antibiotic or herbicide. As for other inserted genes, marker genes also require promoter and termination sequences for proper function.

In one aspect, making transgenic plants or seeds comprises incorporating sequences of the invention and, optionally, marker genes into a target expression construct (e.g., a plasmid), along with positioning of the promoter and the terminator sequences. This can involve transferring the modified gene into the plant through a suitable method. For example, a construct may be introduced directly into the genomic DNA of the plant cell using techniques such as electroporation and microinjection of plant cell protoplasts, or the constructs can be introduced directly to plant tissue using ballistic methods, such as DNA particle bombardment. For example, see, e.g., Christou (1997) Plant Mol. Biol. 35:197-203; Pawlowski (1996) Mol. Biotechnol. 6:17-30; Klein (1987) Nature 327:70-73; Takumi (1997) Genes Genet. Syst. 72:63-69, discussing use of particle bombardment to introduce transgenes into wheat; and Adam (1997) supra, for use of particle bombardment to introduce YACs into plant cells. For example, Rinehart (1997) supra, used particle bombardment to generate transgenic cotton plants. Apparatus for accelerating particles is described U.S. Pat. No. 5,015,580; and, the commercially available BioRad (Biolistics) PDS-2000 particle acceleration instrument; see also, John, U.S. Pat. No. 5,608,148; and Ellis, U.S. Pat. No. 5,681,730, describing particle-mediated transformation of gymnosperms.

In one aspect, protoplasts can be immobilized and injected with a nucleic acids, e.g., an expression construct. Although plant regeneration from protoplasts is not easy with cereals, plant regeneration is possible in legumes using somatic embryogenesis from protoplast derived callus. Organized tissues can be transformed with naked DNA using gene gun technique, where DNA is coated on tungsten microprojectiles, shot 1/100th the size of cells, which carry the DNA deep into cells and organelles. Transformed tissue is then induced to regenerate, usually by somatic embryogenesis. This technique has been successful in several cereal species including maize and rice.

Nucleic acids, e.g., expression constructs, can also be introduced in to plant cells using recombinant viruses. Plant cells can be transformed using viral vectors, such as, e.g., tobacco mosaic virus derived vectors (Rouwendal (1997) Plant Mol. Biol. 33:989-999), see Porta (1996) "Use of viral replicons for the expression of genes in plants," Mol. Biotechnol. 5:209-221.

Alternatively, nucleic acids, e.g., an expression construct, can be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch (1984) Science 233:496-498; Fraley (1983) *Proc. Natl. Acad. Sci. USA* 80:4803 (1983); *Gene Transfer to Plants*, Potrykus, ed. (Springer-Verlag, Berlin 1995). The DNA in an *A. tumefaciens* cell is contained in the bacterial chromosome as well as in another structure known as a Ti (tumor-inducing) plasmid. The Ti plasmid contains a stretch of DNA termed T-DNA (~20 kb long) that is transferred to the plant cell in the infection process and a series of vir (virulence) genes that direct the infection process. *A. tumefaciens* can only infect a plant through wounds: when a plant root or stem is wounded it gives off certain chemical signals, in response to which, the vir genes of *A. tumefaciens* become activated and direct a series of events necessary for the transfer of the T-DNA from the Ti plasmid to the plant's chromosome. The T-DNA then enters the plant cell through the wound. One speculation is that the T-DNA waits until the plant DNA is being replicated or transcribed, then inserts itself into the exposed plant DNA. In order to use *A. tumefaciens* as a transgene vector, the tumor-inducing section of T-DNA have to be removed, while retaining the T-DNA border regions and the vir genes. The transgene is then inserted between the T-DNA border regions, where it is transferred to the plant cell and becomes integrated into the plant's chromosomes.

The invention provides for the transformation of monocotyledonous plants using the nucleic acids of the invention, including important cereals, see Hiei (1997) Plant Mol. Biol. 35:205-218. See also, e.g., Horsch, Science (1984) 233:496; Fraley (1983) Proc. Natl Acad. Sci USA 80:4803; Thykjaer (1997) supra; Park (1996) Plant Mol. Biol. 32:1135-1148, discussing T-DNA integration into genomic DNA. See also D'Halluin, U.S. Pat. No. 5,712,135, describing a process for the stable integration of a DNA comprising a gene that is functional in a cell of a cereal, or other monocotyledonous plant.

In one aspect, the third step can involve selection and regeneration of whole plants capable of transmitting the incorporated target gene to the next generation. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124-176, MacMillilan Publishing Company, New York, 1983; and Binding, *Regeneration of Plants, Plant Protoplasts*, pp. 21-73, CRC Press, Boca Raton, 1985. Regeneration can also be obtained from plant callus, explants, organs, or parts thereof. Such regeneration techniques are described generally in Klee (1987) Ann. Rev. of Plant Phys. 38:467-486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

After the expression cassette is stably incorporated in transgenic plants, it can be introduced into other plants by sexual crossing. Any of a number of standard breeding techniques can be used, depending upon the species to be crossed. Since transgenic expression of the nucleic acids of the invention leads to phenotypic changes, plants comprising the recombinant nucleic acids of the invention can be sexually crossed with a second plant to obtain a final product. Thus, the seed of the invention can be derived from a cross between two transgenic plants of the invention, or a cross between a plant of the invention and another plant. The desired effects (e.g., expression of the polypeptides of the invention to produce a plant in which flowering behavior is altered) can be enhanced when both parental plants express the polypeptides (e.g., an amylase, such as an alpha amylase) of the invention. The desired effects can be passed to future plant generations by standard propagation means.

The nucleic acids and polypeptides of the invention are expressed in or inserted in any plant or seed. Transgenic plants of the invention can be dicotyledonous or monocotyledonous. Examples of monocot transgenic plants of the invention are grasses, such as meadow grass (blue grass, *Poa*), forage grass such as festuca, lolium, temperate grass, such as *Agrostis*, and cereals, e.g., wheat, oats, rye, barley, rice, sorghum, and maize (corn). Examples of dicot transgenic plants of the invention are tobacco, legumes, such as lupins, potato, sugar beet, pea, bean and soybean, and cruciferous plants (family Brassicaceae), such as cauliflower, rape seed, and the closely related model organism *Arabidopsis thaliana*. Thus, the transgenic plants and seeds of the invention include a broad range of plants, including, but not limited to, species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malta, Manihot, Majorana, Medicago, Nicotiana, Olea, Oryza, Panieum, Pannisetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

In alternative embodiments, the nucleic acids of the invention are expressed in plants which contain fiber cells, including, e.g., cotton, silk cotton tree (Kapok, Ceiba pentandra), desert willow, creosote bush, winterfat, balsa, ramie, kenaf, hemp, roselle, jute, sisal abaca and flax. In alternative embodiments, the transgenic plants of the invention can be members of the genus *Gossypium*, including members of any *Gossypium* species, such as *G. arboreum; G. herbaceum, G. barbadense*, and *G. hirsutum*.

The invention also provides for transgenic plants to be used for producing large amounts of the polypeptides (e.g., an amylase, such as an alpha amylase) of the invention. For example, see Palmgren (1997) Trends Genet. 13:348; Chong (1997) Transgenic Res. 6:289-296 (producing human milk protein beta-casein in transgenic potato plants using an auxin-inducible, bidirectional mannopine synthase (mas1', 2') promoter with *Agrobacterium tumefaciens*-mediated leaf disc transformation methods).

Using known procedures, one of skill can screen for plants of the invention by detecting the increase or decrease of transgene mRNA or protein in transgenic plants. Means for detecting and quantitation of mRNAs or proteins are well known in the art.

Polypeptides and Peptides

In one aspect, the invention provides isolated or recombinant polypeptides having a sequence identity (e.g., at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, or complete (100%) sequence identity) to an exemplary sequence of the invention, e.g., SEQ ID NO:2 and subsequences thereof and variants thereof. In one aspect, the polypeptide has an amylase activity, e.g., an alpha amylase activity.

The identity can be over the full length of the polypeptide, or, the identity can be over a region of at least about 50, 60, 70, 80, 90, 100, 150, 200, 250, 300, 350, 400, 450, 500, 550, 600, 650, 700 or more residues. Polypeptides of the invention can also be shorter than the full length of exemplary polypeptides. In alternative aspects, the invention provides polypeptides (peptides, fragments) ranging in size between about 5 and the full length of a polypeptide, e.g., an enzyme, such as an amylase; exemplary sizes being of about 5, 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, or more residues, e.g., contiguous residues of an exemplary amylase of the invention. Peptides of the invention can be useful as, e.g., labeling probes, antigens, toleragens, motifs, amylase active sites.

Polypeptides and peptides of the invention can be isolated from natural sources, be synthetic, or be recombinantly generated polypeptides. Peptides and proteins can be recombinantly expressed in vitro or in vivo. The peptides and polypeptides of the invention can be made and isolated using any method known in the art. Polypeptide and peptides of the invention can also be synthesized, whole or in part, using chemical methods well known in the art. See e.g., Caruthers (1980) Nucleic Acids Res. Symp. Ser. 215-223; Horn (1980) Nucleic Acids Res. Symp. Ser. 225-232; Banga, A. K., Therapeutic Peptides and Proteins, Formulation, Processing and Delivery Systems (1995) Technomic Publishing Co., Lancaster, Pa. For example, peptide synthesis can be performed using various solid-phase techniques (see e.g., Roberge (1995) Science 269:202; Merrifield (1997) Methods Enzymol. 289:3-13) and automated synthesis may be achieved, e.g., using the ABI 431A Peptide Synthesizer (Perkin Elmer) in accordance with the instructions provided by the manufacturer.

The peptides and polypeptides of the invention can also be glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked.

The peptides and polypeptides of the invention, as defined above, include all "mimetic" and "peptidomimetic" forms. The terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has an amylase activity.

Polypeptide mimetic compositions of the invention can contain any combination of non-natural structural components. In alternative aspect, mimetic compositions of the invention include one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. For example, a polypeptide of the invention can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in Chemistry and Biochemistry of Amino Acids, Peptides and Proteins, Vol. 7, pp 267-357, "Peptide Backbone Modifications," Marcell Dekker, NY).

A polypeptide of the invention can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; D- or L-p-methoxy-biphenylphenylalanine; D- or L-2-indole(alkyl) alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a non-natural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R'—N—C—N—R') such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions. Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with, e.g., one or more conventional reagents, including, e.g., phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole. Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4, pentanedione, and transamidase-catalyzed reactions with glyoxylate. Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide. Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide of the invention can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, referred to as the D-amino acid, but also can be referred to as the R- or S-form.

The invention also provides methods for modifying the polypeptides of the invention by either natural processes, such as post-translational processing (e.g., phosphorylation, acylation, etc), or by chemical modification techniques, and the resulting modified polypeptides. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphatidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. See, e.g., Creighton, T. E., Proteins—Structure and Molecular Properties 2nd Ed., W.H. Freeman and Company, New York (1993); Posttranslational Covalent Modification of Proteins, B. C. Johnson, Ed., Academic Press, New York, pp. 1-12 (1983).

Solid-phase chemical peptide synthesis methods can also be used to synthesize the polypeptide or fragments of the invention. Such method have been known in the art since the early 1960's (Merrifield, R. B., J. Am. Chem. Soc., 85:2149-2154, 1963) (See also Stewart, J. M. and Young, J. D., Solid Phase Peptide Synthesis, 2nd Ed., Pierce Chemical Co., Rockford, Ill., pp. 11-12)) and have recently been employed in commercially available laboratory peptide design and synthesis kits (Cambridge Research Biochemicals). Such commercially available laboratory kits have generally utilized the teachings of H. M. Geysen et al, Proc. Natl. Acad. Sci., USA, 81:3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides. In addition, a number of available FMOC peptide synthesis systems are available. For example, assembly of a polypeptide or fragment can be carried out on a solid support using an Applied Biosystems, Inc. Model 431A™ automated peptide synthesizer. Such equipment provides ready access to the peptides of the invention, either by direct synthesis or by synthesis of a series of fragments that can be coupled using other known techniques.

The invention provides novel amylases (e.g., alpha amylases), including the exemplary enzymes of the invention, nucleic acids encoding them, antibodies that bind them, and methods for making and using them. In one aspect, the polypeptides of the invention have an amylase activity, as described herein, including, e.g., the ability to hydrolyze starches into sugars. In one aspect, the polypeptides of the invention have an alpha amylase activity. In alternative aspects, the amylases of the invention have activities that have been modified from those of the exemplary amylases described herein.

The invention includes amylases of the invention with and without signal sequences (including signal sequence of the invention, or other signal sequences) and the signal sequences themselves. The invention also include polypeptides (e.g., fusion proteins) comprising a signal sequence of the invention. The polypeptide comprising a signal sequence of the invention can be an amylase of the invention or another amylase or another enzyme or other polypeptide.

The invention includes immobilized amylases, anti-amylase antibodies and fragments thereof. The invention provides methods for inhibiting amylase activity, e.g, using dominant negative mutants or anti-amylase antibodies of the invention. The invention includes heterocomplexes, e.g., fusion proteins, heterodimers, etc., comprising the amylases of the invention.

In one aspect, amylases (e.g., alpha amylases) of the invention hydrolyze internal polysaccharide bonds, e.g., $\alpha$-1,4- and 1,6-glucosidic bonds in starch to produce smaller molecular weight maltodextrines. In one aspect, this hydrolysis is largely at random. Thus, the invention provides methods for producing smaller molecular weight maltodextrines.

Amylases of the invention can be used in laboratory and industrial settings to hydrolyze starch or any maltodextrine-comprising compound for a variety of purposes. These amylases can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical or industrial samples.

For example, the amylases of the present invention can be formulated in laundry detergents to aid in the removal of starch-containing stains. Amylases of the invention can be used as cleaning agents in detergent matrices (see industrial applications below). The amylases of the present invention can be used in the initial stages (liquefaction) of starch processing, in wet corn milling, in alcohol production, in the textile industry for starch desizing, in baking applications, in the beverage industry, in oilfields in drilling processes; in inking of recycled paper; and in animal feed.

Amylases of the invention can have an amylase activity under various conditions, e.g., extremes in pH and/or temperature, oxidizing agents, and the like. The invention provides methods leading to alternative amylase preparations with different catalytic efficiencies and stabilities, e.g., towards temperature, oxidizing agents and changing wash conditions. In one aspect, amylase variants can be produced using techniques of site-directed mutagenesis and/or random mutagenesis. In one aspect, directed evolution can be used to produce a great variety of amylase variants with alternative specificities and stability.

The proteins of the invention are also useful as research reagents to identify amylase modulators, e.g., activators or inhibitors of amylase activity. Briefly, test samples (compounds, broths, extracts, and the like) are added to amylase assays to determine their ability to inhibit substrate cleavage. Inhibitors identified in this way can be used in industry and research to reduce or prevent undesired proteolysis. As with amylases, inhibitors can be combined to increase the spectrum of activity.

The invention also provides methods of discovering new amylases using the nucleic acids, polypeptides and antibodies of the invention. In one aspect, lambda phage libraries are screened for expression-based discovery of amylases. In one aspect, the invention uses lambda phage libraries in screening to allow detection of toxic clones; improved access to substrate; reduced need for engineering a host, by-passing the potential for any bias resulting from mass excision of the library; and, faster growth at low clone densities. Screening of lambda phage libraries can be in liquid phase or in solid phase. In one aspect, the invention provides screening in liquid phase. This gives a greater flexibility in assay conditions; additional substrate flexibility; higher sensitivity for weak clones; and ease of automation over solid phase screening.

The invention provides screening methods using the proteins and nucleic acids of the invention and robotic automation to enable the execution of many thousands of biocatalytic reactions and screening assays in a short period of time, e.g., per day, as well as ensuring a high level of accuracy and reproducibility (see discussion of arrays, below). As a result, a library of derivative compounds can be produced in a matter of weeks. For further teachings on modification of molecules, including small molecules, see PCT/US94/09174.

The present invention includes amylase enzymes which are non-naturally occurring carbonyl hydrolase variants (e.g., amylase variants) having a different proteolytic activity, stability, substrate specificity, pH profile and/or performance characteristic as compared to the precursor carbonyl hydrolase from which the amino acid sequence of the variant is derived. Specifically, such amylase variants have an amino acid sequence not found in nature, which is derived by substitution of a plurality of amino acid residues of a precursor amylase with different amino acids. The precursor amylase may be a naturally-occurring amylase or a recombinant amylase. The useful amylase variants encompass the substitution of any of the naturally occurring L-amino acids at the designated amino acid residue positions.

Amylase Signal Sequences

The invention provides amylase signal sequences and nucleic acids encoding these signal sequences, e.g., the amino terminal 13 to 36 residues of SEQ ID NO:2. The amylase signal sequences of the invention can be isolated peptides, or, sequences joined to another amylase or a non-amylase polypeptide, e.g., as a fusion protein. In one aspect, the invention provides polypeptides comprising amylase signal sequences of the invention. In one aspect, polypeptides comprising amylase signal sequences of the invention comprise sequences heterologous to an amylase of the invention (e.g., a fusion protein comprising an amylase signal sequence of the invention and sequences from another amylase or a non-amylase protein). In one aspect, the invention provides amylases of the invention with heterologous signal sequences, e.g., sequences with a yeast signal sequence. For example, an amylase of the invention comprising a heterologous signal sequence in a vectors, e.g., a pPIC series vector (Invitrogen, Carlsbad, Calif.).

In one aspect, the signal sequences of the invention are identified following identification of novel amylase polypeptides. The pathways by which proteins are sorted and transported to their proper cellular location are often referred to as protein targeting pathways. One of the most important elements in all of these targeting systems is a short amino acid sequence at the amino terminus of a newly synthesized polypeptide called the signal sequence. This signal sequence directs a protein to its appropriate location in the cell and is removed during transport or when the protein reaches its final destination. Most lysosomal, membrane, or secreted proteins have an amino-terminal signal sequence that marks them for translocation into the lumen of the endoplasmic reticulum. More than 100 signal sequences for proteins in this group have been determined. The signal sequences can vary in length from 13 to 36 amino acid residues. Various methods of recognition of signal sequences are known to those of skill in the art. For example, in one aspect, novel amylase signal peptides are identified by a method referred to as SignalP. SignalP uses a combined neural network which recognizes both signal peptides and their cleavage sites. (Nielsen, et al., "Identification of prokaryotic and eukaryotic signal peptides and prediction of their cleavage sites." Protein Engineering, vol. 10, no. 1, p. 1-6 (1997).

It should be understood that in some aspects amylases of the invention may not have signal sequences. In one aspect, the invention provides the amylases of the invention lacking all or part of a signal sequence, e.g. the signal sequences of the invention. In one aspect, the invention provides a nucleic acid sequence encoding a signal sequence from one amylase operably linked to a nucleic acid sequence of a different amylase or, optionally, a signal sequence from a non-amylase protein may be desired.

Hybrid Amylases and Peptide Libraries

In one aspect, the invention provides hybrid amylases and fusion proteins, including peptide libraries, comprising sequences of the invention. The peptide libraries of the invention can be used to isolate peptide modulators (e.g., activators or inhibitors) of targets, such as amylase substrates, receptors, enzymes. The peptide libraries of the invention can be used to identify formal binding partners of targets, such as ligands, e.g., cytokines, hormones and the like.

In one aspect, the fusion proteins of the invention (e.g., the peptide moiety) are conformationally stabilized (relative to linear peptides) to allow a higher binding affinity for targets. The invention provides fusions of amylases of the invention and other peptides, including known and random peptides. They can be fused in such a manner that the structure of the amylases is not significantly perturbed and the peptide is metabolically or structurally conformationally stabilized. This allows the creation of a peptide library that is easily monitored both for its presence within cells and its quantity.

Amino acid sequence variants of the invention can be characterized by a predetermined nature of the variation, a feature that sets them apart from a naturally occurring form, e.g, an allelic or interspecies variation of an amylase sequence. In one aspect, the variants of the invention exhibit the same qualitative biological activity as the naturally occurring analogue. Alternatively, the variants can be selected for having modified characteristics. In one aspect, while the site or region for introducing an amino acid sequence variation is predetermined, the mutation per se need not be predetermined. For example, in order to optimize the performance of a mutation at a given site, random mutagenesis may be conducted at the target codon or region and the expressed amylase variants screened for the optimal combination of desired activity. Techniques for making substitution mutations at predetermined sites in DNA having a known sequence are well known, as discussed herein for example, M13 primer mutagenesis and PCR mutagenesis. Screening of the mutants can be done using assays of proteolytic activities. In alternative aspects, amino acid substitutions can be single residues; insertions can be on the order of from about 1 to 20 amino acids, although considerably larger insertions can be done. Deletions can range from about 1 to about 20, 30, 40, 50, 60, 70 residues or more. To obtain a final derivative with the optimal properties, substitutions, deletions, insertions or any combination thereof may be used. Generally, these changes are done on a few amino acids to minimize the alteration of the molecule. However, larger changes may be tolerated in certain circumstances.

The invention provides amylases where the structure of the polypeptide backbone, the secondary or the tertiary structure, e.g., an alpha-helical or beta-sheet structure, has been modified. In one aspect, the charge or hydrophobicity has been modified. In one aspect, the bulk of a side chain has been modified. Substantial changes in function or immunological identity are made by selecting substitutions that are less conservative. For example, substitutions can be made which more significantly affect: the structure of the polypeptide backbone in the area of the alteration, for example a alpha-helical or a beta-sheet structure; a charge or a hydrophobic site of the molecule, which can be at an active site; or a side chain. The invention provides substitutions in polypeptide of the invention where (a) a hydrophilic residues, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine. The variants can exhibit the same qualitative biological activity (i.e. amylase activity) although variants can be selected to modify the characteristics of the amylases as needed.

In one aspect, amylases of the invention comprise epitopes or purification tags, signal sequences or other fusion sequences, etc. In one aspect, the amylases of the invention can be fused to a random peptide to form a fusion polypeptide. By "fused" or "operably linked" herein is meant that the random peptide and the amylase are linked together, in such a manner as to minimize the disruption to the stability of the amylase structure, e.g., it retains amylase activity. The fusion polypeptide (or fusion polynucleotide encoding the fusion polypeptide) can comprise further components as well, including multiple peptides at multiple loops.

In one aspect, the peptides and nucleic acids encoding them are randomized, either fully randomized or they are biased in their randomization, e.g. in nucleotide/residue frequency generally or per position. "Randomized" means that each nucleic acid and peptide consists of essentially random nucleotides and amino acids, respectively. In one aspect, the nucleic acids which give rise to the peptides can be chemically synthesized, and thus may incorporate any nucleotide at any position. Thus, when the nucleic acids are expressed to form peptides, any amino acid residue may be incorporated at any position. The synthetic process can be designed to generate randomized nucleic acids, to allow the formation of all or most of the possible combinations over the length of the nucleic acid, thus forming a library of randomized nucleic acids. The library can provide a sufficiently structurally diverse population of randomized expression products to affect a probabilistically sufficient range of cellular responses to provide one or more cells exhibiting a desired response. Thus, the invention provides an interaction library large enough so that at least one of its members will have a structure that gives it affinity for some molecule, protein, or other factor.

Screening Methodologies and "On-Line" Monitoring Devices

In practicing the methods of the invention, a variety of apparatus and methodologies can be used to in conjunction with the polypeptides and nucleic acids of the invention, e.g., to screen polypeptides for amylase activity, to screen compounds as potential modulators, e.g., activators or inhibitors, of an amylase activity, for antibodies that bind to a polypeptide of the invention, for nucleic acids that hybridize to a nucleic acid of the invention, to screen for cells expressing a polypeptide of the invention and the like.

Capillary Arrays

Capillary arrays, such as the GIGAMATRIX™, Diversa Corporation, San Diego, Calif., can be used to in the methods of the invention. Nucleic acids or polypeptides of the invention can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the invention. Capillary arrays provide another system for holding and screening samples. For example, a sample screening apparatus can include a plurality of capillaries formed into an array of adjacent capillaries, wherein each capillary comprises at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample.

A polypeptide or nucleic acid, e.g., a ligand, can be introduced into a first component into at least a portion of a capillary of a capillary array. Each capillary of the capillary array can comprise at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array comprises at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube.

The capillary array can include a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Arrays, or "Biochips"

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of an amylase gene. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins. The present invention can be practiced with any known "array," also referred to as a "microarray" or "nucleic acid array" or "polypeptide array" or "antibody array" or "biochip," or variation thereof Arrays are generically a plurality of "spots" or "target elements," each target element comprising a defined amount of one or more biological molecules, e.g., oligonucleotides, immobilized onto a defined area of a substrate surface for specific binding to a sample molecule, e.g., mRNA transcripts.

In practicing the methods of the invention, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765.

Antibodies and Antibody-Based Screening Methods

The invention provides isolated or recombinant antibodies that specifically bind to an amylase of the invention. These antibodies can be used to isolate, identify or quantify the amylases of the invention or related polypeptides. These antibodies can be used to isolate other polypeptides within the scope the invention or other related amylases. The antibodies can be designed to bind to an active site of an amylase. Thus, the invention provides methods of inhibiting amylases using the antibodies of the invention.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the invention. Alternatively, the methods of the invention can be used to modify the structure of an antibody produced by a cell to be modified, e.g., an antibody's affinity can be increased or decreased. Furthermore, the ability to make or modify antibodies can be a phenotype engineered into a cell by the methods of the invention.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, NY (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) Nature 256:495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) Trends Biotechnol. 15:62-70; Katz (1997) Annu. Rev. Biophys. Biomol. Struct. 26:27-45.

Polypeptides or peptides can be used to generate antibodies which bind specifically to the polypeptides, e.g., the amylases, of the invention. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the invention.

In immunoaffinity procedures, the antibody is attached to a solid support, such as a bead or other column matrix. The protein preparation is placed in contact with the antibody under conditions in which the antibody specifically binds to one of the polypeptides of the invention. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the invention can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the invention. Alternatively, transgenic mice may be used to express humanized antibodies to these polypeptides or fragments thereof.

Antibodies generated against the polypeptides of the invention may be used in screening for similar polypeptides (e.g., amylases) from other organisms and samples. In such techniques, polypeptides from the organism are contacted with the antibody and those polypeptides which specifically bind the antibody are detected. Any of the procedures described above may be used to detect antibody binding.

Kits

The invention provides kits comprising the compositions, e.g., nucleic acids, expression cassettes, vectors, cells, transgenic seeds or plants or plant parts, polypeptides (e.g., amylases) and/or antibodies of the invention. The kits also can contain instructional material teaching the methodologies and industrial uses of the invention, as described herein.

Measuring Metabolic Parameters

The methods of the invention provide whole cell evolution, or whole cell engineering, of a cell to develop a new cell strain having a new phenotype, e.g., a new or modified amylase activity, by modifying the genetic composition of the cell. The genetic composition can be modified by addition to the cell of a nucleic acid of the invention. To detect the new phenotype, at least one metabolic parameter of a modified cell is monitored in the cell in a "real time" or "on-line" time frame. In one aspect, a plurality of cells, such as a cell culture, is monitored in "real time" or "on-line." In one aspect, a plurality of metabolic parameters is monitored in "real time" or "on-line." Metabolic parameters can be monitored using the amylases of the invention.

Metabolic flux analysis (MFA) is based on a known biochemistry framework. A linearly independent metabolic matrix is constructed based on the law of mass conservation and on the pseudo-steady state hypothesis (PSSH) on the intracellular metabolites. In practicing the methods of the invention, metabolic networks are established, including the:

identity of all pathway substrates, products and intermediary metabolites identity of all the chemical reactions interconverting the pathway metabolites, the stoichiometry of the pathway reactions, identity of all the enzymes catalyzing the reactions, the enzyme reaction kinetics, the regulatory interactions between pathway components, e.g. allosteric interactions, enzyme-enzyme interactions etc, intracellular compartmentalization of enzymes or any other supramolecular organization of the enzymes, and, the presence of any concentration gradients of metabolites, enzymes or effector molecules or diffusion barriers to their movement.

Once the metabolic network for a given strain is built, mathematic presentation by matrix notion can be introduced to estimate the intracellular metabolic fluxes if the on-line metabolome data is available. Metabolic phenotype relies on the changes of the whole metabolic network within a cell. Metabolic phenotype relies on the change of pathway utilization with respect to environmental conditions, genetic regulation, developmental state and the genotype, etc. In one aspect of the methods of the invention, after the on-line MFA calculation, the dynamic behavior of the cells, their phenotype and other properties are analyzed by investigating the pathway utilization. For example, if the glucose supply is increased and the oxygen decreased during the yeast fermentation, the utilization of respiratory pathways will be reduced and/or stopped, and the utilization of the fermentative pathways will dominate. Control of physiological state of cell cultures will become possible after the pathway analysis. The methods of the invention can help determine how to manipulate the fermentation by determining how to change the substrate supply, temperature, use of inducers, etc. to control the physiological state of cells to move along desirable direction. In practicing the methods of the invention, the MFA results can also be compared with transcriptome and proteome data to design experiments and protocols for metabolic engineering or gene shuffling, etc.

In practicing the methods of the invention, any modified or new phenotype can be conferred and detected, including new or improved characteristics in the cell. Any aspect of metabolism or growth can be monitored.

Monitoring Expression of an mRNA Transcript

In one aspect of the invention, the engineered phenotype comprises increasing or decreasing the expression of an mRNA transcript (e.g., an amylase message) or generating new (e.g., amylase) transcripts in a cell. This increased or decreased expression can be traced by testing for the presence of an amylase of the invention or by amylase activity assays. mRNA transcripts, or messages, also can be detected and quantified by any method known in the art, including, e.g., Northern blots, quantitative amplification reactions, hybridization to arrays, and the like. Quantitative amplification reactions include, e.g., quantitative PCR, including, e.g., quantitative reverse transcription polymerase chain reaction, or RT-PCR; quantitative real time RT-PCR, or "real-time kinetic RT-PCR" (see, e.g., Kreuzer (2001) Br. J. Haematol. 114:313-318; Xia (2001) Transplantation 72:907-914).

In one aspect of the invention, the engineered phenotype is generated by knocking out expression of a homologous gene. The gene's coding sequence or one or more transcriptional control elements can be knocked out, e.g., promoters or enhancers. Thus, the expression of a transcript can be completely ablated or only decreased.

In one aspect of the invention, the engineered phenotype comprises increasing the expression of a homologous gene. This can be effected by knocking out of a negative control element, including a transcriptional regulatory element acting in cis- or trans-, or, mutagenizing a positive control element. One or more, or, all the transcripts of a cell can be measured by hybridization of a sample comprising transcripts of the cell, or, nucleic acids representative of or complementary to transcripts of a cell, by hybridization to immobilized nucleic acids on an array.

Monitoring Expression of a Polypeptides, Peptides and Amino Acids

In one aspect of the invention, the engineered phenotype comprises increasing or decreasing the expression of a polypeptide (e.g., an amylase) or generating new polypeptides in a cell. This increased or decreased expression can be traced by determining the amount of amylase present or by amylase activity assays. Polypeptides, peptides and amino acids also can be detected and quantified by any method known in the art, including, e.g., nuclear magnetic resonance (NMR), spectrophotometry, radiography (protein radiolabeling), electrophoresis, capillary electrophoresis, high performance liquid chromatography (HPLC), thin layer chromatography (TLC), hyperdiffusion chromatography, various immunological methods, e.g. immunoprecipitation, immunodiffusion, immuno-electrophoresis, radioimmunoassays (RIAs), enzyme-linked immunosorbent assays (ELISAs), immuno-fluorescent assays, gel electrophoresis (e.g., SDS-PAGE), staining with antibodies, fluorescent activated cell sorter (FACS), pyrolysis mass spectrometry, Fourier-Transform Infrared Spectrometry, Raman spectrometry, GC-MS, and LC-Electrospray and cap-LC-tandem-electrospray mass spectrometries, and the like. Novel bioactivities can also be screened using methods, or variations thereof, described in U.S. Pat. No. 6,057,103. Furthermore, as discussed below in detail, one or more, or, all the polypeptides of a cell can be measured using a protein array.

INDUSTRIAL APPLICATIONS

Detergent Compositions

The invention provides detergent compositions comprising one or more polypeptides of the invention, and methods of making and using these compositions. The invention incorporates all methods of making and using detergent compositions, see, e.g., U.S. Pat. Nos. 6,413,928; 6,399,561; 6,365,561; 6,380,147. The detergent compositions can be a one and two part aqueous composition, a non-aqueous liquid composition, a cast solid, a granular form, a particulate form, a compressed tablet, a gel and/or a paste and a slurry form. The invention also provides methods capable of a rapid removal of gross food soils, films of food residue and other minor food compositions using these detergent compositions. Amylases of the invention can facilitate the removal of starchy stains by means of catalytic hydrolysis of the starch polysaccharide. Amylases of the invention can be used in dishwashing detergents in textile laundering detergents.

The actual active enzyme content depends upon the method of manufacture of a detergent composition and is not critical, assuming the detergent solution has the desired enzymatic activity. In one aspect, the amount of amylase present in the final solution ranges from about 0.001 mg to 0.5 mg per gram of the detergent composition. The particular enzyme chosen for use in the process and products of this invention depends upon the conditions of final utility, including the physical product form, use pH, use temperature, and soil types to be degraded or altered. The enzyme can be chosen to provide optimum activity and stability for any given set of utility conditions. In one aspect, the polypeptides of the present invention are active in the pH ranges of from about 4 to about 12 and in the temperature range of from about 20° C. to about 95° C. The detergents of the invention can comprise cationic, semi-polar nonionic or zwitterionic surfactants; or, mixtures thereof.

Amylases of the present invention can be formulated into powdered and liquid detergents having pH between 4.0 and 12.0 at levels of about 0.01 to about 5% (preferably 0.1% to 0.5%) by weight. These detergent compositions can also include other enzymes such as known proteases, cellulases, lipases or endoglycosidases, as well as builders and stabilizers. The addition of amylases of the invention to conventional cleaning compositions does not create any special use limitation. In other words, any temperature and pH suitable for the detergent is also suitable for the present compositions as long as the pH is within the above range, and the temperature is below the described enzyme's denaturing temperature. In addition, the polypeptides of the invention can be used in a cleaning composition without detergents, again either alone or in combination with builders and stabilizers.

The present invention provides cleaning compositions including detergent compositions for cleaning hard surfaces, detergent compositions for cleaning fabrics, dishwashing compositions, oral cleaning compositions, denture cleaning compositions, and contact lens cleaning solutions.

In one aspect, the invention provides a method for washing an object comprising contacting the object with a polypeptide of the invention under conditions sufficient for washing. A polypeptide of the invention may be included as a detergent additive. The detergent composition of the invention may, for example, be formulated as a hand or machine laundry detergent composition comprising a polypeptide of the invention. A laundry additive suitable for pre-treatment of stained fabrics can comprise a polypeptide of the invention. A fabric softener composition can comprise a polypeptide of the invention. Alternatively, a polypeptide of the invention can be formulated as a detergent composition for use in general household hard surface cleaning operations. In alternative aspects, detergent additives and detergent compositions of the invention may comprise one or more other enzymes such as a protease, a lipase, a cutinase, another amylase, a carbohydrase, a cellulase, a pectinase, a mannanase, an arabinase, a galactanase, a xylanase, an oxidase, e.g., a lactase, and/or a peroxidase. The properties of the enzyme(s) of the invention are chosen to be compatible with the selected detergent (i.e. pH-optimum, compatibility with other enzymatic and non-enzymatic ingredients, etc.) and the enzyme(s) is present in effective amounts. In one aspect, amylase enzymes of the invention are used to remove malodorous materials from fabrics. Various detergent compositions and methods for making them that can be used in practicing the invention are described in, e.g., U.S. Pat. Nos. 6,333,301; 6,329,333; 6,326,341; 6,297,038; 6,309,871; 6,204,232; 6,197,070; 5,856,164.

Treating Fabrics

The invention provides methods of treating fabrics using one or more polypeptides of the invention. The polypeptides of the invention can be used in any fabric-treating method, which are well known in the art, see, e.g., U.S. Pat. No. 6,077,316. For example, in one aspect, the feel and appearance of a fabric is improved by a method comprising contacting the fabric with an amylase of the invention in a solution. In one aspect, the fabric is treated with the solution under pressure.

In one aspect, the enzymes of the invention are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes of the invention can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. The invention provides a method of desizing comprising enzymatic hydrolysis of the size by the action of an enzyme of the invention.

The enzymes of the invention can be used to desize fabrics, including cotton-containing fabrics, as detergent additives, e.g., in aqueous compositions. The invention provides methods for producing a stonewashed look on indigo-dyed denim fabric and garments. For the manufacture of clothes, the fabric can be cut and sewn into clothes or garments, which is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The invention provides methods of finishing denim garments (e.g., a "bio-stoning process"), enzymatic desizing and providing softness to fabrics using the amylases of the invention. The invention provides methods for quickly softening denim garments in a desizing and/or finishing process.

Foods and Food Processing

The enzymes of the invention have numerous applications in food processing industry. The amylases of the invention are used in starch to fructose processing. Starch to fructose processing can consist of four steps: liquefaction of granular starch, saccharification of the liquefied starch into dextrose, purification, and isomerization to fructose.

The invention provides methods of starch liquefaction using the enzymes of the invention. Concentrated suspensions of starch polymer granules are converted into a solution of soluble shorter chain length dextrins of low viscosity. This step is useful for convenient handling with standard equipment and for efficient conversion to glucose or $10^3$ other sugars. In one aspect, the granular starch is liquefied by gelatinizing the granules by raising the temperature of the granular starch to over about 72° C. The heating process instantaneously disrupts the insoluble starch granules to produce a water soluble starch solution. The solubilized starch solution can then be liquefied by an amylase of the invention. Thus, the invention provides enzymatic starch liquefaction processes using an amylase of the invention.

An exemplary enzymatic liquefaction process involves adjusting the pH of a granular starch slurry to between 6.0 and 6.5 and the addition of calcium hydroxide, sodium hydroxide or sodium carbonate. In one aspect, calcium hydroxide is added. This provides calcium ions to stabilize the glucoamylase of the invention against inactivation. In one aspect, upon addition of amylase, the suspension is pumped through a steam jet to instantaneously raise the temperature to between 80°-115° C. In one aspect, the starch is immediately gelatinized and, due to the presence of amylase, depolymerized through random hydrolysis of $\alpha$-1, 4-glycosidic bonds by amylase to a fluid mass. The fluid mass can be easily pumped.

The invention provides various enzymatic starch liquefaction processes using an amylase of the invention. In one aspect of the liquefaction process of the invention, an amylase is added to the starch suspension and the suspension is held at a temperature of between about 80°-100° C. to partially hydrolyze the starch granules. In one aspect, the partially hydrolyzed starch suspension is pumped through a jet at temperatures in excess of about 105° C. to thoroughly gelatinize any remaining granular structure. In one aspect, after cooling the gelatinized starch, a second addition of amylase is made to further hydrolyze the starch.

The invention provides enzymatic dry milling processes using an amylase of the invention. In dry milling, whole grain is ground and combined with water. The germ is optionally removed by flotation separation or equivalent techniques. The resulting mixture, which contains starch, fiber, protein and other components of the grain, is liquefied using amylase. In one aspect, enzymatic liquefaction is done at lower temperatures than the starch liquification processes discussed above. In one aspect, after gelatinization the starch solution is held at an elevated temperature in the presence of amylase until a DE of 10-20 is achieved. In one aspect, this is a period of about 1-3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The invention provides wet milling processes, e.g., corn wet milling, using an amylase of the invention. Corn wet milling is a process which produces corn oil, gluten meal, gluten feed and starch. Thus, the invention provides methods of making corn oil, gluten meal, gluten feed and starch using an enzyme of the invention. In one aspect, an alkaline-amylase of the invention is used in the liquefaction of starch. In one aspect, glucoamylase is used in saccharification to produce glucose.

In one aspect, corn (a kernel that consists of a outer seed coat (fiber), starch, a combination of starch and glucose and the inner germ), is subjected to a four step process, which results in the production of starch. In one aspect, the corn is steeped, de-germed, de-fibered, and the gluten is separated. In a steeping process the solubles are taken out. The product remaining after removal of the solubles is de-germed, resulting in production of corn oil and production of an oil cake, which is added to the solubles from the steeping step. The remaining product is de-fibered and the fiber solids are added to the oil cake/solubles mixture. This mixture of fiber solids, oil cake and solubles forms a gluten feed. After de-fibering, the remaining product is subjected to gluten separation. This separation results in a gluten meal and starch. The starch is then subjected to liquefaction and saccharification using polypeptides of the invention to produce glucose.

The invention provides anti-staling processes (e.g., of baked products such as bread) using an amylase of the invention. The invention provides methods to slow the increase of the firmness of the crumb (of the baked product) and a decrease of the elasticity of the crumb using an amylase of the invention. Staling of baked products (such as bread) is more serious as time passes between the moment of preparation of the bread product and the moment of consumption. The term staling is used to describe changes undesirable to the consumer in the properties of the bread product after leaving the oven, such as an increase of the firmness of the crumb, a decrease of the elasticity of the crumb, and changes in the crust, which becomes tough and leathery. The firmness of the bread crumb increases further during storage up to a level, which is considered as negative. Amylases of the invention are used to retard staling of the bread as described e.g., in U.S. Pat. Nos. 6,197,352; 2,615,810 and 3,026,205; Silberstein (1964) Baker's Digest 38:66-72.

In one aspect, an enzyme of the invention is used to retard the staling of baked products while not hydrolyzing starch into the branched dextrins. Branched dextrins are formed by cleaving off the branched chains of the dextrins generated by $\alpha$-amylase hydrolysis which cannot be degraded further by the $\alpha$-amylase. This can produce a gummy crumb in the resulting bread. Accordingly, the invention provides a process for retarding the staling of baked products (e.g., leavened baked products) comprising adding an enzyme of the invention comprising exoamylase activity to a flour or a dough used for producing a baked product. Exoamylases of the invention can have glucoamylase, $\beta$-amylase (which releases maltose in the beta-configuration) and/or maltogenic amylase activity.

The invention also provides a process for preparing a dough or a baked product prepared from the dough which comprises adding an amylase of the invention to the dough in an amount which is effective to retard the staling of the bread. The invention also provides a dough comprising said amylase and a premix comprising flour together with said amylase. Finally, the invention provides an enzymatic baking additive, which contains said amylase.

The invention also provides a high yield process for producing high quality corn fiber gum by treatment of corn fiber with an enzyme of the invention followed by hydrogen peroxide treatment to obtain an extract of milled corn fiber. See, e.g., U.S. Pat. No. 6,147,206.

Animal Feeds and Additives

The invention provides methods for treating animal feeds and additives using amylase enzymes of the invention. The invention provides animal feeds and additives comprising amylases of the invention. In one aspect, treating animal feeds and additives using amylase enzymes of the invention can help in the availability of starch in the animal feed or additive. This can result in release of readily digestible and easily absorbed sugars.

Use of an amylase of the invention can increase the digestive capacity of animals and birds. Use of an amylase of the invention can ensure availability of an adequate nutrient supply for better growth and performance. In one aspect, the enzymes of the invention can be added as feed additives for animals. In another aspect, the animal feed can be treated with amylases prior to animal consumption. In another aspect, the amylases may be supplied by expressing the enzymes directly in transgenic feed crops (as, e.g., transgenic plants, seeds and the like), such as corn. As discussed above, the invention provides transgenic plants, plant parts and plant cells comprising a nucleic acid sequence encoding a polypeptide of the invention. In one aspect, the nucleic acid is expressed such that the amylase is produced in recoverable quantities. The amylase can be recovered from any plant or plant part. Alternatively, the plant or plant part containing the recombinant polypeptide can be used as such for improving the quality of a food or feed, e.g., improving nutritional value, palatability, and rheological properties, or to destroy an antinutritive factor.

Paper or Pulp Treatment

The enzymes of the invention can be in paper or pulp treatment or paper deinking.

For example, in one aspect, the invention provides a paper treatment process using amylases of the invention. In one aspect, the enzymes of the invention can be used to modify starch in the paper thereby converting it into a liquefied form. In another aspect, paper components of recycled photocopied paper during chemical and enzymatic deinking processes. In one aspect, amylases of the invention can be used in combination with cellulases. The paper can be treated by the following three processes: 1) disintegration in the presence of an enzyme of the invention, 2) disintegration with a deinking chemical and an enzyme of the invention, and/or 3) disintegration after soaking with an enzyme of the invention. The recycled paper treated with amylase can have a higher brightness due to removal of toner particles as compared to the paper treated with just cellulase. While the invention is not limited by any particular mechanism, the effect of an amylase of the invention may be due to its behavior as surface-active agents in pulp suspension.

The invention provides methods of treating paper and paper pulp using one or more polypeptides of the invention. The polypeptides of the invention can be used in any paper- or pulp-treating method, which are well known in the art, see, e.g., U.S. Pat. Nos. 6,241,849; 6,066,233; 5,582,681. For example, in one aspect, the invention provides a method for deinking and decolorizing a printed paper containing a dye, comprising pulping a printed paper to obtain a pulp slurry, and dislodging an ink from the pulp slurry in the presence of an enzyme of the invention (other enzymes can also be added). In another aspect, the invention provides a method for enhancing the freeness of pulp, e.g., pulp made from secondary fiber, by adding an enzymatic mixture comprising an enzyme of the invention (can also include other enzymes, e.g., pectinase enzymes) to the pulp and treating under conditions to cause a reaction to produce an enzymatically treated pulp. The freeness of the enzymatically treated pulp is increased from the initial freeness of the secondary fiber pulp without a loss in brightness.

Repulping: Treatment of Lignocellulosic Materials

The invention also provides a method for the treatment of lignocellulosic fibers, wherein the fibers are treated with a polypeptide of the invention, in an amount which is efficient for improving the fiber properties. The amylases of the invention may also be used in the production of lignocellulosic materials such as pulp, paper and cardboard, from starch reinforced waste paper and cardboard, especially where repulping occurs at pH above 7 and where amylases can facilitate the disintegration of the waste material through degradation of the reinforcing starch. The amylases of the invention can be useful in a process for producing a paper-making pulp from starch-coated printed paper. The process may be performed as described in, e.g., WO 95/14807.

An exemplary process comprises disintegrating the paper to produce a pulp, treating with a starch-degrading enzyme before, during or after the disintegrating, and separating ink particles from the pulp after disintegrating and enzyme treatment. See also U.S. Pat. No. 6,309,871 and other US patents cited herein. Thus, the invention includes a method for enzymatic deinking of recycled paper pulp, wherein the polypeptide is applied in an amount which is efficient for effective de-inking of the fiber surface.

Waste Treatment

The enzymes of the invention can be used in a variety of other industrial applications, e.g., in waste treatment. For example, in one aspect, the invention provides a solid waste digestion process using enzymes of the invention. The methods can comprise reducing the mass and volume of substantially untreated solid waste. Solid waste can be treated with an enzymatic digestive process in the presence of an enzymatic solution (including an enzyme of the invention) at a controlled temperature. This results in a reaction without appreciable bacterial fermentation from added microorganisms. The solid waste is converted into a liquefied waste and any residual solid waste. The resulting liquefied waste can be separated from said any residual solidified waste. See e.g., U.S. Pat. No. 5,709,796.

Oral Care Products

The invention provides oral care product comprising an amylase of the invention. Exemplary oral care products include toothpastes, dental creams, gels or tooth powders, odontics, mouth washes, pre- or post brushing rinse formulations, chewing gums, lozenges, or candy. See, e.g., U.S. Pat. No. 6,264,925.

Brewing and Fermenting

The invention provides methods of brewing (e.g., fermenting) beer comprising an amylase of the invention. In one exemplary process, starch-containing raw materials are disintegrated and processed to form a malt. An amylase of the invention is used at any point in the fermentation process. For example, amylases of the invention can be used in the processing of barley malt. The major raw material of beer brewing is barley malt. This can be a three stage process. First, the barley grain can be steeped to increase water content, e.g., to around about 40%. Second, the grain can be germinated by incubation at 15-25° C. for 3 to 6 days when enzyme synthesis is stimulated under the control of gibberellins. During this time amylase levels rise significantly. In one aspect, amylases of the invention are added at this (or any other) stage of the process. The action of the amylase results in an increase in fermentable reducing sugars. This can be expressed as the diastatic power, DP, which can rise from around 80 to 190 in 5 days at 12° C.

Amylases of the invention can be used in any beer producing process, as described, e.g., in U.S. Pat. Nos. 5,762,991; 5,536,650; 5,405,624; 5,021,246; 4,788,066.

OTHER INDUSTRIAL APPLICATIONS

The invention also includes a method of increasing the flow of production fluids from a subterranean formation by removing a viscous, starch-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

In summary, the invention provides enzymes and processes for hydrolyzing liquid (liquefied) and granular starch. Such starch can be derived from any source, e.g., corn, wheat, milo, sorghum, rye or bulgher. The invention applies to any grain starch source which is useful in liquefaction, e.g., any other grain or vegetable source known to produce starch suitable for liquefaction. The methods of the invention comprise liquefying starch from any natural material, such as rice, germinated rice, corn, barley, milo, wheat, legumes and sweet potato. The liquefying process can substantially hydrolyze the starch to produce a syrup. The temperature range of the liquefaction can be any liquefaction temperature which is known to be effective in liquefying starch. For example, the temperature of the starch can be between about 80° C. to about 115° C., between about 100° C. to about 110° C., and from about 105° C. to about 108° C.

In one aspect, the invention includes a method for liquefying a starch containing composition comprising contacting the starch with a polypeptide of the invention (e.g., a purified polypeptide selected from polypeptides having an amino acid sequence selected from the group consisting of: SEQ ID NO:2; variants having at least about 50% homology to at least one of SEQ ID NO:2, over a region of at least about 100 residues, as determined by analysis with a sequence comparison algorithm or by visual inspection; sequences complementary to SEQ ID NO:2; and sequences complementary to variants having at least about 50% homology to SEQ ID NO:2 over a region of at least about 100 residues, as determined by analysis with a sequence comparison algorithm or by visual inspection; and polypeptides having at least 10 consecutive amino acids of a polypeptide having a sequence selected from the group consisting of SEQ ID NO:2). In one aspect, the polypeptide is set forth in SEQ ID NO:2. The starch may be from a material selected from rice, germinated rice, corn, barley, wheat, legumes and sweet potato. A glucose syrup produced by the method of the invention is included herein and is described in the examples. Such a syrup can be a maltose syrup, a glucose syrup, or a combination thereof. In particular, the syrups produced using the amylases of the invention there is a higher level of DP2 fraction and a higher level of DP3 (maltotriose and/or panose) and less of the greater than DP7 fragments as compared to the syrups produced by commercial enzymes. This is consistent with the liquefaction profile since less of the large fragments are in the invention liquefied syrups.

The invention also provides a method for removing starch containing stains from a material comprising contacting the material with a polypeptide of the invention. In one aspect, the invention provides a method for washing an object comprising contacting the object with a polypeptide of the invention under conditions sufficient for washing. A polypeptide of the invention may be included as a detergent additive for example. The invention also includes a method for textile desizing comprising contacting the textile with a polypeptide of the invention under conditions sufficient for desizing.

The invention also provides a method of reducing the staling of bakery products comprising addition of a polypeptide of the invention to the bakery product, prior to baking.

The invention also provides a method for the treatment of lignocellulosic fibers, wherein the fibers are treated with a polypeptide of the invention, in an amount which is efficient for improving the fiber properties. The invention includes a method for enzymatic deinking of recycled paper pulp, wherein the polypeptide is applied in an amount which is efficient for effective deinking of the fiber surface.

Any of the methods described herein include the possibility of the addition of a second alpha amylase or a beta amylase or a combination thereof. Commercial amylases or other enzymes suitable for use in combination with an enzyme of the invention are known to those of skill in the art.

The invention also includes a method of increasing the flow of production fluids from a subterranean formation by removing a viscous, starch-containing, damaging fluid formed during production operations and found within the subterranean formation which surrounds a completed well bore comprising allowing production fluids to flow from the well bore; reducing the flow of production fluids from the formation below expected flow rates; formulating an enzyme treatment by blending together an aqueous fluid and a polypeptide of the invention; pumping the enzyme treatment to a desired location within the well bore; allowing the enzyme treatment to degrade the viscous, starch-containing, damaging fluid, whereby the fluid can be removed from the subterranean formation to the well surface; and wherein the enzyme treatment is effective to attack the alpha glucosidic linkages in the starch-containing fluid.

The present invention exploits the unique catalytic properties of enzymes. Whereas the use of biocatalysts (i.e., purified or crude enzymes, non-living or living cells) in chemical transformations normally requires the identification of a particular biocatalyst that reacts with a specific starting compound, the present invention uses selected biocatalysts and reaction conditions that are specific for functional groups that are present in many starting compounds. Each biocatalyst is specific for one functional group, or several related functional groups, and can react with many starting compounds containing this functional group. The biocatalytic reactions produce a population of derivatives from a single starting compound. These derivatives can be subjected to another round of biocatalytic reactions to produce a second population of derivative compounds. Thousands of variations of the original compound can be produced with each iteration of biocatalytic derivatization.

Enzymes react at specific sites of a starting compound without affecting the rest of the molecule, a process which is very difficult to achieve using traditional chemical methods. This high degree of biocatalytic specificity provides the means to identify a single active compound within the library. The library is characterized by the series of biocatalytic reactions used to produce it, a so-called "biosynthetic history". Screening the library for biological activities and tracing the biosynthetic history identifies the specific reaction sequence producing the active compound. The reaction sequence is repeated and the structure of the synthesized compound determined. This mode of identification, unlike other synthesis and screening approaches, does not require immobilization technologies, and compounds can be synthesized and tested free in solution using virtually any type of screening assay. It is important to note, that the high degree of specificity of enzyme reactions on functional groups allows for the "tracking" of specific enzymatic reactions that make up the biocatalytically produced library.

Many of the procedural steps are performed using robotic automation enabling the execution of many thousands of biocatalytic reactions and screening assays per day as well as ensuring a high level of accuracy and reproducibility. As a result, a library of derivative compounds can be produced in a matter of weeks which would take years to produce using current chemical methods. (For further teachings on modification of molecules, including small molecules, see, e.g., PCT/US94/09174).

The invention will be further described with reference to the following examples; however, it is to be understood that the invention is not limited to such examples.

EXAMPLES

Example 1: Identification and Characterization of Thermostable α-Amylases

The following example describes an exemplary method for determining if a polypeptide is within the scope of the invention. This example describes the identification of novel amylases. A screening program can be carried out under neutral and/or low pH conditions. DNA libraries generated from low pH samples can be targeted for discovery.
Biochemical Studies Biochemical analysis of genomic clones can show if any have pH optima of less than pH 6. Lysates of these genomic clones can be tested for thermal tolerance by incubation at 70° C., 80° C., 90° C. or 100° C. for 10 minutes and measurement of residual activity at pH 4.5. Those clones retaining >50% activity after heat treatment at 80° C. can be chosen for further analysis. These clones can be incubated at 90° C. for 10 minutes at pH 6.0 and 4.5 and tested for residual activity at pH 4.5.

Thermal activity of the clones with residual activity after heat treatment at 90° C. at pH 4.5 can be measured at room temperature, 70° C. and 90° C. at pH 4.5.

Example 2: Thermostable Amylases Active at Alkaline pH

The following example describes an exemplary method for determining if a polypeptide is within the scope of the invention, e.g., is a thermostable amylase.
Biochemical Studies Soluble, active protein can be successfully purified to homogeneity and measured at pH 8 and pH 10 (40° C. and 50° C.) using 2% starch in buffer.
Stability Activity can be measured at pH 8 and 50° C. after a 30 minute incubation at 50° C. in the presence of various components of an ADW formulation; pH 8, pH 10.8, ADW solution (with bleach) and ADW solution (without bleach). The measured activity after the incubation can be expressed as a percentage of the original activity.
Wash Tests Wash tests using starch coated slides can be carried out to gauge the performance of each of the purified enzymes as compared to the commercial amylase. The spaghetti starch coated slides can be prepared according to manufacturer's protocol. Two pre-weighed starch coated slides can be placed back to back in a 50 mL conical tube and 25 mL of ADW solution, +/−enzyme were added per tube. The tubes can be incubated for 20 minutes at 50° C. with gentle rotation on a vertical carousel. Following the incubation period, the slides are immediately rinsed in water and oven dried overnight. Trials can be run in duplicate and a commercial enzyme can be run as a positive control.

Example 3: Amylase Activity Assay: BCA Reducing Ends Assay

Figure 5:
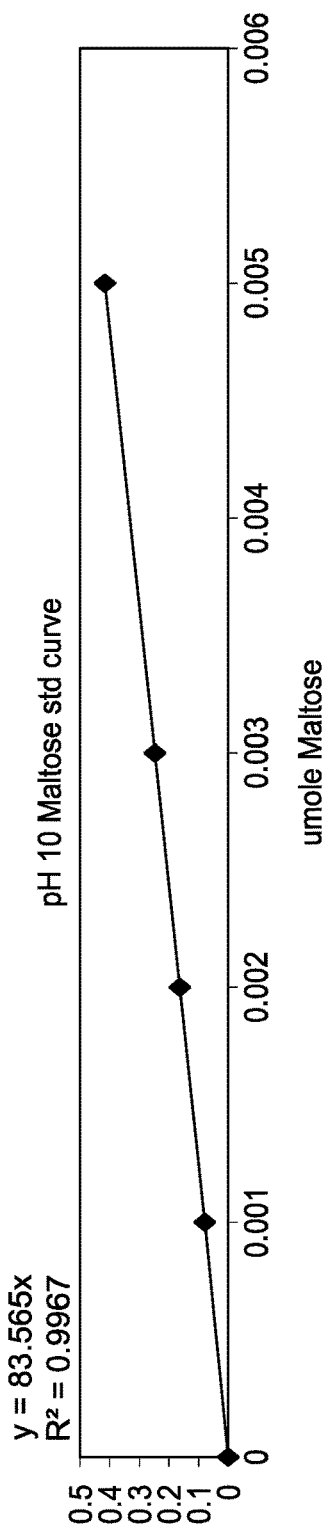
FIG. 5 illustrates a sample Standard Curve of the assay of Example 3.

The following example describes an exemplary method for determining if a polypeptide is within the scope of the invention, for example, by a BCA reducing ends assay. Amylase activity of clones of interest was determined using the following methodology.
1. Prepare 2 substrate solutions, as follows:
  a) 2% soluble starch (potato) pH 8 solution by dissolving 2 gm potato starch in 100 ml 100 mM sodium phosphate pH 8).
  b) 2% soluble starch (potato) pH 10 solution by dissolving 2 gm potato starch in 100 ml 100 mM sodium carbonate.
Heat both solutions in a boiling water bath, while mixing, for 30-40 minutes until starch dissolves.
2. Prepare Solution A from 64 mg/ml sodium carbonate monohydrate, 24 mg/ml sodium bicarbonate and 1.95 mg/ml BCA (4,4'-dicarboxy-2,2'-biquinoline disodium salt (Sigma Chemical cat #D-8284). Added above to dH2O.
3. Prepare solution B by combining 1.24 mg/ml cupric sulfate pentahydrate and 1.26 mg/ml L-serine. Add mixture to dH2O.
4. Prepare a working reagent of a 1:1 ration of solutions A and B.
5. Prepare a Maltose standard solution of 10 mM Maltose in dH2O, where the 10 mM maltose is combined in 2% soluble starch at desired pH to a final concentration of 0, 100, 200, 300, 400, 600 µM. The standard curve will be generated for each set of time-points. Since the curve is determined by adding 10 ul of the standards to the working reagent it works out to 0, 1, 2, 3, 4, 6 nmole maltose. See FIG. 5 for an example standard curve.

6. Aliquot 1 ml of substrate solution into microcentrifuge tubes, equilibrate to desired temperature (5 min) in heat block or heated water bath. Add 50 ul of enzyme solution to the inside of the tube lid.

7. While solution is equilibrating mix 5 ml of both solution A & B. Aliquot 100 ul to 96 well PCR plate. Set plate on ice.

8. After 5 minute temperature equilibration, close lid on tubes, invert and vortex 3 times. Immediately aliquot 10 ul into plate as t=0 (zero time point). Leave enzyme mixture in heat block and aliquot 10 ul at each desired time point (e.g. 0, 5, 10, 15, 20, 30 minutes).

9. Ensure that 12 wells are left empty (only working reagent aliquotted) for the addition of 10 ul of standards, for the standard curve.

10. When all time points are collected and standards are added, cover plate and heated to 80° C. for 35 min. Cool plate on ice for 10 min. Add 100 ul H2O to all wells. Mix and aliquot 100 ul into flat bottomed 96-well plate and read absorbance at 560 nm.

11. Zero each sample's time points against its own t=0 (subtract the average t=0 A560 value from other average A560 values). Convert the $A560_{(experimental)}$ to umole (Divide $A560_{(experimental)}$ by the slope of the standard curve (A560/umole). Generate a slope of the time points and the umole (in umole/min), multiply by 100 (as the umole value only accounts for the 10 ul used in the assay, not the amount made in the 1 ml rxn). To get the specific activity divide the slope (in umole/min) by the mg of protein. All points should be done at a minimum in duplicate with three being best.

Activity=0.008646 umole/min

Divide protein concentration (mg/ml) by any dilution to get mg used in assay.

Divide the above slope by mg used in assay to get specific activity

Specific Activity =24.93 umole/min/mg

See for example, Dominic W. S. Wong, Sarah B. Batt, and George H. Robertson (2000) J. Agric. Food Chem. 48:4540-4543; Jeffrey D. Fox and John F. Robyt, (1991) Anal. Biochem. 195, 93-96.

Example 4: Screening for α-Amylase Activity

The following example describes an exemplary method for determining if a polypeptide is within the scope of the invention. Amylase activity of clones can be assessed by a number of methods known in the art. The following is the general methodology that was used in the present invention. The number of plaques screened, per plate, should be approximately 10,000 pfu's. For each DNA library: at least 50,000 plaques per isolated library and 200,000 plaques per non-isolated library should be screened depending upon the pfu titer for the λ Zap Express amplified lysate.

Titer Determination of Lambda Library

1) μL of Lambda Zap Express amplified library stock added to 600 μL E. coli MRF' cells ($OD_{600}$=1.0). To dilute MRF' stock, 10 mM MgSO4 is used.
2) Incubate at 37° C. for 15 minutes.
3) Transfer suspension to 5-6 mL of NZY top agar at 50° C. and gently mix.
4) Immediately pour agar solution onto large (150 mm) NZY media plate.
5) Allow top agar to solidify completely (approximately 30 minutes), then invert plate.
6) Incubate the plate at 39° C. for 8-12 hours.
7) Number of plaques is approximated. Phage titer determined to give 10,000 pfu/plate. Dilute an aliquot of Library phage with SM buffer if needed.

Substrate Screening

1) Lambda Zap Express (50,000 pfu) from amplified library added to 600 μL of E. coli MRF' cells (OD600=1.0). For non-environment libraries, prepare 4 tubes (50,000 pfu per tube).
2) Incubate at 37° C. for 15 minutes.
3) While phage/cell suspension are incubating, 1.0 mL of red starch substrate (1.2% w/v) is added to 6.0 mL NZY top agar at 50° C. and mixed thoroughly. Keep solution at 50° C. until needed.
4) Transfer ⅕ (10,000 pfu) of the cell suspension to substrate/top agar solution and gently mixed.
5) Solution is immediately poured onto large (150 mm) NZY media plate.
6) Allow top agar to solidify completely (approximately 30 minutes), then invert plate.
7) Repeat procedures 4-6 4 times for the rest of the cell suspension (⅕ of the suspension each time).
8) Incubate plates at 39° C. for 8-12 hours.
9) Plate observed for clearing zones (halos) around plaques.
10) Plaques with halos are cored out of agar and transferred to a sterile micro tube. A large bore 200 μL pipette tip works well to remove (core) the agar plug containing the desired plaque.
11) Phages are re-suspended in 500 μL SM buffer. 20 μL Chloroform is added to inhibit any further cell growth.
12) Pure phage suspension is incubated at room temperature for 4 hours or overnight before next step.

Isolation of Pure Clones 1) 10 μL of re-suspended phage suspension is added to 500 μL of E. coli MRF' cells (OD600=1.0).
2) Incubate at 37° C. for 15 minutes.
3) While phage/cell suspension is incubating, 1 mL of red starch substrate (1.2% w/v) is added to 6.0 mL NZY top agar at 50° C. and mixed thoroughly. Keep solution at 50° C. until needed.
4) Cell suspension is transferred to substrate/top agar solution and gently mixed.
5) Solution is immediately poured onto large (150 mm) NZY media plate.
6) Allow top agar to solidify completely (approximately 30 minutes), then invert plate.
7) Plate incubated at 39° C. for 8-12 hours.
8) Plate observed for a clearing zone (halo) around a single plaque (pure clone). If a single plaque cannot be isolated, adjust titer and re-plate phage suspension.
9) Single plaque with halo is cored out of agar and transferred to a sterile micro tube. A large bore 200 μL pipette tip works well to remove (core) the agar plug containing the desired plaque. To amplify the titer, core 5 single active plaques into a micro tube.
10) Phages are re-suspended in 500 μL SM buffer. 20 μL Chloroform is added to inhibit any further cell growth.
11) Pure phage suspension is incubated at room temperature for 4 hours or overnight before next step. The pure phage suspension is stored at −80° C. by adding DMSO into the phage suspension (7% v/v).

Excision of Pure Clone 1) 100 μL of pure phage suspension is added to 2004, E. coli MRF' cells (OD600=1.0). To this, 1.04, of ExAssist helper phage (>1×106 pfu/mL; Stratagene) is added. Use 2059 Falcon tube for excision.
2) Suspension is incubated at 37° C. for 15 minutes.
3) 3.0 mL of 2×YT media is added to cell suspension.

4) Incubate at 30° C. for at least 6 hours or overnight while shaking.
5) Tube transferred to 70° C. for 20 minutes. The phagemid suspension can be stored at 4° C. for 1 to 2 months.
6) 100 µL of phagemid suspension transferred to a micro tube containing 200 µL of *E. coli* Exp 505 cells (OD600=1.0).
7) Suspension incubated at 37° C. for 15 minutes.
8) 300 µL of SOB is added to the suspension.
9) Suspension is incubated at 37° C. for 30 to 45 minutes.
10) 100 µL of suspension is transferred to a small (90 mm) LB media plate containing Kanamycin (LB media with Kanamycin 50 µg/mL) for Zap Express DNA libraries or Ampicillin (LB media with Kanamycin 100 µg/mL) for Zap II DNA libraries.
11) The rest of suspension is transferred to another small LB media plate.
12) Use sterile glass beads to evenly distribute suspension on the plate.
13) Plates are incubated at 30° C. for 12 to 24 hours.
14) Plate observed for colonies.
15) Inoculate single colony into LB liquid media containing suitable antibiotic and incubate at 30° C. for 12 to 24 hours.
16) Glycerol stock can be prepared by adding 80% glycerol into liquid culture (15% v/v) and stored at −80° C.

Activity Verification
1) 50 µL of liquid culture is transferred to a micro tube. Add 500 µL of 8% pH7 Amylopectin Azure into the same tube. Prepare 2 tubes for each clone.
2) Activity is tested at 50° C. for 3 hours and overnight. Use pH 7 buffer as control.
3) Cool the test specimen at ice-water bath for 5 minutes.
4) Add 750 µL of Ethaqnol and mixed thoroughly.
5) Centrifuge at 13000 rpm (16000 g's) for 5 minutes.
6) Measure OD of the supernatant at 595 nm.

RFLP Analysis
1) 1.0 mL of liquid culture is transferred to a sterile micro tube.
2) Centrifuge at 13200 rpm (16000 g's) for 1 minute.
3) Discard the supernatant. Add another 1.0 mL of liquid culture into the same sterile micro tube.
4) Centrifuge at 13200 rpm (16000 g's) for 1 minute.
5) Discard the supernatant.
6) Follow QlAprep spin mini kit protocol for plasmid isolation.
7) Check DNA concentration using BioPhotometer.
8) Use Sac I and Kpn I for first double digestion. Incubate at 37° C. for 1 hour.
9) Use Pst I and Xho I for second double digestion. Incubate at 37° C. for 1 hour.
10) Add Loading dye into the digested sample.
11) Run the digested sample on a 1.0% agarose gel for 1-1.5 hours at 120 volts.
12) View gel with gel imager. All clones with a different digest pattern will be sent for sequence analysis.

Example 5: Assays for Amylases

The following example describes an exemplary assays for determining if a polypeptide is within the scope of the invention.

Preparation of Host Cultures
1. Start an overnight culture of XL1-Blue MRF' host cells. Use a single colony from a streak plate to inoculate 10 mL LB supplemented with 20 ug/mL tetracycline. Grow overnight culture shaking at 37° C. for at least 16 hours.
2. Using aseptic technique, inoculate a fresh 100 mL of Lard day culture with XL1-Blue MRF' host from the overnight LBTet culture.
3. Grow in a 37° C. shaker until the OD reaches 0.75-1.0.
4. Pellet host cells at 1000×g for 10 minutes and gently resuspend in 10 mM MgSO$_4$ at OD5.
5. Dilute a small amount of host cells to OD1 for use in titering and pintooling.
6. Host preparations can be used for up to 1 week when stored on ice or at 4° C.
   To shorten growth time for the day culture, use ½× the usual Tet concentration in LB (½×=10 ug/mL), or omit the antibiotic altogether.
   Do not use NZY when selecting with Tetracycline. The high Mg$^{++}$ concentration in NZY medium renders Tet inactive.

Titering Lambda Libraries
7. Place three sterile microfuge tubes in a rack.
8. Aliquot 995 uL prepared host cells in one tube and 45 uL prepared OD1 host cells into each of the two remaining tubes.
9. Add 5 uL of lambda library to the tube containing 995 uL host cells and mix by vortexing. This results in a dilution factor of 200.
10. Prepare 1/2,000 and 1/20,000 dilutions by consecutively adding 5 uL of previous dilution to the remaining two tubes containing 45 uL prepared host cells. Mix by vortexing after each dilution was made.
11. Allow phage to adsorb to host by incubating at 37° C. for 15 minutes.
12. Meanwhile, pipet 100 uL of prepared OD1 host cells to each of three Falcon 2059 tubes.
13. Add 5 uL of each dilution to a separate 2059 tube containing host cells.
14. Plate each by adding 3 mL top agar to each tube and quickly pour over 90 mm NZY plates. Ensure a smooth, even distribution before the top agar hardens.
15. Invert plates and incubate at 37° C. overnight.
16. Count plaques and calculate titer of the library stock (in plaque forming units (pfu) per uL).

Lambda Microtiter Screening for Amylases
Preparation
1. Prepare a sufficient amount of XL1-Blue MRF' host culture, as described above, for the amount of screening planned. A culture of 100 mL is usually sufficient for screening 2-3 libraries.
2. Autoclave several bottles compatible with the QFill2 dispenser. These are the wide-mouth Corning bottles, 250 mL containing a sealing ring around the lip.
3. Make sure there are sufficient amounts of plates, top agar, BODIPY starch, red starch solution, etc. available for the screen.
4. Schedule the Day 2 robot run with a representative from Automation.

Day 1
1. Label the 1536-well plates (black) with library screen and plate number. Tough-Tags™ tube stickers, cut in half width-wise, are ideal for labeling 1536 well plates.
2. Calculate volumes of library, host cells and NZY medium necessary for the screen. This is easily done with an Excel spreadsheet.
3. Combine the calculated volumes of lambda library and OD5 host cells in a sterile 250 mL wide-mouth Corning bottle (containing a sealing ring).

4. Allow adsorption to occur at 37° C. for 15 minutes.
5. Add the calculated volume of NZY medium and mix well. This is referred to as the cell-phage-medium suspension.
6. Perform a concomitant titer by combining 50 uL of the cell-phage-medium suspension with 250 uL of OD1 host cells in a Falcon 2059 tube, then plating with 9 mL of top agar onto a 150 mm NZY plate. Incubate concomitant titer plate at 37° C. overnight.
7. Load the dispenser with the remainder of the suspension and array each labeled 1536-well plate at 4 uL per well. If the dispenser leaves air bubbles in some wells, they can be removed by centrifuging the plates at 200×g for 1 minute.
8. Add 0.5 uL of positive control phage to well position AD46 of at least two of the assay plates. Use a strong amylase-positive lambda clone for this purpose. The lambda versions of SEQ ID NO.: 113 or SEQ ID NO.: 199 are good choices for positive controls.
9. Incubate assay plates at 37° C. overnight in a humidified (>_95%) incubator.

Day 2
1. Count the pfu on the concomitant titer plate and determine the average seed density per well (in pfu per well).
2. Pintool at least 2 plates of each library screen (preferably the 2 containing positive controls) as follows:
   a) Prepare 2 host lawn plates to act as a surface on which to pintool: combine 250 uL of OD1 host cells with 2 mL 2% red starch and plate with 9 mL top agar onto 150 mm NZY plates. Hold each plate as level as possible as the top agar solidifies in order to produce an even hue of red across the plate.
   b) Using a twice flame-sterilized 1536 position pintool, replicate at least 2 of the screening plates onto the host lawn plates.
   c) Place the pintooled recipient plates in a laminar flow hood with the lids off for about 15-30 minutes (to vent off excess moisture).
   d) Replace the lids and incubate inverted at 37° C. overnight.
3. Prepare the 2×BODIPY starch substrate buffer as follows:
   a) Calculate the total volume of 2× substrate buffer solution needed for all screening plates at 4 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
4. Take plates and substrate buffer to the automation room and program the robot with the following parameters:
   a) dispense 4 uL substrate buffer per well
   b) $1^{st}$ read at 1 hour post-substrate, $2^{nd}$ read at 9 hours, and third read at 17 hours; with 37° C. incubation between reads
   c) excitation filter: 485 nm; emission filter: 535 nm
   d) set the Spectrafluor gain at 70, or the optimal gain for the batch of 2× substrate buffer prepared.
   e) ensure that the incubator used will protect assay plates from light.

Day 3
1. Check pintooled plates for clearings in the bacterial lawn at all positions corresponding to wells on the associated assay plate. Also check for clearings in the red starch in any of the pin positions. If plates containing positive controls were used for pintooling, you should be able to see a large clearing zone in the red background. Be wary of contaminants that also form clearing zones in red starch (see comment "Contaminants That Form Clearing Zones in Red Starch" at end of Example).
2. Identify putative hits from the data file produced by the robot computer. The KANAL program produced by Engineering simplifies data analysis. As a rule of thumb, a putative hit is characterized as a well having signal intensity rising at least 1.5 fold over background.
3. For each putative, remove 2 uL from the well and add to a tube containing 500 uL SM buffer and 50 uL CHCl3. Vortex to mix and store at 4° C. This solution will be referred to hereafter as the 4e–3 stock. The original screening plates should be stored at 4° C., protected from light, at least until breakouts are complete.

This is a recommended method of breaking out putative hits. It is a liquid phase assay that relies on confirmation of activity on BODIPY starch. Alternatively, putative hits can be plated directly onto solid phase plates containing red starch such that 2,000-3,000 pfu per hit are examined for clearing zones. However, inability to observe clearing zones on red starch is not necessarily an indication that a putative hit was a false positive. It would then need to be assayed using the format in which it was originally identified (i.e., liquid phase using BODIPY starch as substrate). In addition, very weak positives are more easily identified using the method detailed below.

Day 1
1. In a sterile 50 mL conical tube, combine 0.5 mL OD5 host cells with 45.5 mL NZY. This will be referred to as the host-medium suspension.
2. For each putative hit to be analyzed, aliquot 1 mL of host-medium suspension into each of 3 three sterile microfuge tubes.
3. Set the 12-channel pipetman in multidispense mode with an aliquot size of 20 uL and an aliquot number of 2×. Mount the pipetman with a clean set of sterile tips.
4. Pour about 1 mL of host-medium suspension into a new sterile solution basin and load the multichannel pipetman.
5. Dispense 20 uL per well into the last row (row P) of a black 384-well plate (12 channels×2=24 wells). This row will be used later for the controls.
6. Expel the remaining liquid in the tips by touching the tips against the surface of the basin and pressing the RESET button on the pipetman. Lay the pipetman down in a way to prevent contamination of the tips. There is no need to change the tips at this point.

7. Pour the remainder of the fluid in the basin into a waste container (like a beaker) taking care to avoid splashback contamination.
8. For the first putative to be analyzed, take 111 uL of the 4e−3 stock (see Day 2 in Lambda Microtiter Screening for Amylases) and add it to the first in a set of three tubes containing 1 mL host-medium suspension (step 2). Vortex to mix. This is Dilution A.
9. Take 111 uL of Dilution A and add to the next tube in the set. Vortex to mix. This is Dilution B.
10. Take 111 uL of Dilution B and add to the last tube in the set. Vortex to mix. This is Dilution C. You should now have three dilutions of phage, where concentrations of each differ by a factor of 10.
11. Pour the contents of Dilution C (the most dilute of the 3 samples) into the solution basin and load the multichannel pipetman.
12. Dispense 20 uL per well into the first row of the 384-well plate (12 channels×2=24 wells).
13. Expel the remaining liquid in the tips by touching the tips against the surface of the basin and pressing the RESET button on the pipetman. Lay the pipetman down in a way to prevent contamination of the tips. There is no need to change the tips at this point.
14. Empty the basin as described above.
15. Pour the contents of Dilution B into the same basin and load the multichannel pipetman.
16. Dispense 20 uL per well into the second row of the 384-well plate.
17. Perform steps 13-16 similarly to dispense Dilution A into the third row of the plate.
18. After all three dilutions have been arrayed into the first 3 rows of the plate, discard all tips and the solution basin into the biohazardous waste container.
19. Mount the pipetman with a clean set of sterile tips and open a new sterile solution basin.
20. Repeat steps 8-19 for each remaining putative hit, using remaining rows on the plate up to row O. Five putative hits can be analyzed on one 384-well plate, with the last row (row P) saved for the controls.
21. Add 0.5 uL of each control to a separate well. Use at least 2-3 separate controls, preferably covering a range of activity.
22. Incubate assay plates at 37° C. overnight in a humidified (95%) incubator.

Day 2
1. Pintool all breakout plates onto a host lawn with red starch using the same method described for Day 2 in Lambda Microtiter Screening for Amylases, except that a 384 position pintool is used.
2. Prepare the 2× BODIPY starch substrate buffer as follows:
   a) Calculate the total volume of 2× substrate buffer solution needed for all breakout plates at 20 uL per well (including any extra deadspace volume required by the dispenser) and measure this amount of 100 mM CAPS pH 10.4 into a vessel appropriate for the dispenser used.
   b) Retrieve enough 0.5 mg tubes of BODIPY starch to produce the required volume of 2× substrate buffer [calculated in step a) above] at a final concentration of 20-30 ug/mL.
   c) Dissolve each 0.5 mg tube in 50 uL DMSO at room temperature, protected from light, with frequent vortexing. This takes more than 15 minutes; some production lots of BODIPY starch dissolve better than others.
   d) Add 50 uL 100 mM CAPS buffer pH 10.4 to each tube and mix by vortexing.
   e) Pool the contents of all tubes and remove any undissolved aggregates by centrifuging for 1 minute at maximum speed in a microfuge.
   f) Add the supernatant to the rest of the 100 mM CAPS buffer measured in step a) above.
   g) Protect the 2× substrate buffer from light by wrapping in foil.
3. Dispense 20 uL per well into all breakout plates.
4. Wrap all plates in aluminum foil and incubate at room temperature for 2-6 hours.
5. Read each plate in the Spectrafluor with the following settings:
   a) fluorescence read (excitation filter: 485 nm; emission filter: 535 nm)
   b) plate definition: 384 well black
   c) read from the top
   d) optimal gain
   e) number of flashes: 3
6. On the resulting Excel spreadsheet, chart each putative's 3 rows in a separate graph and check for activity. Ensure that the positives controls produced signals over background.
7. For each putative that appears to have a real signal among the wells, harvest a sample from a positive well as follows:
   a) Select a positive well from a row representing the highest initial dilution.
   b) Transfer 2 uL from that well into a tube containing 500 uL SM and 50 uL $CHCl_3$. This is referred to as the breakout stock.
   c) Store at 4° C.
8. Using methods previously described, plate about 10 uL of each breakout stock onto 150 mm NZY plates using red starch. The objective is to obtain several (at least 20) well-separated plaques from which to core isolates.

Day 3
1. Check pintooled plates for an acceptable incidence of clearings in the bacterial lawn corresponding to wells on the associated assay plate. Also check for clearings in the red starch in the positive controls and in any tested putatives. Be wary of contaminants that also form clearing zones in red starch (see below).
2. From the solid phase plates containing dilutions of breakout stocks, core several isolated plaques, each into 500 uL SM with 50 uL $CHCl_3$. This is referred to as the isolate stock.
3. The isolate stocks can then be individually tested on BODIPY starch using methods described above. This step can be skipped if the plaque that was cored in step 2 produced a clearing zone in the red starch background. The isolate stocks were then be individually tested on BODIPY starch using methods described above. However, this step may be skipped if the plaque that was cored in step 2 produced a clearing zone in the red starch background.

Excisions
Day 1
1. In a Falcon 2059 tube, mix 200 uL OD1 XL1-Blue MRF' host, 100 uL lambda isolate stock and 1 uL ExAssist phage stock.
2. Incubate in 37° C. shaker for 15 minutes.
3. Add 3 mL NZY medium.
4. Incubate in 30° C. shaker overnight.

Day 2
1. Heat to excision tube to 70° C. for 20 minutes.
2. Centrifuge 1000×g for 10 minutes.
3. In a Falcon 2059 tube, combine 50 uL supernatant with 200 uL EXP505 OD1 host.
4. Incubate in 37° C. shaker for 15 minutes.
5. Add 300 uL SOB medium.
6. Incubate in 37° C. shaker for 30-45 minutes.
7. Plate 50 uL on large $LB_{Kan50}$ plate using sterile glass beads. If the plates are "dry", extra SOB medium can be added to help disburse the cells.
8. Incubate plate at 30° C. for at least 24 hours.
9. Culture an isolate for sequencing and/or RFLP.

Growth at 30° C. reduces plasmid copy number and is used to mitigate the apparent toxicity of some amylase clones.

Contaminants that Form Clearing Zones in Red Starch

When using red starch on solid medium to assay phage for amylase activity, it is common to see contaminating colony forming units (cfu) that form clearing zones in the red starch. For pintooled plates, it is important to distinguish amylase-positive phage clones from these contaminants whenever they align with a particular well position. The source of the contaminating microbes is presumably the 2% red starch stock solution, which cannot be sterilized by autoclaving or by filtering after preparation. It is thought that they are opportunistic organisms that survive by metabolizing the red starch. In order to reduce these contaminants, use sterile technique when making 2% red starch solutions and store the stocks either at 4° C. or on ice.

Screening of α-Amylases

Primary screening can be done using RBB-starch and/or FITC-starch as substrates. Elevated active clones can be screened using RBB-starch as substrate using induced cultures and by liquefaction assay. Stock and sequencing new elevated active clones based on liquefaction data can be performed.

The amylases can be sorted into 96-well plates (or 384-well plates) at 1 cell/well in 50 µl of LB+Tet. The plates can be incubated for 24 hours at 30° C. Replicate plates can be made corresponding to each well for storage. Forty-five (45) ⊠l of 12M urea is added to each well and the plates shaken for 10 minutes. Plates can be kept at room temp for at least 1 hour and the lysate stored at 4° C.

Assay Using RBB-Starch

75 µl of RBB-starch substrate (1% RBB-insoluble corn starch in 50 mM NaAc buffer, pH=4.5) can be added into each well of a new 96-well plate (V-bottom). Five microliters of enzyme lysate can be transferred into each well with substrate using Biomek or Zymark. The plates can be sealed with aluminum sealing tape and shaken briefly on the shaker. The plates can be incubated at 90° C. for 30 minutes, followed by cooling at room temperature for about 5 to 10 minutes. One hundred micro-liters of 100% ethanol can be added to each well, the plates sealed and shaken briefly on the shaker. The plates can be then centrifuged 4000 rpm for 20 minutes using bench-top centrifuge. 100 µl of the supernatant can be transferred into a new 96-well plate (flat bottom) by Biomek and read $OD_{595}$.

Assay Using FITC-Starch

50 µl of substrate (0.01% FITC-starch in 100 mM NaAc buffer, pH=4.5) can be added into each well of a new 384-well plate. 5 µl of enzyme lysate can be transferred into each well with substrate and incubated the plate at room temperature overnight. The polarization change of the substrate, excitation 485 nm, emission 535 nm can be read for each well. 96 well plates can be used for all assays.

Confirmation of New Active Clones

Each positive clone from screening can be grown and induced using a standard protocol. Each clone can be examined for growth (i.e., cell density over time), activity at per cell level (RBB-starch assay and liquefaction assay), expression (protein gel) and solubility of protein (by microscope analysis). The confirmed new elevated clones can be transferred for fermentation. One of the clones have amylase activity greater than that of the parent includes the enzyme set forth in SEQ ID NO:2 (encoded by SEQ ID NO:1).

Example 6: Characterization of Alpha Amylase pH Optimum and Specific Activity Determination The following example describes an exemplary method for determining if a polypeptide is within the scope of the invention, e.g., by alpha amylase activity pH optimum and specific activity determination.

The pH optimum for the hydrolysis of starch can be determined by reacting 50 uL of the GP-1, 0.35 U/ml, with a 100 ml of 1% soluble starch solution (0.0175 U/g of starch) for 30 minutes at 95° C. The reducing ends generated in the liquefied starch solution can be measured by the neocupronine assay, described herein. The percent hydrolysis of cornstarch can be determined by measuring the number of sugar reducing ends produced with the neocupronine assay. Seventy grams of buffer solution (pH 4-7) is weighed and 100 ppm of calcium added. Thirty grams of cornstarch is mixed into the buffer solution to form a starch slurry. The enzyme can be added and the vessels sealed and incubated at 95° C. for 30 minutes with an initial heating rate of 6° C. per minute. A 1 ml sample can be extracted from the reaction beakers and analyzed by the neocupronine assay.

Example 7: Exemplary Protocol for Liquefying Starch and Measuring Results

The following example describes exemplary protocols for liquefying starch using amylases of the invention.

Reaction Conditions: 100 mM $PO_4$ pH 6.5, 1% (w/w) liquefied starch DE 12 at 55° C. Both TLC and HPLC assays were done to verify activity. The data from both assays showed that the clones were active.

pH profiles for the amylases can be run using phosphate buffer pHed from 3.0-6.5, at 55° C. From the amount of observable hydrolysis, it can be visually said that the clones were more active at certain pH values than at other values at the above indicated reaction conditions:

An exemplary protocol for the saccharification of liquefied starch at pH 6.5:
  Adjust the pH of the liquefied starch to the pH at which the saccharification(s) will be performed. Liquefy starch in 100 mM sodium acetate buffer, pH 4.5 with 100 mM sodium phosphate salts added so that before saccharification, the pH could be adjusted to pH 6.5.
  Weigh 5 gram samples of liquefied starch into tared bottles.
  Use 0.04% (w/w) Optidex L-400 or approximately 400 mL of 1-10 diluted stock Optidex L-400 per 100 grams of liquefied starch.
  Calculate the milligrams of Optidex L-400 contained in the 400 mL of 1-10 diluted stock Optidex L-400. Next, calculate the volume of lysates needed to give the same concentration of enzyme as the Optidex L-400.

Add enzymes to liquefied starch samples and incubate at desired temperature (50 C.°). After 18 hours determine DE and prepare a sample for HPLC analysis.

An exemplary DE Determination:

Exemplary Neocuproine Assay:

A 100 ml sample can be added to 2.0 ml of neocuproine solution A (40 g/L sodium carbonate, 16 g/L glycine, 0.45 g/L copper sulfate). To this can be added 2.0 ml of neocuproine solution B (1.2 g/L neocuproine hydrochloride-Sigma N-1626). The tubes can be mixed and heated in a boiling water bath for 12 minutes; cooled, diluted to 10 ml volume with DI water and the OD read at 450 nm on the spectrophotometer. The glucose equivalent in the sample can be extrapolated from the response of a 0.2 mg/ml glucose standard run simultaneously.

Exemplary HPLC Analysis:

Saccharification carbohydrate profiles are measured by HPLC (Bio-Rad Aminex HPX-87A column in silver form, 80° C.) using refractive index detection. Mobile phase is filtered Millipore water used at a flow rate of 0.7 ml/min. Saccharification samples are diluted 1-10 with acidified DI water (5 drops of 6 M HCl into 200 mL DI water) then filtered through a 0.45 mm syringe filter. Injection volume is 20 uL.

Exemplary TLC:

Reaction products can be w/d at hourly timepoints and spotted and dried on a TLC plate. Plates can be developed in 10:90 water:isopropanol and visualized with either a vanillin stain or CAM stain and then heated to show reducible sugars. The liquefied starch can be partially hydrolyzed to glucose in cases where activity is observed.

Example 8: Starch Liquefaction Using Amylases of the Invention

This example describes an exemplary method of the invention for liquefying starch using amylases of the invention.

Amylase concentrate can be prepared from fermentation broths by heat treatment, cell washing, alkaline extraction using microfiltration and ultrafiltration (48% overall yield). The UF concentrate can be neutralized with acetic acid and formulated with 30% glycerol at pH 4.5. The activity level of the slurry formulation can be representative of a commercial product (120 U$^1$/g–0.5 kg/ton starch).

Standard Amylase Activity Assay

A 1 mL cuvette containing 950 µL of 50 mM MOPS pH 7.0 containing 5 mM pNP-α-D-hexa-(1→4)-glucopyranoside can be placed in the Peltier temperature controller of the Beckman DU-7400 spectrophotometer preheated to 80° C. The spectrophotometer is blanked at 405 nm and 50 µL of the enzyme solution is added to the cuvette, mixed well and the increase in the $OD_{405\ nm}$ was monitored over a one-minute interval. The $\Delta OD_{405\ nm/min}$ rate is converted to a standard unit of µmole/minute from the $OD_{405\ nm}$ response of 50 µL of 1 µmole/mL PNP in 950 mL 50 mM MOPS at pH 7.0-80° C. One standard unit of thermostable alpha amylase (DTAA) is equal to the amount of enzyme that will catalyze the release of 1 µmole/mL/minute of pNP under the defined conditions of the assay.

Standard Glucoamylase Activity Assay

A 1 mL cuvette containing 950 µL of 50 mM MOPS pH 7.0 containing 5 mM pNP-α-D-glucopyranoside can be placed in the Peltier temperature controller of the Beckman DU-7400 spectrophotometer preheated to 60° C. The spectrophotometer can be blanked at 405 nm and 50 µL of the enzyme solution is added to the cuvette, mixed well and the increase in the $OD_{405\ nm}$ was monitored over a one-minute interval. The $\Delta OD_{405\ nm}$/min rate is converted to a standard unit of µmole/minute from the $OD_{405\ nm}$ response of 50 µL of 1 µmole/mL pNP in 950 mL 50 mM MOPS at pH 7.0-60° C. One standard unit of glucoamylase (DGA) is equal to the amount of enzyme that will catalyze the release of 1 µmole/mL/minute of pNP under the defined conditions of the assay.

Dextrose Equivalent Determination

The neocuproine method was used to measure the DE. Selected samples were measured by both the Invention procedure and by a GPC analyst using the GPC Fehlings procedure.

Neocuproine Assay

A 100 µl sample can be added to 2.0 ml of neocuproine solution A (40 g/L sodium carbonate, 16 g/L glycine, 0.45 g/L copper sulfate). To this is added 2.0 ml of neocuproine solution B (1.2 g/L neocuproine hydrochloride-Sigma N-1626). The tubes can be mixed and heated in a boiling water bath for 12 minutes; cooled, diluted to 10 ml volume with DI water and the OD read at 450 nm on the spectrophotometer. The glucose equivalent in the sample can be extrapolated from the response of a 0.2 mg/ml glucose standard run simultaneously.

The starch sample is diluted ~1 to 16 with DI water with the exact dilution recorded. Ten milliliters of the diluted sample was added to 20 mls of DI water. Ten milliliters of Fehlings solution A and B can be added to the diluted starch. The sample can be boiled for 3 minutes and cooled on ice. Ten milliliters of 30% KI and 10 ml of 6N $H_2SO_4$ is added. The solution is titrated against 0.1N sodium thiosulfate. The titrant volume is recorded and used to calculate the DE.

Residual Starch Determination

Post-saccharification samples can be checked for residual starch using the Staley iodine procedure.

Twenty grams of sample can be weighed into a large weigh dish. 45 µL of Iodine solution is added to the weigh dish and the starch solution is mixed well. Dark blue indicates the presence of starch, a light blue-green indicates slight starch, light green indicates a trace of starch and yellow-red, absence of starch. Iodine solution is prepared by dissolving 21.25 grams of iodine and 40.0 grams of potassium iodide in one liter of water.

Oligosaccharide Profile

Liquefaction and saccharification carbohydrate profiles can be measured by HPLC (Bio-Rad Aminex HPX-87C column in calcium form –80° C.) using refractive index detection.

Gel Permeation Chromatography

The molecular weight distribution can be determined by chromatography on a PL Aquagel-OH column with mass detection by refractive index (Waters Model 2410). A Viscotek Model T60 detector can be used for continuous viscosity and light scattering measurements.

Capillary Electrophoresis

Beckman Coulter P/ACE MDQ Glycoprotein System—separation of APTS derivatized oligosaccharides on a fused silica capillary—detection by laser-induced fluorescence.

Primary Liquefaction

Line starch directly from the GPC process is pumped into a 60 liter feed tank where pH, DS (dry solids) and calcium level can be adjusted before liquefaction. The amylase is added to the slurry. The 32% DS slurry is pumped at 0.7 liter/minute by a positive displacement pump to the jet—a pressurized mixing chamber where the starch slurry is instantaneously heated to greater than 100° C. by steam injection. The gelatinized partially liquefied starch is pumped through a network of piping (still under pressure) to give the desired dwell time (5 minutes) at temperature. The pressure is released into a flash tank and samples can be taken. Samples are taken in duplicate.

Secondary Liquefaction

The liquefied starch can be collected in one liter glass bottles and held in a water bath at 95° C. for 90 minutes.

Saccharification

Liquefied starch can be cooled to 60° C., the pH adjusted to 4.5 and the samples treated with glucoamylase. Saccharification progress can be monitored over time by HPLC.

Preparation of Liquefied Syrups for Analysis

These trials were run to obtain liquefied syrups at DE's of ~12 and 18 for three amylases; SEQ ID NO: 6, SEQ ID NO: 2, commercial B. licheniformis amylase. The syrups were saccharified with three levels of glucoamylase. The liquefied syrups were also analyzed by HPLC and gel permeation chromatography.

Saccharification

The liquefied syrups produced with each amylase can be adjusted to approximately pH 2.5 with 6N HCl immediately after the 90 minute secondary liquefaction to inactivate any residual amylase. The syrups can be then adjusted to pH 4.5, placed in a 60° C. water bath and saccharified with three levels of glucoamylase. The extent of saccharification can be monitored by HPLC at 18 to 88 hour time points.

The liquefied syrups can be saccharified with the standard dosage—0.04% of a double-strength glucoamylase—and two lower dosages (50% and 25%) to monitor any differences in the saccharification progress. Saccharification Progress—% dextrose development vs time—0.04% glucoamylase.

The liquefied syrups were saccharified with the standard dosage—0.04% of a double-strength glucoamylase—and two lower dosages (50% and 25%) to monitor any differences in the saccharification progress. The glucose levels are higher at earlier time points with the SEQ ID NO:2 syrups. Some of the difference is due to a higher starting point but the molecular weight profile difference is also a contributing factor (the oligosaccharides in the SEQ ID NO:2 liquefied syrups—being smaller and more uniform—should be, and apparently are, better substrates for glucoamylase).

Saccharification Progress—% dextrose development vs time—0.04% glucoamylase

| Amylase | 18 hr | 24 hr | 40 hr | 44 hr | 88 hr |
|---|---|---|---|---|---|
| Commercial | 70.2 | 78.4 | 86.1 | 86.7 | 94.2 |
| SEQ ID NO: 2 | 79 | 88.6 | 92.5 | 92.8 | 95.3 |
| SEQ ID NO: 6 | 74.1 | 85.9 | 91.9 | 91.6 | 94.8 |

Saccharification Progress—% dextrose development vs time—0.02% glucoamylase

| Amylase | 18 hr | 24 hr | 40 hr | 44 hr | 88 hr |
|---|---|---|---|---|---|
| B. licheniformis Amylase | 54.5 | 66.7 | 76.1 | 77.2 | 90.9 |
| SEQ ID NO: 2 | 60.1 | 72 | 84.8 | 85.3 | 93.6 |
| SEQ ID NO: 6 | 57.1 | 70 | 84 | 86.5 | 92.5 |

Post-Saccharification Sugar Profile

In these studies and all previous saccharification studies, the final glucose level achieved after saccharification of Invention amylase and B. licheniformis liquefied syrups is essentially identical. The DP2 (maltose) level is also similar. These large fragments are poor substrates for glucoamylase and tend to be converted slowly, if at all, into smaller fragments and ultimately, glucose).

|  | Glucose | DP2 | DP3 | >DP7 |
|---|---|---|---|---|
| SEQ ID NO: 2 | 95.25 | 2.39 | 1.13 | 0.91 |
| Commercial | 94.16 | 2.10 | 0.39 | 2.91 |
| SEQ ID NO: 6 | 94.77 | 2.27 | 1.48 | 0.82 |

Molecular Weight Distribution

The molecular weight distribution of syrups liquefied to DE's of 12 and 18 by the invention's amylase SEQ ID NO:2, and SEQ ID NO:6, and commercial Bacillus licheniformis and commercial Bacillus stearothermophilus) were measured by gel permeation chromatography using detection by refractive index, light scattering and viscosity. Both the licheniformis and stearothermophilus amylases generate a bimodal distribution—the primary peak centered at 2000, a secondary peak at 32,000 with a shoulder extending past the 160,000 range. The lower molecular weight peak represents approximately 60% of the total mass of the sample. The invention amylases exhibit a single peak at 2000 with very little above 30,000.

HPLC

The DE 12 and 18 syrups produced by the Invention and commercial amylases were analyzed by HPLC. Both techniques (chromatograms/electropherograms) produce fingerprints characteristic of each class of amylase; the oligosaccharide patterns are different for licheniformis vs stearothermophilus vs the invention's amylases. The invention's liquefied syrups exhibit evidence of greater branching in the oligosaccharides. HPLC only resolve the oligosaccharides in the <DP15 range—larger fragments are not visible in these techniques. Bacillus amylases are known to liquefy starch in a manner such that the amylopectin fraction is hydrolyzed less extensively than the amylose fraction. These >DP30 amylopectin fragments are contained in the high molecular weight fraction centered at 32,000 and consequently, little evidence of branching is seen in the HPLC analyses of the Bacillus liquefied syrups. The <DP15 oligosaccharides from Invention amylases contain fragments from both amylose and amylopectin.

This example characterizes the liquefaction oligosaccharide patterns resulting from the invention's enzyme SEQ ID NO:2 and SEQ ID NO:6 versus commercial Bacillus licheniformis and Bacillus stearothermophilus amylases. These results looked at the saccharification progress and final dextrose levels from syrups generated by invention and commercial amylases.

Three commercial enzymes, Genencor Spezyme AA, and two others all required more than double the recommended dosage to achieve the target Dextrose equivalent (DE). Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

This confirms the "double dosage" effect for all Bacillus amylases and gives more credence to the proposal that the observed dosage for SEQ ID NO:2 in the trials is also twice the value which would be required under more normal conditions. The projected "normal" dosage, 60-70 Units/kilo starch at pH 4.5 to reach a 19 DE, is consistent with the laboratory liquefaction data.

The oligosaccharide pattern generated by invention amylases is different from the *Bacillus* profiles. The molecular weight distribution for the *Bacillus* amylases (gel permeation chromatography with detection by light scattering and viscosity) is bimodal with a substantial fraction at the very high molecular weight range (>300,000) even at an 18DE. The SEQ ID NO:2 at 18DE exhibits a uniform distribution with nothing greater than 20,000. This is consistent with the lower viscosity for Invention syrups. The DP (degrees of polymerization) profiles as measured by HPLC also reflects this difference in action pattern.

In this study, as well as in the previous studies, the final glucose level after saccharification of Invention amylase liquefied syrups vs the *Bacillus* syrups is the same for both cases. However, we have now acquired sufficient saccharification data from internal as well as from the GPC studies to confirm that the non-dextrose residuals for the invention amylases are different from the *Bacillus* amylase syrups. Although the dextrose and maltose levels are essentially the same for both, the Invention amylases have a higher DP3 fraction but lower amount of the "highers" vs. the *Bacillus* enzyme. Consistent with the absence of high molecular weight fragments after liquefaction, the post saccharification Invention syrups have a lower content of the >DP7 fraction.

|  | Glucose | DP2 | DP3 | >DP7 |
|---|---|---|---|---|
| SEQ ID NO: 2 | 95.25 | 2.39 | 1.13 | 0.91 |
| Commercial | 94.16 | 2.10 | 0.39 | 2.91 |
| SEQ ID NO: 6 | 94.77 | 2.27 | 1.48 | 0.82 |

SEQ ID NO:2 amylase concentrate was prepared from fermentation broths by heat treatment, cell washing, alkaline extraction using microfiltration and ultraflitration (48% overall yield). The UF concentrate was neutralized with acetic acid and formulated with 30% glycerol at pH 4.5. The activity level of the slurry formulation was representative of a commercial product ($120U^1$/g-0.5 kg/ton starch).

Example 9: Starch Liquefaction at pH 4.5 Using Amylases of the Invention

The conversion of starch to glucose can be catalyzed by the sequence action of two enzymes: alpha-amylases of the invention to liquefy the starch (e.g., the hydrolysis of high molecular weight glucose polymers to oligosaccharides consisting of 2 to 20 glycose units, typically a dextrose equivalent of 10 to 12, by an amylase of the invention), followed by saccharification with a glycoamylase (which can be a glycoamylase of the invention). In one aspect, processing is in a corn wet milling plant producing a starch slurry having a pH or about 4.0 to 4.5. In one aspect, the pH is raised, e.g., to 5.8 to 6.0 before liquefaction to accommodate an alpha amylase with a low pH activity and stability (which can be an alpha amylase of the invention). In one aspect, amylases of the invention can liquefy starch at pH 4.5 to dextrose equivalents ranging from 12 to 18; in one aspect, using alpha amylases of the invention at levels of about 3 to 6 grams per ton of starch. In this aspect, use of alpha amylases of the invention enables starch liquefaction to be conducted at pH 4.5.

In one aspect, starch liquefaction is conducted at pH 4.5 for 5 minutes at 105° C. to 90 minutes at 95° C. using amylases of the invention. The quantity of enzyme was adjusted in order to adjust a target DE of 12 to 15 after liquefaction. In one aspect, the liquefied starch is then saccharified with a glucoamylase, e.g., an *Aspergillis* glucoamylase, for about 48 hours at about pH 4.5 and 60° C. If the saccharified syrup did not contain at least 95% glucose, the target liquefaction DE was raised and the saccharification repeated until the liquefaction eventually did produce a saccharified syrup containing more than 95% glucose. The amylase protein required to produce a suitable liquefied feedstock for saccharification was determined by PAGE.

Example 10: Amylase Ligation Reassembly

Nine fragments (each about 150 bp) were amplified from each of the parent clones SEQ ID NO: 6, SEQ ID NO: 66, SEQ ID NO: 67, covering the whole open reading frame. The primers are provided in Table 1.

TABLE 1

|  | SEQ ID NO: |  |
|---|---|---|
| GAACACTAGTAGGAGGTAACTTATGGCAAAGTATTCCGAGCTCGAAG | 11 | SpeI |
| GAACGGTCTCATTCCGCCAGCCAGCAAGGGGATGAGCGG | 12 | BsaI |
| GAACCGTCTCAAAACACGGCCCATGCCTACGGC | 13 | BsmBI |
| GAACGTCTCACCTCGACTTCCACCCCAACGAGGTCAAG | 14 | BsmAI |
| GAACGTCTCAGGCGCTTTGACTACGTGAAGGGC | 15 | BsmAI |
| GAACGGTCTCAACAAGATGGATGAGGCCTTTG | 16 | BsaI |
| GAACCGTCTCACGATATAATCTGGAACAAGTACCTTGC | 17 | BsmBI |
| GAACCGTCTCAGAAGCACGAGCATAGTTTACTACG | 18 | BsmBI |
| GAACCGTCTCAAAGGTGGGTTTATGTGCCG | 19 | BsmBI |
| GAACGTCTCAGGAATCCAAATGGCGGATATTCCCGC | 20 | BsmAI |
| GAACGGTCTCAGTTTATCATATTGATGAGCTCC | 21 | BsaI |
| GAACCGTCTCAGAGGTAGTTGGCAGTATATTTG | 22 | BsmBI |
| GAACGTCTCACGCCAGGCATCAACGCCGATG | 23 | BsmAI |
| GAACGTCTCATTGTAGTAGAGCGGGAAGTC | 24 | BsmAI |
| GAACGGTCTCAATCGGTGTCGTGGTTTGCTAC | 25 | BsaI |
| GAACCGTCTCACTTCCACCTGCGAGGTGGTC | 26 | BsmBI |
| GAACCGTCTCACCTTCCAACCTTGCTCGAGC | 27 | BsmBI |
| TCGAGACTGACTCTCACCCAACACCGCAATAGC | 28 |  |
| GAACACTAGTAGGAGGTAACTTATGGCCAAGTACCTGGAGCTCGAAGAGG | 29 | SpeI |
| GAACGGTCTCATTCCCCCGGCGAGCAAGGGC | 30 | BsaI |
| GAACCGTCTCAAAACACCGCCCACGCCTACGG | 31 | BsmBI |
| GAACGTCTCACCTCGACTTCCACCCCAAC | 32 | BsmAI |
| GAACGTCTCAGGCGCTTCGACTACGTCAAGG | 33 | BsmAI |
| GAACGGTCTCAACAAGATGGACGCGGCCTTTGAC | 34 | BsaI |
| GAACCGTCTCACGATATAATTTGGAACAAGTACCC | 35 | BsmBI |

TABLE 1-continued

| | SEQ ID NO: | |
|---|---|---|
| GAACCGTCTCAGAAGCACCGACATAGTCTAC | 36 | BsmBI |
| GAACCGTCTCAAAGGTGGGTCTACGTTCCG | 37 | BsmBI |
| GAACGTCTCAGGAATCCATATTGCGGAGATTCCGGC | 38 | BsmAI |
| GAACGGTCTCAGTTTATCATGTTCACGAGCTC | 39 | BsaI |
| GAACCGTCTCAGAGGTAGTTGGCCGTGTACTTG | 40 | BsmBI |
| GAACGTCTCAGCCATGCGTCAACGCCGATG | 41 | BsmAI |
| GAACGTCTCATTGTAGTAGAGCGGGAAGTCG | 42 | BsmAI |
| GAACGGTCTCAATCGGTGTCGTGGTTTGCAACG | 43 | BsaI |
| GAACCGTCTCACTTCCACCGGCGAGGTGGTCGTG | 44 | BsmBI |
| GAACCGTCTCACCTTCCGGCCTTGCTCGAGCC | 45 | BsmBI |
| TCGAGACTGACTCTCAGCCCACCCCGCAGTAGCTC | 46 | |
| GAACACTAGTAGGAGGTAACTTATGGCCAAGTACTCCGAGCTGGAAGAGG | 47 | SpeI |
| GAACGGTCTCATTCCTCCCGCGAGCAAGGG | 48 | BsaI |
| GAACCGTCTCAAAACACCGCCCACGCCTATG | 49 | BsmBI |
| GAACGTCTCACCTCGACTTCCACCCGAACGAGC | 50 | BsmAI |
| GAACGTCTCAGGCGCTTCGACTACGTCAAGG | 51 | BsmAI |
| GAACGGTCTCAACAAGATGGACGAGGCCTTCG | 52 | BsaI |
| GAACCGTCTCACGATATAATCTGGAACAAG | 53 | BsmBI |
| GAACCGTCTCAGAAGCACTGACATCGTTTACTACG | 54 | BsmBI |
| GAACCGTCTCAAAGGTGGGTTTACGTTCCG | 55 | BsmBI |
| GAACGTCTCAGGAATCCATATCGCCGAAAT | 56 | BsmAI |
| GAACGGTCTCAGTTTATCATGTTTATGAGC | 57 | BsaI |
| GAACCGTCTCAGAGGTAGTTGGCCGTGTATTTAC | 58 | BsmBI |
| GAACGTCTCACGCCAGGCATCGATGCCGAT | 59 | BsmAI |
| GAACGTCTCATTGTAGTAGAGGGCGAAGTCAAAG | 60 | BsmAI |
| GAACGGTCTCAATCGGTATCGTGGTTGGCTACAAAC | 61 | BsaI |
| GAACCGTCTCACTTCCTCCGGCGAGGTTGTCATG | 62 | BsmBI |
| GAACCGTCTCACCTTCCGGCTTTGCTTGAGGC | 63 | BsmBI |
| TCGAGACTGACTCTCACCCAACACCGCAGTAGCTCC | 64 | |
| CACACAGCAGCAACCAACCTCGAGACTGACTCTCASCC | 65 | BbvI |

Conditions used for PCR were as follows: 3 min 94° C., (30 sec 94° C.; 30 sec 55° C., 30 sec 68° C.)×30 cycles, followed by 10 min 68° C. PCR products corresponding to homologous regions from the three parents were pooled (1:1:1), cut with the appropriate restriction enzyme (see Table 3), and gel-purified. Equal amounts of fragment pools were combined and ligated (16° C.; overnight). The resulting 450 bp ligation products were gel purified and ligated to yield full length amylase genes. The resulting full length products were gel-purified and PCR amplified using a mixture of F1 primers SEQ ID NO.: 6, SEQ ID NO.: 66, SEQ ID NO.: 67 and primer SEQ ID NO:65. Conditions used for PCR were as follows: 3 min 94° C., (30 sec 94° C.; 30 sec 50° C., 60 sec 68° C.)×30 cycles, followed by 10 min 68° C. The resulting PCR products (~1.4 kbp) were purified, cut with SpeI and BbvI, gel-purified, ligated into pMYC (vector from Mycogen, cut with SpeI/XhoI), and transformed into *E. coli* Top10. Plasmid DNA from a pool of ~21000 colonies was isolated and transformed into *Pseudomonas*.

Screening of Reassembled α-Amylase

The transformed *Pseudomonas fluorescens* (MB214) containing pMYC derived from the parent clones SEQ ID NO:6, SEQ ID NO:66, SEQ ID NO:68 were sorted to 96- or 384-well plates by FACS and treated with 6M urea. Primary screening using RBB-starch and/or FITC-starch as substrates was carried out as described more fully below. Elevated active clones were screened using RBB-starch as substrate using induced cultures and by liquefaction assay. Stock and sequencing new elevated active clones based on liquefaction data was performed.

The transformed reassembled amylase library (MB214 (Pf)), were collected and sorted into 96-well plates (or 384-well plates) at 1 cell/well in 50 μl of LB+Tet. The plates were incubated for 24 hours at 30° C. Replicate plates were made corresponding to each well for storage. Forty-five (45) μl of 12M urea was added to each well and the plates were shaken for 10 minutes. Plates were kept at room temp for at least 1 hour and the lysate stored at 4° C.

Assay Using RBB-Starch

75 μl of RBB-starch substrate (1% RBB-insoluble corn starch in 50 mM NaAc buffer, pH=4.5) was added into each well of a new 96-well plate (V-bottom). Five micro-liters of enzyme lysate was transferred into each well with substrate using Biomek or Zymark. The plates were sealed with aluminum sealing tape and shaken briefly on the shaker. The plates were incubated at 90° C. for 30 minutes, followed by cooling at room temperature for about 5 to 10 minutes. One hundred micro-liters of 100% ethanol was added to each well, the plates sealed and shaken briefly on the shaker. The plates were then centrifuged 4000 rpm for 20 minutes using bench-top centrifuge. 100 μl of the supernatant was transferred into a new 96-well plate (flat bottom) by Biomek and read $OD_{595}$. Controls: SEQ ID NO:6, SEQ ID NO:66, SEQ ID NO:68.

Assay Using FITC-Starch

Added 50 μl of substrate (0.01% FITC-starch in 100 mM NaAc buffer, pH=4.5) into each well of a new 384-well plate. Transferred 5 μl of enzyme lysate into each well with substrate and incubated the plate at room temperature overnight. The polarization change of the substrate, excitation 485 nm, emission 535 nm, was read for each well. Controls: SEQ ID NO: 6, SEQ ID NO: 66, SEQ ID NO: 68. 96 well plates can be used for all assays.

Confirmation of New Active Clones

Each positive clone from screening was grown and induced using a standard protocol. Each clone was examined for growth (i.e., cell density over time), activity at per cell level (RBB-starch assay and liquefaction assay), expression (protein gel) and solubility of protein (by microscope analysis). The confirmed new elevated clones were transferred for fermentation. One of the clones have amylase activity greater than that of the parent includes the enzyme set forth in SEQ ID NO:2 (encoded by SEQ ID NO:1).

A number of embodiments of the invention have been described. Nevertheless, it will be understood that various modifications may be made without departing from the spirit and scope of the invention. Accordingly, other embodiments are within the scope of the following claims.

What is claimed is:

1. A method for producing an oil from a grain milling process comprising:
   (a) providing at least one alpha-amylase having at least 96% sequence identity to the amino acid sequence as set forth in SEQ ID NO:2;
   (b) providing a composition comprising a starch;
   (c) contacting the alpha-amylase of (a) with the composition of (b) under conditions wherein the alpha-amylase liquefies the starch to produce a water soluble starch solution
   (d) removing the solubles from the starch solution to produce the oil.

2. The method of claim 1, wherein the starch is a corn starch.

3. The method of claim 1, wherein the oil is endogenous to the corn.

4. The method of claim 1, wherein the removal or liquefaction of starch reduces viscosity of the water soluble starch solution.

5. The method of claim 4, wherein the reduction in viscosity improves the amount of oil produced.

6. The method of claim 5, wherein the alpha-amylase is thermostable at a temperature from about 37° C. to about 105° C.

7. The method of any of claim 1, wherein the alpha-amylase is active at low pH.

8. The method of claim 1, wherein the alpha-amylase is active at about pH 4 to about pH 6.

* * * * *

UNITED STATES PATENT AND TRADEMARK OFFICE
CERTIFICATE OF CORRECTION

PATENT NO. : 10,066,222 B2
APPLICATION NO. : 15/636039
DATED : September 4, 2018
INVENTOR(S) : Walter Callen et al.

Page 1 of 1

It is certified that error appears in the above-identified patent and that said Letters Patent is hereby corrected as shown below:

In page 2, column 1, item (56), references cited, other publications, delete "SIPO--Feb. 20, 2014--Thrid Office Action--CN201210020583.5." and insert --SIPO--Feb. 20, 2014--Third Office Action--CN201210020583.5--, therefor.

Signed and Sealed this
Twenty-seventh Day of November, 2018

Andrei Iancu
*Director of the United States Patent and Trademark Office*

SEQUENCE LISTING

<160> NUMBER OF SEQ ID NOS: 69

<210> SEQ ID NO 1
<211> LENGTH: 1311
<212> TYPE: DNA
<213> ORGANISM: Artificial Sequence
<220> FEATURE:
<223> OTHER INFORMATION: Synthetically generated

<400> SEQUENCE: 1

```
atggccaagt actccgagct ggaaaagggc ggggtcataa tgcaggcgtt ctactgggac     60
gtgccttcag gaggaatatg gtgggacaca atacggcaga agataccgga gtggtacgat    120
gccggaatct ccgcaatatg gattcccccg gcgagcaagg gcatgggcgg cgcctattcg    180
atgggctacg accctacga cttctttgac ctcggtgagt acgaccagaa gggaacggta    240
gagacgcgct ttggctccaa gcaggagctc gtgaacatga taaacaccgc ccacgcctat    300
ggcatgaagg taatagccga tatagtcatc aaccaccgcg ccggcggtga cctggagtgg    360
aaccccttcg tgaacgacta tacctggacc gacttctcaa aggtcgcgtc gggtaaatac    420
acggccaact acctcgactt ccacccgaac gagctccatg cgggcgattc cggaacattt    480
ggaggctatc ccgacatatg ccacgacaag agctgggacc agtactggct ctgggccagc    540
caggagagct acgcggcata tctcaggagc atcggcatcg atgcctggcg cttcgactac    600
gtcaagggct atgctccctg gtcgtcaag gactggctga actggtgggg aggctgggcg    660
gttgagagt actgggacac caacgtcgac gctgttctca actgggcata ctcgagcggt    720
gccaaggtct ttgacttcgc cctctactac aagatggatg aggcctttga acaaaaaac    780
attccagcgc tcgtctctgc ccttcagaac ggccagactg ttgtctcccg cgacccgttc    840
aaggccgtaa cctttgtagc aaaccacgac accgatataa tctggaacaa gtatccagcc    900
tacgcgttca tcctcaccta cgagggccag ccgacaatat tctaccgcga ctacgaggag    960
tggctcaaca aggataagct caagaacctc atctggatac atgagaacct cgccggagga   1020
agcaccgaca tagtctacta cgataacgat gaactcatct tcgtcaggaa cggctacggg   1080
gacaagccgg ggcttataac ctacatcaac ctaggctcga gcaaggccgg aaggtgggtt   1140
tatgtgccga gttcgcgggg cgcgtgcatc cacgagtata ctggtaacct cggaggctgg   1200
gtagacaagt acgtctactc aagcggctgg gtctatctcg aagctccagc ttacgaccct   1260
gccaacgggc agtatggcta ctccgtgtgg agctactgcg gggtgggctg a            1311
```

<210> SEQ ID NO 2
<211> LENGTH: 436
<212> TYPE: PRT
<213> ORGANISM: Artificial Sequence
<220> FEATURE:
<223> OTHER INFORMATION: Synthetically engineered

<400> SEQUENCE: 2

```
Met Ala Lys Tyr Ser Glu Leu Glu Lys Gly Gly Val Ile Met Gln Ala
  1               5                  10                  15

Phe Tyr Trp Asp Val Pro Ser Gly Gly Ile Trp Trp Asp Thr Ile Arg
                 20                  25                  30

Gln Lys Ile Pro Glu Trp Tyr Asp Ala Gly Ile Ser Ala Ile Trp Ile
             35                  40                  45

Pro Pro Ala Ser Lys Gly Met Gly Gly Ala Tyr Ser Met Gly Tyr Asp
         50                  55                  60

Pro Tyr Asp Phe Phe Asp Leu Gly Glu Tyr Asp Gln Lys Gly Thr Val
```

```
                 65                  70                  75                  80
        Glu Thr Arg Phe Gly Ser Lys Gln Glu Leu Val Asn Met Ile Asn Thr
                         85                  90                  95

Ala His Ala Tyr Gly Met Lys Val Ile Ala Asp Ile Val Ile Asn His
                        100                 105                 110

Arg Ala Gly Gly Asp Leu Glu Trp Asn Pro Phe Val Asn Asp Tyr Thr
                        115                 120                 125

Trp Thr Asp Phe Ser Lys Val Ala Ser Gly Lys Tyr Thr Ala Asn Tyr
                130                 135                 140

Leu Asp Phe His Pro Asn Glu Leu His Ala Gly Asp Ser Gly Thr Phe
        145                 150                 155                 160

Gly Gly Tyr Pro Asp Ile Cys His Asp Lys Ser Trp Asp Gln Tyr Trp
                        165                 170                 175

Leu Trp Ala Ser Gln Glu Ser Tyr Ala Ala Tyr Leu Arg Ser Ile Gly
                        180                 185                 190

Ile Asp Ala Trp Arg Phe Asp Tyr Val Lys Gly Tyr Ala Pro Trp Val
                        195                 200                 205

Val Lys Asp Trp Leu Asn Trp Trp Gly Gly Trp Ala Val Gly Glu Tyr
                210                 215                 220

Trp Asp Thr Asn Val Asp Ala Val Leu Asn Trp Ala Tyr Ser Ser Gly
        225                 230                 235                 240

Ala Lys Val Phe Asp Phe Ala Leu Tyr Tyr Lys Met Asp Glu Ala Phe
                        245                 250                 255

Asp Asn Lys Asn Ile Pro Ala Leu Val Ser Ala Leu Gln Asn Gly Gln
                        260                 265                 270

Thr Val Val Ser Arg Asp Pro Phe Lys Ala Val Thr Phe Val Ala Asn
                275                 280                 285

His Asp Thr Asp Ile Ile Trp Asn Lys Tyr Pro Ala Tyr Ala Phe Ile
                290                 295                 300

Leu Thr Tyr Glu Gly Gln Pro Thr Ile Phe Tyr Arg Asp Tyr Glu Glu
        305                 310                 315                 320

Trp Leu Asn Lys Asp Lys Leu Lys Asn Leu Ile Trp Ile His Glu Asn
                        325                 330                 335

Leu Ala Gly Gly Ser Thr Asp Ile Val Tyr Tyr Asp Asn Asp Glu Leu
                        340                 345                 350

Ile Phe Val Arg Asn Gly Tyr Gly Asp Lys Pro Gly Leu Ile Thr Tyr
                        355                 360                 365

Ile Asn Leu Gly Ser Ser Lys Ala Gly Arg Trp Val Tyr Val Pro Lys
                370                 375                 380

Phe Ala Gly Ala Cys Ile His Glu Tyr Thr Gly Asn Leu Gly Gly Trp
        385                 390                 395                 400

Val Asp Lys Tyr Val Tyr Ser Ser Gly Trp Val Tyr Leu Glu Ala Pro
                        405                 410                 415

Ala Tyr Asp Pro Ala Asn Gly Gln Tyr Gly Tyr Ser Val Trp Ser Tyr
                        420                 425                 430

Cys Gly Val Gly
                435

<210> SEQ ID NO 3
<211> LENGTH: 1419
<212> TYPE: DNA
<213> ORGANISM: Unknown
<220> FEATURE:
<223> OTHER INFORMATION: Environmental sample
```

<400> SEQUENCE: 3

```
atgttcctgc tcgcgttttt gctcactgcc tcgctgttct gcccaacagg acagcccgcc      60
aaggctgccg caccgtttaa cggcaccatg atgcagtatt ttgaatggta cttgccggat     120
gatggcacgt tatggaccaa agtggccaat gaagccaaca acttatccag ccttggcatc     180
accgctcttt ggctgccgcc cgcttacaaa ggaacaagcc gcagcgacgt agggtacgga     240
gtatacgact gtatgacct cggcgaattc aatcaaaaag ggaccgtccg cacaaaatac     300
ggaacaaaag ctcaatatct tcaagccatt caagccgccc acgccgctgg aatgcaagtg     360
tacgccgatg tcgtgttcga ccataaaggc ggcgctgacg gcacggaatg ggtggacgcc     420
gtcgaagtca atccgtccga ccgcaaccaa gaaatctcgg gcacctatca aatccaagca     480
tggacgaaat ttgattttcc cgggcggggc aacacctact ccagctttaa gtggcgctgg     540
taccattttg acggcgttga ttgggacgaa agccgaaaat tgagccgcat ttacaaattc     600
cgcggcatcg gcaaagcgtg ggattgggaa gtagacacgg aaaacggaaa ctatgactac     660
ttaatgtatg ccgaccttga tatggatcat cccgaagtcg tgaccgagct gaaaaactgg     720
gggaaatggt atgtcaacac aacgaacatt gatgggttcc ggcttgatgc cgtcaagcat     780
attaagttca gttttttttcc tgattggttg tcgtatgtgc gttctcagac tggcaagccg     840
ctatttaccg tcggggaata ttggagctat gacatcaaca agttgcacaa ttacattacg     900
aaaacagacg gaacgatgtc tttgtttgat gccccgttac acaacaaatt ttataccgct     960
tccaaatcag ggggcgcatt tgatatgcgc acgttaatga ccaatactct catgaaagat    1020
caaccgacat tggccgtcac cttcgttgat aatcatgaca ccgaacccgg ccaagcgctg    1080
cagtcatggg tcgacccatg gttcaaaccg ttggcttacg cctttattct aactcggcag    1140
gaaggatacc cgtgcgtctt ttatggtgac tattatggca ttccacaata taacattcct    1200
tcgctgaaaa gcaaaatcga tccgctcctc atcgcgcgca gggattatgc ttacggaacg    1260
caacatgatt atcttgatca ctccgacatc atcgggtgga caaggaaagg ggtcactgaa    1320
aaaccaggat ccgggctggc cgcactgatc accgatgggc cgggaggaag caaatggatg    1380
tactgttggc aaacaacacg ctggaaaagt gttctatga                          1419
```

<210> SEQ ID NO 4
<211> LENGTH: 1539
<212> TYPE: DNA
<213> ORGANISM: Unknown
<220> FEATURE:
<223> OTHER INFORMATION: Environmental sample

<400> SEQUENCE: 4

```
atgaaacaac aaaaacggct ttacgcccga ttgctgacgc tgttatttgc gctcatcttc      60
ttgctgcctc attctgcagc agcggcggca aatcttaatg ggacgctgat gcagtatttt     120
gaatggtaca tgcccaatga cggccaacat tggaagcgct tgcaaaacga ctcggcatat     180
ttggctgaac acgtattac tgccgtctgg attccccgg catataaggg aacgagccaa      240
gcggatgtgg gctacggtgc ttacgacctt tatgatttag gggagtttca tcaaaaaggg     300
acggttcgga caaagtacgg cacaaaagga gagctgcaat ctgcgatcaa agtcttcat     360
tcccgcgaca ttaacgttta cggggatgtg gtcatcaacc acaaaggcgg cgctgatgcg    420
accgaagatg taaccgcggt tgaagtcgat cccgctgacc gcaaccgcgt aatttcagga     480
gaacaccgaa ttaaagcctg gacacatttt catttttccgg ggcgcggcag cacatacagc    540
gattttaaat ggcattggta ccattttgac ggaaccgatt gggacgagtc ccgaaagctg    600
```

```
aaccgcatct ataagtttca aggaaaggct tgggattggg aagtttccaa tgaaaacggc      660
aactatgatt atttgatgta tgccgacatc gattatgacc atcctgatgt cgcagcagaa      720
attaagagat ggggcacttg gtatgccaat gaactgcaat tggacggttt ccgtcttgat      780
gctgtcaaac acattaaatt ttcttttttg cgggattggg ttaatcatgt cagggaaaaa      840
acggggaagg aaatgtttac ggtagctgaa tattggcaga atgacttggg cgcgctggaa      900
aactatttga acaaaacaaa ttttaatcat tcagtgtttg acgtgccgct tcattatcag      960
ttccatgctg catcgacaca gggaggcggc tatgatatga ggaaattgct gaacggtacg     1020 gtcgttttcca agcatccgtt gaaagcggtt acatttgtcg ataaccatga tacacagccg     1080
gggcaatcgc ttgagtcgac tgtccaaaca tggtttaagc cgcttgctta cgctttcatt     1140
ctcacaaggg aatctggata ccctcaggtt ttctacgggg atatgtacgg gacgaaagga     1200
gactcccagc gcgaaattcc tgccttgaaa cacaaaattg aaccgatctt aaaagcgaga     1260
aaacagtatg cgtacggagc acagcatgat tatttcgacc accatgacat tgtcggctgg     1320
acaagggaag gcgacagctc ggttgcaaat tcaggtttgg cggcattaat aacagacgga     1380
cccggtgggg caaagcgaat gtatgtcggc cggcaaaacg ccggtgagac atggcatgac     1440
attaccggaa accgttcgga gccggttgtc atcaattcgg aaggctgggg agagtttcac     1500
gtaaacggcg ggtcggtttc aatttatgtt caaagatag                            1539
```

<210> SEQ ID NO 5
<211> LENGTH: 1395
<212> TYPE: DNA
<213> ORGANISM: Unknown
<220> FEATURE:
<223> OTHER INFORMATION: Environmental sample

<400> SEQUENCE: 5

```
gtggtgcaca tgaagttgaa gtaccttgcc ttagttttgt tggctgtggc ttcgataggc       60
ctactctcga ctccagtggg tgctgccaag tactccgaac tcgaagaggg cggtgttata      120
atgcaggcct tctactggga tgttcccgga gggggaatct ggtgggacac cataagacag      180
aaaatcccgg agtggtacga cgctggaatc tcggcgtatt ggattcctcc agctagcaaa      240
gggatgggcg gtggttattc catgggctac gatccctacg atttctttga cctcggcgag      300
tactatcaga agggaacagt tgagacgcgc ttcggctcaa aggaggaact ggtgaacatg      360
ataaacaccg cacactccta tggcataaag gtgatagcgg acatagtcat aaaccaccgc      420
gccggtggag accttgagtg gaaccccttt gtaaacaact atacttggac agacttctcc      480
aaggtcgcct ccggtaaata cacggccaac taccttgact ccacccaaa cgaggtcaag      540 tgctgcgatg agggtacatt tggtgacttt ccggacatcg cccacgagaa gagctgggat      600
cagtactggc tctgggcaag caatgagagc tacgccgcat atctccggag catagggatc      660
gatgcatggc gtttcgacta cgtcaaaggt tacgagcgt gggttgttaa tgactggctc      720
agctggtggg gaggctgggc cgttggagag tactgggaca cgaacgttga tgcactcctt      780
aactgggcat acgacagcgg tgccaaggtc tttgacttcc cgctctacta caagatggac      840
gaagcctttg acaacaccaa catccccgct ttggtttacg ccctccagaa cggaggaaca      900
gtcgtttccc gcgatccctt caaggcagta actttcgttg ccaaccacga tacagatata      960
atctggaaca gtatccggc ttatgcgttc atccttacct atgagggaca gcctgttata     1020
ttttaccgcg actacgagga gtggctcaac aaggataagc ttaacaacct tatctggata     1080
```

```
cacgagcacc ttgccggagg aagtaccaag atcctctact acgataacga tgagctaata    1140
ttcatgaggg agggctacgg gagcaagccg ggcctcataa cctacataaa cctcggaaac    1200
gactgggccg agcgctgggt gaacgtcggc tcaaagtttg ccggctacac aatccatgaa    1260
tacacaggca atctcggtgg ctgggttgac aggtgggttc agtacgatgg atgggttaaa    1320
ctgacggcac ctcctcatga tccagccaac ggatattacg gctactcagt ctggagctac    1380
gcaggcgtcg gatga                                                     1395
```

<210> SEQ ID NO 6
<211> LENGTH: 1386
<212> TYPE: DNA
<213> ORGANISM: Unknown
<220> FEATURE:
<223> OTHER INFORMATION: Bacterial Sequence

<400> SEQUENCE: 6

```
atgaagaagt tgtcgccct gttcataacc atgttttttcg tagtgagcat ggcagtcgtt      60
gcacagccag ctagcgccgc aaagtattcc gagctcgaag aaggcggcgt tataatgcag     120
gccttctact gggacgtccc aggtggagga atctggtggg acaccatcag gagcaagata     180
ccggagtggt acgaggcggg aatatccgcc atttggattc cgccagccag caaggggatg     240
agcggcggtt actcgatggg ctacgatccc tacgatttct ttgacctcgg cgagtacaac     300
cagaagggaa ccatcgaaac gcgctttggc tctaaacagg agctcatcaa tatgataaac     360
acggcccatg cctacggcat aaaggtcata gcggacatcg tcataaacca ccgcgcaggc     420
ggagacctcg agtggaaccc gttcgttggg gactacacct ggacggactt ctcaaaggtg     480
gcctcgggca aatatactgc caactacctc gacttccacc ccaacgaggt caagtgctgt     540
gacgagggca catttggagg cttcccagac atagcccacg agaagagctg ggaccagcac     600
tggctctggg cgagcgatga gagctacgcc gcctacctaa ggagcatcgg cgttgatgcc     660
tggcgctttg actacgtgaa gggctacgga cgtgggtcg tcaaggactg gctcaactgg     720
tggggcggct gggccgttgg cgagtactgg gacaccaacg ttgatgcact cctcaactgg     780
gcctactcga gcgcgccaa ggtcttcgac ttcccgctct actacaagat ggatgaggcc     840
tttgacaaca aaaacattcc agcgctcgtc tctgcccttc agaacggcca gactgttgtc     900
tcccgcgacc cgttcaaggc cgtaaccttt gtagcaaacc acgacaccga tataatctgg     960
aacaagtacc ttgcttatgc tttcatcctc acctacgaag gccagcccgt catattctac    1020
cgcgactacg aggagtggct caacaaggac aggttgaaca acctcatatg gatacacgac    1080
cacctcgcag gtggaagcac gagcatagtc tactacgaca gcgacgagat gatcttcgtg    1140
aggaacggct atggaagcaa gcctggcctt ataacttaca tcaacctcgg ctcgagcaag    1200
gttggaaggt gggtttatgt gccgaagttc gcgggcgcgt gcatccacga gtatactggt    1260
aacctcggag gctgggtaga caagtacgtc tactcaagcg gctgggtcta tctcgaagct    1320
ccagcttacg accctgccaa cgggcagtat ggctactccg tgtggagcta ttgcggtgtt    1380
gggtga                                                               1386
```

<210> SEQ ID NO 7
<211> LENGTH: 472
<212> TYPE: PRT
<213> ORGANISM: Unknown
<220> FEATURE:
<223> OTHER INFORMATION: Environmental sample

<400> SEQUENCE: 7

-continued

```
Met Phe Leu Leu Ala Phe Leu Leu Thr Ala Ser Leu Phe Cys Pro Thr
 1               5                  10                  15
Gly Gln Pro Ala Lys Ala Ala Pro Phe Asn Gly Thr Met Met Gln
             20                  25                  30
Tyr Phe Glu Trp Tyr Leu Pro Asp Asp Gly Thr Leu Trp Thr Lys Val
         35                  40                  45
Ala Asn Glu Ala Asn Asn Leu Ser Ser Leu Gly Ile Thr Ala Leu Trp
 50                  55                  60
Leu Pro Pro Ala Tyr Lys Gly Thr Ser Arg Ser Asp Val Gly Tyr Gly
 65                  70                  75                  80
Val Tyr Asp Leu Tyr Asp Leu Gly Glu Phe Asn Gln Lys Gly Thr Val
             85                  90                  95
Arg Thr Lys Tyr Gly Thr Lys Ala Gln Tyr Leu Gln Ala Ile Gln Ala
             100                 105                 110
Ala His Ala Ala Gly Met Gln Val Tyr Ala Asp Val Val Phe Asp His
     115                 120                 125
Lys Gly Gly Ala Asp Gly Thr Glu Trp Val Asp Ala Val Glu Val Asn
 130                 135                 140
Pro Ser Asp Arg Asn Gln Glu Ile Ser Gly Thr Tyr Gln Ile Gln Ala
 145                 150                 155                 160
Trp Thr Lys Phe Asp Phe Pro Gly Arg Gly Asn Thr Tyr Ser Ser Phe
             165                 170                 175
Lys Trp Arg Trp Tyr His Phe Asp Gly Val Asp Trp Asp Glu Ser Arg
             180                 185                 190
Lys Leu Ser Arg Ile Tyr Lys Phe Arg Gly Ile Gly Lys Ala Trp Asp
             195                 200                 205
Trp Glu Val Asp Thr Glu Asn Gly Asn Tyr Asp Tyr Leu Met Tyr Ala
 210                 215                 220
Asp Leu Asp Met Asp His Pro Glu Val Val Thr Glu Leu Lys Asn Trp
 225                 230                 235                 240
Gly Lys Trp Tyr Val Asn Thr Thr Asn Ile Asp Gly Phe Arg Leu Asp
             245                 250                 255
Ala Val Lys His Ile Lys Phe Ser Phe Phe Pro Asp Trp Leu Ser Tyr
             260                 265                 270
Val Arg Ser Gln Thr Gly Lys Pro Leu Phe Thr Val Gly Glu Tyr Trp
             275                 280                 285
Ser Tyr Asp Ile Asn Lys Leu His Asn Tyr Ile Thr Lys Thr Asp Gly
     290                 295                 300
Thr Met Ser Leu Phe Asp Ala Pro Leu His Asn Lys Phe Tyr Thr Ala
 305                 310                 315                 320
Ser Lys Ser Gly Gly Ala Phe Asp Met Arg Thr Leu Met Thr Asn Thr
             325                 330                 335
Leu Met Lys Asp Gln Pro Thr Leu Ala Val Thr Phe Val Asp Asn His
             340                 345                 350
Asp Thr Glu Pro Gly Gln Ala Leu Gln Ser Trp Val Asp Pro Trp Phe
             355                 360                 365
Lys Pro Leu Ala Tyr Ala Phe Ile Leu Thr Arg Gln Glu Gly Tyr Pro
     370                 375                 380
Cys Val Phe Tyr Gly Asp Tyr Tyr Gly Ile Pro Gln Tyr Asn Ile Pro
 385                 390                 395                 400
Ser Leu Lys Ser Lys Ile Asp Pro Leu Leu Ile Ala Arg Arg Asp Tyr
             405                 410                 415
```

-continued

```
Ala Tyr Gly Thr Gln His Asp Tyr Leu Asp His Ser Asp Ile Ile Gly
                420                 425                 430

Trp Thr Arg Glu Gly Val Thr Glu Lys Pro Gly Ser Gly Leu Ala Ala
            435                 440                 445

Leu Ile Thr Asp Gly Pro Gly Gly Ser Lys Trp Met Tyr Cys Trp Gln
        450                 455                 460

Thr Thr Arg Trp Lys Ser Val Leu
465                 470

<210> SEQ ID NO 8
<211> LENGTH: 512
<212> TYPE: PRT
<213> ORGANISM: Unknown
<220> FEATURE:
<223> OTHER INFORMATION: Environmental sample

<400> SEQUENCE: 8

Met Lys Gln Gln Lys Arg Leu Tyr Ala Arg Leu Leu Thr Leu Leu Phe
  1               5                  10                  15

Ala Leu Ile Phe Leu Leu Pro His Ser Ala Ala Ala Ala Ala Asn Leu
                 20                  25                  30

Asn Gly Thr Leu Met Gln Tyr Phe Glu Trp Tyr Met Pro Asn Asp Gly
             35                  40                  45

Gln His Trp Lys Arg Leu Gln Asn Asp Ser Ala Tyr Leu Ala Glu His
         50                  55                  60

Gly Ile Thr Ala Val Trp Ile Pro Pro Ala Tyr Lys Gly Thr Ser Gln
 65                  70                  75                  80

Ala Asp Val Gly Tyr Gly Ala Tyr Asp Leu Tyr Asp Leu Gly Glu Phe
                 85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Arg Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190

Asp Trp Asp Glu Ser Arg Lys Leu Asn Arg Ile Tyr Lys Phe Gln Gly
        195                 200                 205

Lys Ala Trp Asp Trp Glu Val Ser Asn Glu Asn Gly Asn Tyr Asp Tyr
    210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
    290                 295                 300
```

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
            325                 330                 335

Leu Asn Gly Thr Val Val Ser Lys His Pro Leu Lys Ala Val Thr Phe
            340                 345                 350

Val Asp Asn His Asp Thr Gln Pro Gly Gln Ser Leu Glu Ser Thr Val
            355                 360                 365

Gln Thr Trp Phe Lys Pro Leu Ala Tyr Ala Phe Ile Leu Thr Arg Glu
            370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
            405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
            435                 440                 445

Ala Asn Ser Gly Leu Ala Ala Leu Ile Thr Asp Gly Pro Gly Gly Ala
450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
            485                 490                 495

Gly Glu Phe His Val Asn Gly Ser Val Ser Ile Tyr Val Gln Arg
            500                 505                 510

<210> SEQ ID NO 9
<211> LENGTH: 464
<212> TYPE: PRT
<213> ORGANISM: Unknown
<220> FEATURE:
<223> OTHER INFORMATION: Environmental sample

<400> SEQUENCE: 9

Val Val His Met Lys Leu Lys Tyr Leu Ala Leu Val Leu Leu Ala Val
1               5                   10                  15

Ala Ser Ile Gly Leu Leu Ser Thr Pro Val Gly Ala Ala Lys Tyr Ser
            20                  25                  30

Glu Leu Glu Glu Gly Gly Val Ile Met Gln Ala Phe Tyr Trp Asp Val
            35                  40                  45

Pro Gly Gly Gly Ile Trp Trp Asp Thr Ile Arg Gln Lys Ile Pro Glu
        50                  55                  60

Trp Tyr Asp Ala Gly Ile Ser Ala Ile Trp Ile Pro Pro Ala Ser Lys
65              70                  75                  80

Gly Met Gly Gly Gly Tyr Ser Met Gly Tyr Asp Pro Tyr Asp Phe Phe
                85                  90                  95

Asp Leu Gly Glu Tyr Tyr Gln Lys Gly Thr Val Glu Thr Arg Phe Gly
            100                 105                 110

Ser Lys Glu Glu Leu Val Asn Met Ile Asn Thr Ala His Ser Tyr Gly
            115                 120                 125

Ile Lys Val Ile Ala Asp Ile Val Ile Asn His Arg Ala Gly Gly Asp
        130                 135                 140

Leu Glu Trp Asn Pro Phe Val Asn Asn Tyr Thr Trp Thr Asp Phe Ser
145                 150                 155                 160

```
Lys Val Ala Ser Gly Lys Tyr Thr Ala Asn Tyr Leu Asp Phe His Pro
                165                 170                 175

Asn Glu Val Lys Cys Cys Asp Glu Gly Thr Phe Gly Asp Phe Pro Asp
            180                 185                 190

Ile Ala His Glu Lys Ser Trp Asp Gln Tyr Trp Leu Trp Ala Ser Asn
        195                 200                 205

Glu Ser Tyr Ala Ala Tyr Leu Arg Ser Ile Gly Ile Asp Ala Trp Arg
    210                 215                 220

Phe Asp Tyr Val Lys Gly Tyr Gly Ala Trp Val Asn Asp Trp Leu
225                 230                 235                 240

Ser Trp Trp Gly Gly Trp Ala Val Gly Glu Tyr Trp Asp Thr Asn Val
                245                 250                 255

Asp Ala Leu Leu Asn Trp Ala Tyr Asp Ser Gly Ala Lys Val Phe Asp
            260                 265                 270

Phe Pro Leu Tyr Tyr Lys Met Asp Glu Ala Phe Asp Asn Thr Asn Ile
        275                 280                 285

Pro Ala Leu Val Tyr Ala Leu Gln Asn Gly Gly Thr Val Val Ser Arg
    290                 295                 300

Asp Pro Phe Lys Ala Val Thr Phe Val Ala Asn His Asp Thr Asp Ile
305                 310                 315                 320

Ile Trp Asn Lys Tyr Pro Ala Tyr Ala Phe Ile Leu Thr Tyr Glu Gly
                325                 330                 335

Gln Pro Val Ile Phe Tyr Arg Asp Tyr Glu Glu Trp Leu Asn Lys Asp
            340                 345                 350

Lys Leu Asn Asn Leu Ile Trp Ile His Glu His Leu Ala Gly Gly Ser
        355                 360                 365

Thr Lys Ile Leu Tyr Tyr Asp Asn Asp Glu Leu Ile Phe Met Arg Glu
    370                 375                 380

Gly Tyr Gly Ser Lys Pro Gly Leu Ile Thr Tyr Ile Asn Leu Gly Asn
385                 390                 395                 400

Asp Trp Ala Glu Arg Trp Val Asn Val Gly Ser Lys Phe Ala Gly Tyr
                405                 410                 415

Thr Ile His Glu Tyr Thr Gly Asn Leu Gly Gly Trp Val Asp Arg Trp
            420                 425                 430

Val Gln Tyr Asp Gly Trp Val Lys Leu Thr Ala Pro His Asp Pro
    435                 440                 445

Ala Asn Gly Tyr Tyr Gly Tyr Ser Val Trp Ser Tyr Ala Gly Val Gly
450                 455                 460

<210> SEQ ID NO 10
<211> LENGTH: 461
<212> TYPE: PRT
<213> ORGANISM: Unknown
<220> FEATURE:
<223> OTHER INFORMATION: Bacterial Sequence

<400> SEQUENCE: 10

Met Lys Lys Phe Val Ala Leu Phe Ile Thr Met Phe Phe Val Val Ser
1               5                   10                  15

Met Ala Val Val Ala Gln Pro Ala Ser Ala Lys Tyr Ser Glu Leu
            20                  25                  30

Glu Glu Gly Gly Val Ile Met Gln Ala Phe Tyr Trp Asp Val Pro Gly
        35                  40                  45

Gly Gly Ile Trp Trp Asp Thr Ile Arg Ser Lys Ile Pro Glu Trp Tyr
    50                  55                  60
```

```
Glu Ala Gly Ile Ser Ala Ile Trp Ile Pro Pro Ala Ser Lys Gly Met
 65                  70                  75                  80

Ser Gly Gly Tyr Ser Met Gly Tyr Asp Pro Tyr Asp Phe Phe Asp Leu
                 85                  90                  95

Gly Glu Tyr Asn Gln Lys Gly Thr Ile Glu Thr Arg Phe Gly Ser Lys
            100                 105                 110

Gln Glu Leu Ile Asn Met Ile Asn Thr Ala His Ala Tyr Gly Ile Lys
        115                 120                 125

Val Ile Ala Asp Ile Val Ile Asn His Arg Ala Gly Gly Asp Leu Glu
    130                 135                 140

Trp Asn Pro Phe Val Gly Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln His Trp Leu Trp Ala Ser Asp Glu Ser
        195                 200                 205

Tyr Ala Ala Tyr Leu Arg Ser Ile Gly Val Asp Ala Trp Arg Phe Asp
    210                 215                 220

Tyr Val Lys Gly Tyr Gly Ala Trp Val Val Lys Asp Trp Leu Asn Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Gly Ala Lys Val Phe Asp Phe Pro
            260                 265                 270

Leu Tyr Tyr Lys Met Asp Glu Ala Phe Asp Asn Lys Asn Ile Pro Ala
        275                 280                 285

Leu Val Ser Ala Leu Gln Asn Gly Gln Thr Val Val Ser Arg Asp Pro
    290                 295                 300

Phe Lys Ala Val Thr Phe Val Ala Asn His Asp Thr Asp Ile Ile Trp
305                 310                 315                 320

Asn Lys Tyr Leu Ala Tyr Ala Phe Ile Leu Thr Tyr Glu Gly Gln Pro
                325                 330                 335

Val Ile Phe Tyr Arg Asp Tyr Glu Glu Trp Leu Asn Lys Asp Arg Leu
            340                 345                 350

Asn Asn Leu Ile Trp Ile His Asp His Leu Ala Gly Gly Ser Thr Ser
        355                 360                 365

Ile Val Tyr Tyr Asp Ser Asp Glu Met Ile Phe Val Arg Asn Gly Tyr
    370                 375                 380

Gly Ser Lys Pro Gly Leu Ile Thr Tyr Ile Asn Leu Gly Ser Ser Lys
385                 390                 395                 400

Val Gly Arg Trp Val Tyr Val Pro Lys Phe Ala Gly Ala Cys Ile His
                405                 410                 415

Glu Tyr Thr Gly Asn Leu Gly Gly Trp Val Asp Lys Tyr Val Tyr Ser
            420                 425                 430

Ser Gly Trp Val Tyr Leu Glu Ala Pro Ala Tyr Asp Pro Ala Asn Gly
        435                 440                 445

Gln Tyr Gly Tyr Ser Val Trp Ser Tyr Cys Gly Val Gly
    450                 455                 460

<210> SEQ ID NO 11
<211> LENGTH: 47
<212> TYPE: DNA
```

```
<213> ORGANISM: Artificial Sequence
<220> FEATURE:
<223> OTHER INFORMATION: Primer

<400> SEQUENCE: 11
gaacactagt aggaggtaac ttatggcaaa gtattccgag ctcgaag        47

<210> SEQ ID NO 12
<211> LENGTH: 39
<212> TYPE: DNA
<213> ORGANISM: Artificial Sequence
<220> FEATURE:
<223> OTHER INFORMATION: Primer

<400> SEQUENCE: 12
gaacggtctc attccgccag ccagcaaggg gatgagcgg              39

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
gaaccgtctc aaaacacggc ccatgcctac ggc                    33

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
gaacgtctca cctcgacttc caccccaacg aggtcaag               38

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
gaacgtctca ggcgctttga ctacgtgaag ggc                    33

<210> SEQ ID NO 16
<211> LENGTH: 32
<212> TYPE: DNA
<213> ORGANISM: Artificial Sequence
<220> FEATURE:
<223> OTHER INFORMATION: Primer

<400> SEQUENCE: 16
gaacggtctc aacaagatgg atgaggcctt tg                     32

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
gaaccgtctc acgatataat ctggaacaag taccttgc               38
```

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
gaaccgtctc agaagcacga gcatagttta ctacg          35

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
gaaccgtctc aaaggtgggt ttatgtgccg          30

<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
gaacgtctca ggaatccaaa tggcggatat tcccgc          36

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
gaacggtctc agtttatcat attgatgagc tcc          33

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
gaaccgtctc agaggtagtt ggcagtatat ttg          33

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
gaacgtctca cgccaggcat caacgccgat g          31

<210> SEQ ID NO 24
<211> LENGTH: 30
<212> TYPE: DNA
<213> ORGANISM: Artificial Sequence
<220> FEATURE:

<223> OTHER INFORMATION: Primer

<400> SEQUENCE: 24
gaacgtctca ttgtagtaga gcgggaagtc                                          30

<210> SEQ ID NO 25
<211> LENGTH: 32
<212> TYPE: DNA
<213> ORGANISM: Artificial Sequence
<220> FEATURE:
<223> OTHER INFORMATION: Primer

<400> SEQUENCE: 25
gaacggtctc aatcggtgtc gtggtttgct ac                                       32

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
gaaccgtctc acttccacct gcgaggtggt c                                        31

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
gaaccgtctc accttccaac cttgctcgag c                                        31

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
tcgagactga ctctcaccca acaccgcaat agc                                      33

<210> SEQ ID NO 29
<211> LENGTH: 50
<212> TYPE: DNA
<213> ORGANISM: Artificial Sequence
<220> FEATURE:
<223> OTHER INFORMATION: Primer

<400> SEQUENCE: 29
gaacactagt aggaggtaac ttatggccaa gtacctggag ctcgaagagg                    50

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
gaacggtctc attcccccgg cgagcaaggg c                                        31

```
<210> SEQ ID NO 31
<211> LENGTH: 32
<212> TYPE: DNA
<213> ORGANISM: Artificial Sequence
<220> FEATURE:
<223> OTHER INFORMATION: Primer

<400> SEQUENCE: 31
gaaccgtctc aaaacaccgc ccacgcctac gg                              32

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
gaacgtctca cctcgacttc caccccaac                                  29

<210> SEQ ID NO 33
<211> LENGTH: 31
<212> TYPE: DNA
<213> ORGANISM: Artificial Sequence
<220> FEATURE:
<223> OTHER INFORMATION: Primer

<400> SEQUENCE: 33
gaacgtctca ggcgcttcga ctacgtcaag g                               31

<210> SEQ ID NO 34
<211> LENGTH: 34
<212> TYPE: DNA
<213> ORGANISM: Artificial Sequence
<220> FEATURE:
<223> OTHER INFORMATION: Primer

<400> SEQUENCE: 34
gaacggtctc aacaagatgg acgcggcctt tgac                            34

<210> SEQ ID NO 35
<211> LENGTH: 35
<212> TYPE: DNA
<213> ORGANISM: Artificial Sequence
<220> FEATURE:
<223> OTHER INFORMATION: Primer

<400> SEQUENCE: 35
gaaccgtctc acgatataat ttggaacaag taccc                           35

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
gaaccgtctc agaagcaccg acatagtcta c                               31

<210> SEQ ID NO 37
<211> LENGTH: 30
<212> TYPE: DNA
<213> ORGANISM: Artificial Sequence
<220> FEATURE:
<223> OTHER INFORMATION: Primer
```

```
<400> SEQUENCE: 37
gaaccgtctc aaaggtgggt ctacgttccg                                         30

<210> SEQ ID NO 38
<211> LENGTH: 36
<212> TYPE: DNA
<213> ORGANISM: Artificial Sequence
<220> FEATURE:
<223> OTHER INFORMATION: Primer

<400> SEQUENCE: 38
gaacgtctca ggaatccata ttgcggagat tccggc                                  36

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
gaacggtctc agtttatcat gttcacgagc tc                                      32

<210> SEQ ID NO 40
<211> LENGTH: 33
<212> TYPE: DNA
<213> ORGANISM: Artificial Sequence
<220> FEATURE:
<223> OTHER INFORMATION: Primer

<400> SEQUENCE: 40
gaaccgtctc agaggtagtt ggccgtgtac ttg                                     33

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
gaacgtctca gccatgcgtc aacgccgatg                                         30

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
gaacgtctca ttgtagtaga gcgggaagtc g                                       31

<210> SEQ ID NO 43
<211> LENGTH: 33
<212> TYPE: DNA
<213> ORGANISM: Artificial Sequence
<220> FEATURE:
<223> OTHER INFORMATION: Primer

<400> SEQUENCE: 43
gaacggtctc aatcggtgtc gtggtttgca acg                                     33

<210> SEQ ID NO 44
<211> LENGTH: 34
```

<212> TYPE: DNA
<213> ORGANISM: Artificial Sequence
<220> FEATURE:
<223> OTHER INFORMATION: Primer

<400> SEQUENCE: 44
gaaccgtctc acttccaccg gcgaggtggt cgtg                              34

<210> SEQ ID NO 45
<211> LENGTH: 32
<212> TYPE: DNA
<213> ORGANISM: Artificial Sequence
<220> FEATURE:
<223> OTHER INFORMATION: Primer

<400> SEQUENCE: 45
gaaccgtctc accttccggc cttgctcgag cc                                32

<210> SEQ ID NO 46
<211> LENGTH: 35
<212> TYPE: DNA
<213> ORGANISM: Artificial Sequence
<220> FEATURE:
<223> OTHER INFORMATION: Primer

<400> SEQUENCE: 46
tcgagactga ctctcagccc accccgcagt agctc                             35

<210> SEQ ID NO 47
<211> LENGTH: 50
<212> TYPE: DNA
<213> ORGANISM: Artificial Sequence
<220> FEATURE:
<223> OTHER INFORMATION: Primer

<400> SEQUENCE: 47
gaacactagt aggaggtaac ttatggccaa gtactccgag ctggaagagg             50

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
gaacggtctc attcctcccg cgagcaaggg                                   30

<210> SEQ ID NO 49
<211> LENGTH: 31
<212> TYPE: DNA
<213> ORGANISM: Artificial Sequence
<220> FEATURE:
<223> OTHER INFORMATION: Primer

<400> SEQUENCE: 49
gaaccgtctc aaaacaccgc ccacgcctat g                                 31

<210> SEQ ID NO 50
<211> LENGTH: 33
<212> TYPE: DNA
<213> ORGANISM: Artificial Sequence
<220> FEATURE:
<223> OTHER INFORMATION: Primer

<400> SEQUENCE: 50

-continued gaacgtctca cctcgacttc cacccgaacg agc           33

<210> SEQ ID NO 51
<211> LENGTH: 31
<212> TYPE: DNA
<213> ORGANISM: Artificial Sequence
<220> FEATURE:
<223> OTHER INFORMATION: Primer

<400> SEQUENCE: 51
gaacgtctca ggcgcttcga ctacgtcaag g             31

<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52
gaacggtctc aacaagatgg acgaggcctt cg            32

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
gaaccgtctc acgatataat ctggaacaag              30

<210> SEQ ID NO 54
<211> LENGTH: 35
<212> TYPE: DNA
<213> ORGANISM: Artificial Sequence
<220> FEATURE:
<223> OTHER INFORMATION: Primer

<400> SEQUENCE: 54
gaaccgtctc agaagcactg acatcgttta ctacg         35

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
gaaccgtctc aaaggtgggt ttacgttccg              30

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
gaacgtctca ggaatccata tcgccgaaat              30

<210> SEQ ID NO 57
<211> LENGTH: 30
<212> TYPE: DNA
<213> ORGANISM: Artificial Sequence -continued

```
<220> FEATURE:
<223> OTHER INFORMATION: Primer

<400> SEQUENCE: 57
gaacggtctc agtttatcat gtttatgagc                                    30

<210> SEQ ID NO 58
<211> LENGTH: 34
<212> TYPE: DNA
<213> ORGANISM: Artificial Sequence
<220> FEATURE:
<223> OTHER INFORMATION: Primer

<400> SEQUENCE: 58
gaaccgtctc agaggtagtt ggccgtgtat ttac                               34

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
gaacgtctca cgccaggcat cgatgccgat                                    30

<210> SEQ ID NO 60
<211> LENGTH: 34
<212> TYPE: DNA
<213> ORGANISM: Artificial Sequence
<220> FEATURE:
<223> OTHER INFORMATION: Primer

<400> SEQUENCE: 60
gaacgtctca ttgtagtaga gggcgaagtc aaag                               34

<210> SEQ ID NO 61
<211> LENGTH: 36
<212> TYPE: DNA
<213> ORGANISM: Artificial Sequence
<220> FEATURE:
<223> OTHER INFORMATION: Primer

<400> SEQUENCE: 61
gaacggtctc aatcggtatc gtggttggct acaaac                             36

<210> SEQ ID NO 62
<211> LENGTH: 34
<212> TYPE: DNA
<213> ORGANISM: Artificial Sequence
<220> FEATURE:
<223> OTHER INFORMATION: Primer

<400> SEQUENCE: 62
gaaccgtctc acttcctccg gcgaggttgt catg                               34

<210> SEQ ID NO 63
<211> LENGTH: 32
<212> TYPE: DNA
<213> ORGANISM: Artificial Sequence
<220> FEATURE:
<223> OTHER INFORMATION: Primer

<400> SEQUENCE: 63
gaaccgtctc accttccggc tttgcttgag gc                                 32
```

<210> SEQ ID NO 64
<211> LENGTH: 36
<212> TYPE: DNA
<213> ORGANISM: Artificial Sequence
<220> FEATURE:
<223> OTHER INFORMATION: Primer

<400> SEQUENCE: 64
tcgagactga ctctcaccca acaccgcagt agctcc         36

<210> SEQ ID NO 65
<211> LENGTH: 38
<212> TYPE: DNA
<213> ORGANISM: Artificial Sequence
<220> FEATURE:
<223> OTHER INFORMATION: Primer

<400> SEQUENCE: 65
cacacagcag caaccaacct cgagactgac tctcascc         38

<210> SEQ ID NO 66
<211> LENGTH: 1299
<212> TYPE: DNA
<213> ORGANISM: Unknown
<220> FEATURE:
<223> OTHER INFORMATION: Environmental sample

<400> SEQUENCE: 66

| | | |
|---|---|---|
| atggctctgg aagagggcgg gctcataatg caggccttct actgggacgt ccccatggga | 60 |
| ggaatctggt gggacacgat agcccagaag atacccgact gggcaagcgc cgggatttcg | 120 |
| gcgatatgga tccctcccgc gagcaagggt atgagcggcg gctattcgat gggctacgac | 180 |
| ccctacgatt attttgacct cggtgagtac taccagaagg gaacggtgga aacgaggttc | 240 |
| ggctcaaagc aggagctcat aaacatgata acaccgccc acgcctatgg catgaaggta | 300 |
| atagccgata tagtcatcaa ccaccgcgcc ggcggtgacc tggagtggaa ccccttcgtg | 360 |
| aacgactata cctggaccga cttctcaaag gtcgcgtcgg gtaaatacac ggccaactac | 420 |
| ctcgacttcc acccgaacga gctccatgcg ggcgattccg gaacatttgg aggctatccc | 480 |
| gacatatgcc acgacaagag ctgggaccag tactggctct gggccagcca ggagagctac | 540 |
| gcggcatatc tcaggagcat cggcatcgat gcctggcgct tcgactacgt caagggctat | 600 |
| gctccctggg tcgtcaagga ctggctgaac tggtggggag gctggcggt tggagagtac | 660 |
| tgggacacca acgtcgacgc tgttctcaac tgggcatact cgagcggtgc caaggtcttt | 720 |
| gacttcgccc tctactacaa gatggacgag gccttcgata caacaacat tcccgccctg | 780 |
| gtggacgccc tcagatacgg tcagacagtg gtcagccgcg acccgttcaa ggctgtgacg | 840 |
| tttgtagcca accacgatac cgacataatc tggaacaagt atccagccta cgcgttcatc | 900 |
| ctcacctacg agggccagcc gacaatattc taccgcgact acgaggagtg gctcaacaag | 960 |
| gataagctca agaacctcat ctggatacat gacaacctcg ccggagggag cactgacatc | 1020 |
| gtttactacg acaacgacga gctgatattc gtgagaaacg gctacggaag caagccggga | 1080 |
| ctgataacat acatcaacct cgcctcaagc aaagccggaa ggtgggttta cgttccgaag | 1140 |
| ttcgcaggct cgtgcataca cgagtacacc ggcaatctcg gcggctgggt ggacaagtgg | 1200 |
| gtggactcaa cggctgggt ctacctcgag gctcctgccc acgacccggc caacggccag | 1260 |
| tacggctact ccgtctggag ctactgcggt gttgggtga | 1299 |

<210> SEQ ID NO 67
<211> LENGTH: 432
<212> TYPE: PRT
<213> ORGANISM: Unknown
<220> FEATURE:
<223> OTHER INFORMATION: Environmental sample

<400> SEQUENCE: 67

```
Met Ala Leu Glu Glu Gly Gly Leu Ile Met Gln Ala Phe Tyr Trp Asp
 1               5                  10                  15

Val Pro Met Gly Gly Ile Trp Trp Asp Thr Ile Ala Gln Lys Ile Pro
                20                  25                  30

Asp Trp Ala Ser Ala Gly Ile Ser Ala Ile Trp Ile Pro Pro Ala Ser
            35                  40                  45

Lys Gly Met Ser Gly Gly Tyr Ser Met Gly Tyr Asp Pro Tyr Asp Tyr
        50                  55                  60

Phe Asp Leu Gly Glu Tyr Tyr Gln Lys Gly Thr Val Glu Thr Arg Phe
 65                  70                  75                  80

Gly Ser Lys Gln Glu Leu Ile Asn Met Ile Asn Thr Ala His Ala Tyr
                 85                  90                  95

Gly Met Lys Val Ile Ala Asp Ile Val Ile Asn His Arg Ala Gly Gly
            100                 105                 110

Asp Leu Glu Trp Asn Pro Phe Val Asn Asp Tyr Thr Trp Thr Asp Phe
        115                 120                 125

Ser Lys Val Ala Ser Gly Lys Tyr Thr Ala Asn Tyr Leu Asp Phe His
    130                 135                 140

Pro Asn Glu Leu His Ala Gly Asp Ser Gly Thr Phe Gly Gly Tyr Pro
145                 150                 155                 160

Asp Ile Cys His Asp Lys Ser Trp Asp Gln Tyr Trp Leu Trp Ala Ser
                165                 170                 175

Gln Glu Ser Tyr Ala Ala Tyr Leu Arg Ser Ile Gly Ile Asp Ala Trp
            180                 185                 190

Arg Phe Asp Tyr Val Lys Gly Tyr Ala Pro Trp Val Val Lys Asp Trp
        195                 200                 205

Leu Asn Trp Trp Gly Gly Trp Ala Val Gly Glu Tyr Trp Asp Thr Asn
    210                 215                 220

Val Asp Ala Val Leu Asn Trp Ala Tyr Ser Ser Gly Ala Lys Val Phe
225                 230                 235                 240

Asp Phe Ala Leu Tyr Tyr Lys Met Asp Glu Ala Phe Asp Asn Asn Asn
                245                 250                 255

Ile Pro Ala Leu Val Asp Ala Leu Arg Tyr Gly Gln Thr Val Val Ser
            260                 265                 270

Arg Asp Pro Phe Lys Ala Val Thr Phe Val Ala Asn His Asp Thr Asp
        275                 280                 285

Ile Ile Trp Asn Lys Tyr Pro Ala Tyr Ala Phe Ile Leu Thr Tyr Glu
    290                 295                 300

Gly Gln Pro Thr Ile Phe Tyr Arg Asp Tyr Glu Glu Trp Leu Asn Lys
305                 310                 315                 320

Asp Lys Leu Lys Asn Leu Ile Trp Ile His Asp Asn Leu Ala Gly Gly
                325                 330                 335

Ser Thr Asp Ile Val Tyr Tyr Asp Asn Asp Glu Leu Ile Phe Val Arg
            340                 345                 350

Asn Gly Tyr Gly Ser Lys Pro Gly Leu Ile Thr Tyr Ile Asn Leu Ala
        355                 360                 365

Ser Ser Lys Ala Gly Arg Trp Val Tyr Val Pro Lys Phe Ala Gly Ser
```

-continued

```
        370                 375                 380
Cys Ile His Glu Tyr Thr Gly Asn Leu Gly Gly Trp Val Asp Lys Trp
385                 390                 395                 400

Val Asp Ser Ser Gly Trp Val Tyr Leu Glu Ala Pro Ala His Asp Pro
                405                 410                 415

Ala Asn Gly Gln Tyr Gly Tyr Ser Val Trp Ser Tyr Cys Gly Val Gly
            420                 425                 430
```

<210> SEQ ID NO 68
<211> LENGTH: 1386
<212> TYPE: DNA
<213> ORGANISM: Unknown
<220> FEATURE:
<223> OTHER INFORMATION: Bacterial Sequence

<400> SEQUENCE: 68

```
atgaagcctg cgaaactcct cgtctttgtg ctcgtagtct ctatcctcgc ggggctctac     60
gcccagcccg cggggcggc caagtacctg gagctcgaag agggcggcgt cataatgcag    120
gcgttctact gggacgtgcc ttcaggagga atatggtggg acacaatacg cagaagata    180
ccggagtggt acgatgccgg aatctccgca atatggattc ccccggcgag caagggcatg    240
ggcggcgcct attcgatggg ctacgacccc tacgacttct ttgacctcgg tgagtacgac    300
cagaagggaa cggtagagac gcgctttggc tccaagcagg agctcgtgaa catgataaac    360
accgcccacg cctacggcat caaggtcatc gcagacatag taatcaacca ccgcgccgga    420
ggagaccttg agtggaaccc cttcgtcaat gactacacct ggacggactt ctcgaaggtc    480
gcttccggca agtacacggc caactacctc gacttccacc caacgaggt caagtgctgc    540
gacgagggca cctttggagg gttcccggac atagcccacg agaagagctg ggaccagtac    600
tggctctggg cgagcaacga gagctacgcc gcctacctca ggagcatcgg cgttgacgca    660
tggcgcttcg actacgtcaa gggctacgga gcgtgggtcg tcaaggactg gctggactgg    720
tggggaggct gggccgtcgg ggagtactgg gacacaaacg ttgatgcact gctcaactgg    780
gcctactcga gcgatgcaaa agtcttcgac ttcccgctct actacaagat ggacgcggcc    840
tttgacaaca agaacattcc cgcactcgtc gaggccctca gaacggggg cacagtcgtc    900
agccgcgacc cgtttaaggc cgtaaccttc gttgcaaacc acgacacgga cataatttgg    960
aacaagtacc cggcctacgc cttcatcctc acctacgagg ccagccgac gatattctac   1020
cgcgactacg aggagtggct caacaaggac aggctcaaga acctcatctg gatacacgac   1080
cacctcgccg gtggaagcac cgacatagtc tactacgata cgatgaact catcttcgtc   1140
aggaacggct acggggacaa gccggggctt ataacctaca tcaacctagg ctcgagcaag   1200
gccgggaggt gggtctacgt tccgaagttc gcgggagcgt gcatccacga gtacaccggc   1260
aacctcggcg gctgggtgga caagtgggtg gactcaagcg ggtgggtgta cctcgaggcc   1320
cctgcccacg acccggccaa cggctattac ggctactccg tctggagcta ctgcggggtg   1380
ggctga                                                             1386
```

<210> SEQ ID NO 69
<211> LENGTH: 461
<212> TYPE: PRT
<213> ORGANISM: Unknown
<220> FEATURE:
<223> OTHER INFORMATION: Bacterial Sequence

<400> SEQUENCE: 69

```
Met Lys Pro Ala Lys Leu Leu Val Phe Val Leu Val Val Ser Ile Leu
 1               5                  10                  15

Ala Gly Leu Tyr Ala Gln Pro Ala Gly Ala Ala Lys Tyr Leu Glu Leu
            20                  25                  30

Glu Glu Gly Gly Val Ile Met Gln Ala Phe Tyr Trp Asp Val Pro Ser
        35                  40                  45

Gly Gly Ile Trp Trp Asp Thr Ile Arg Gln Lys Ile Pro Glu Trp Tyr
    50                  55                  60

Asp Ala Gly Ile Ser Ala Ile Trp Ile Pro Ala Ser Lys Gly Met
65                  70                  75                  80

Gly Gly Ala Tyr Ser Met Gly Tyr Asp Pro Tyr Asp Phe Phe Asp Leu
                85                  90                  95

Gly Glu Tyr Asp Gln Lys Gly Thr Val Glu Thr Arg Phe Gly Ser Lys
            100                 105                 110

Gln Glu Leu Val Asn Met Ile Asn Thr Ala His Ala Tyr Gly Ile Lys
            115                 120                 125

Val Ile Ala Asp Ile Val Ile Asn His Arg Ala Gly Gly Asp Leu Glu
        130                 135                 140

Trp Asn Pro Phe Val Asn Asp Tyr Thr Trp Thr Asp Phe Ser Lys Val
145                 150                 155                 160

Ala Ser Gly Lys Tyr Thr Ala Asn Tyr Leu Asp Phe His Pro Asn Glu
                165                 170                 175

Val Lys Cys Cys Asp Glu Gly Thr Phe Gly Gly Phe Pro Asp Ile Ala
            180                 185                 190

His Glu Lys Ser Trp Asp Gln Tyr Trp Leu Trp Ala Ser Asn Glu Ser
            195                 200                 205

Tyr Ala Ala Tyr Leu Arg Ser Ile Gly Val Asp Ala Trp Arg Phe Asp
        210                 215                 220

Tyr Val Lys Gly Tyr Gly Ala Trp Val Val Lys Asp Trp Leu Asp Trp
225                 230                 235                 240

Trp Gly Gly Trp Ala Val Gly Glu Tyr Trp Asp Thr Asn Val Asp Ala
                245                 250                 255

Leu Leu Asn Trp Ala Tyr Ser Ser Asp Ala Lys Val Phe Asp Phe Pro
            260                 265                 270

Leu Tyr Tyr Lys Met Asp Ala Ala Phe Asp Asn Lys Asn Ile Pro Ala
        275                 280                 285

Leu Val Glu Ala Leu Lys Asn Gly Gly Thr Val Val Ser Arg Asp Pro
290                 295                 300

Phe Lys Ala Val Thr Phe Val Ala Asn His Asp Thr Asp Ile Ile Trp
305                 310                 315                 320

Asn Lys Tyr Pro Ala Tyr Ala Phe Ile Leu Thr Tyr Glu Gly Gln Pro
                325                 330                 335

Thr Ile Phe Tyr Arg Asp Tyr Glu Glu Trp Leu Asn Lys Asp Arg Leu
            340                 345                 350

Lys Asn Leu Ile Trp Ile His Asp His Leu Ala Gly Gly Ser Thr Asp
        355                 360                 365

Ile Val Tyr Tyr Asp Asn Asp Glu Leu Ile Phe Val Arg Asn Gly Tyr
        370                 375                 380

Gly Asp Lys Pro Gly Leu Ile Thr Tyr Ile Asn Leu Gly Ser Ser Lys
385                 390                 395                 400

Ala Gly Arg Trp Val Tyr Val Pro Lys Phe Ala Gly Ala Cys Ile His
                405                 410                 415

Glu Tyr Thr Gly Asn Leu Gly Gly Trp Val Asp Lys Trp Val Asp Ser
```

-continued

```
            420                 425                 430
Ser Gly Trp Val Tyr Leu Glu Ala Pro Ala His Asp Pro Ala Asn Gly
            435                 440                 445

Tyr Tyr Gly Tyr Ser Val Trp Ser Tyr Cys Gly Val Gly
            450                 455             460
```